US007786308B2

(12) United States Patent
Drutu et al.

(10) Patent No.: US 7,786,308 B2
(45) Date of Patent: Aug. 31, 2010

(54) MUSCARINIC MODULATORS

(75) Inventors: Ioana Drutu, La Jolla, CA (US); Miguel Garcia-Guzman Blanco, San Diego, CA (US); Lewis R. Makings, Encinitas, CA (US); Gabriel Raffai, Temecula, CA (US); Valentin Boris Zunic, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1073 days.

(21) Appl. No.: 11/390,748

(22) Filed: Mar. 28, 2006

(65) Prior Publication Data

US 2007/0054911 A1 Mar. 8, 2007
US 2008/0090826 A9 Apr. 17, 2008

Related U.S. Application Data

(60) Provisional application No. 60/665,691, filed on Mar. 28, 2005.

(51) Int. Cl.
*C07D 211/56* (2006.01)
*C07D 211/98* (2006.01)
*C07D 211/00* (2006.01)
*C07D 211/08* (2006.01)
*C07D 401/00* (2006.01)
*C07D 211/06* (2006.01)
*C07D 211/92* (2006.01)
*A01N 43/40* (2006.01)
*A61K 31/445* (2006.01)

(52) U.S. Cl. ................. 546/244; 546/188; 546/191; 546/192; 546/195; 546/223; 514/315; 514/317

(58) Field of Classification Search ............... 546/216, 546/188, 184, 187, 191, 192, 194–214, 223, 546/229, 244; 514/315, 317
See application file for complete search history.

(56) References Cited

U.S. PATENT DOCUMENTS

| 4,198,417 | A | 4/1980 | Ong et al. |
| 5,153,228 | A | 10/1992 | Schlecker et al. |
| 6,245,773 | B1 | 6/2001 | Wong et al. |
| 6,268,369 | B1 | 7/2001 | Nagarathnam et al. |
| 6,514,993 | B1 | 2/2003 | Perregaard et al. |
| 6,956,042 | B2 | 10/2005 | Bhatti et al. |
| 6,977,263 | B2 | 12/2005 | Astles et al. |
| 2002/0037886 | A1 | 3/2002 | Andersson et al. |
| 2002/0049195 | A1 | 4/2002 | Mammen et al. |
| 2003/0199549 | A1 | 10/2003 | Bernett et al. |
| 2004/0029919 | A1 | 2/2004 | Mammen et al. |
| 2004/0038855 | A1 | 2/2004 | Salon et al. |
| 2004/0106623 | A1 | 6/2004 | Konkal et al. |
| 2004/0122014 | A1 | 6/2004 | Mammen et al. |
| 2004/0132710 | A1 | 7/2004 | Middleton et al. |
| 2004/0142956 | A1 | 7/2004 | Chen et al. |
| 2004/0142974 | A1 | 7/2004 | Hoemann |
| 2004/0167166 | A1* | 8/2004 | Alberati-Giani et al. .... 514/317 |
| 2005/0063909 | A1 | 3/2005 | Wright, IV et al. |
| 2005/0113413 | A1 | 5/2005 | Wilson et al. |

FOREIGN PATENT DOCUMENTS

WO  WO 2005/087236  9/2005

OTHER PUBLICATIONS

Bagley, James R., et al., "New 4-(Heteroanilido)piperidines, Structurally Related to the Pure Opiod Agonist Fentanyl, with Agonist and/or Antagonist Properties," *Journal of Medicinal Chemistry*, vol. 32, No. 3, pp. 663-671 [1989].

Caulfield, Malcolm P., "Muscarinic Receptors—Characterization, Coupling and Function," *Pharmaceutical Ther.*, vol. 58, pp. 319-379 [1993].

Caulfield, Malcolm P. and Birdsall, Nigel J. M., "International Union of Pharmacology. XVII. Classification of Muscarinic Acetylcholine Receptors," *Pharmacological Reviews*, vol. 50, No. 2, pp. 279-290 [1998].

Diouf, O., et al., "A New Series of M3 Muscarinic Antagonists Based on the 4-Amino-piperdine Scaffold," *Bioorganic & Medicinal Chemistry Letters*, 12, pp. 2535-2539 [2002].

Felder, Christian C., et al., "Therapeutic Opportunities for Muscarinic Receptors in the Central Nervous System," *Journal of Medicinal Chemistry*, vol. 43, No. 23, pp. 4333-4353 [2000].

Freireich, Emil J., et al., "Quantitative Comparison of Toxicity of Anticancer Agents in Mouse, Rat, Hamster, Dog, Monkey, and Man," *Cancer Chemotherapy Reports*, vol. 50, No. 4, pp. 219-244 [1966].

Hooper, Mark W., et al., "Scope and Mechanism of Palladium-Catalyzed Amination of Five-Membered Heterocyclic Halides," *Journal of Organic Chemistry*, vol. 68, No. 7, pp. 2861-2873 [2003].

Hulme, E. C., et al., "Muscarinic Receptor Subtypes," *Annual Reviews Pharmacol. Toxicology*, vol. 30, pp. 633-673 [1990].

Poulain, Rebecca, et al., "From Hit to Lead. Analyzing Structure—Profile Relationships," *Journal of Medicinal Chemistry*, vol. 44, No. 21, pp. 3391-3401 [2001].

International Search Report and Written Opinion of the International Searching Authority for International Application No. PCT/US2006/011139, filed Mar. 28, 2006.

Bando, Kazunori, et al., "Piperazine Analog of Vesamicol: in vitro and in vivo characterization for Vesicular Acetylcholine transporter", Synapse, (2000) 38(1), 27-37.

Chambers, M., "Spiropiperidines as High-Affinity, Selective σ Ligands", J. Med. Chem., 35(11) (1992), pp. 2033-2039.

(Continued)

*Primary Examiner*—Shengjun Wang
*Assistant Examiner*—Kendra D Carter
(74) *Attorney, Agent, or Firm*—Honigman Miller Schwartz & Cohn, LLP; Jonathan P. O'Brien; Heidi M. Berven

(57) ABSTRACT

The present invention relates to modulators of muscarinic receptors. The present invention also provides compositions comprising such modulators, and methods therewith for treating muscarinic receptor mediated diseases.

13 Claims, No Drawings

OTHER PUBLICATIONS

Daubin, W. G., et al., "Organic Reactions at High Pressure: Cycloadditions with Furans", J. Am. Chem. Soc., (1976) 98, 1992-1993.

Dhar, T.G., "Design and Synthesis of Novel α1a Adrenoceptor-Selective Antagonists. 2. Approaches to Eliminate Opioid Agonist Metabolites via Modification of Linker and 4-Methoxycarbonyl-4-phenylpiperidine Moiety1.2", J. Med. Chem, 42 (1999), pp. 4778-4793.

Eastwood, P. R., "A versitile synthesis of 4-aryl tetrahydropyridines via palladium mediated Suzuki cross-coupling with cyclic vinyl boronates", Tet. Lett. (2000) 41, 3705.

Efange, S., "Comparative Tissue Distribution of conformationally Restricted Radioiodinated Vesamicol Receptor Ligands", Nuclear Medicine and Biology, 22(4) (1995), pp. 437-444.

Evans, B., "Orally Active, Nonpeptide Oxytocin Antagonists", J. Med. Chem., 35(21) (1992), pp. 3919-3927.

Harriman, Geraldine, et al., "Synthesis of 4-substituted-4-aryl piperidines", Tet. Lett. (2000) 41, 8853.

Lazlo, Pierre, et al., "Easy Formation of Diels-Alder Cycloadducts Between Furans and Alpha, Beta Unsaturated Aldehydes and Ketones at Normal Pressure", Tet. Lett. (1984) 25, 4387-4388.

Minardi, G., et al., "3-Aminometil-2-Bornanoni N-Sostituiti", II Farmco Ed. Sc., (1969) 25(7), 513-536.

Moore, J. A., et al., "Catalyzed Addition of Furan with Acrylic Monomers", J. Org. Chem., (1983) 48, 1105-1106.

Mouithys-Mickalad, Ange, et al., "Synthesis and Pharmacological Evaluation of 6-Piperidinyl and 6-Piperizinylalkyl-2(3H)-Benzothiazolones as Mixed Alpha-5-HT1A Ligands", Bioorganic and Medicinal Chemistry Letters, (2002) 12(8), 1149-1152.

Nelson, W. L., et al., "Muscarinic Receptors. Derivatives of 7-Oxabicyclo[2.2.1]heptane", J. Med. Chem., (1971) 14, 698-702.

Sato, Susumu, et al., "New Mu Opiod Receptor Agonists with Phenoxyacetic Acid Moiety", Chemical and Pharmaceutical Bulletin, (2002) 50(2), 292-297.

Simpson, Merrill M., et al., "Dopamine D4/D2 Receptor Selectivity Is Determined by a Divergent Aromatic Microdomain Contained Within the Second, Third and Seventh Membrane-Spanning Segments", Molecular Pharmacology, (1999) 56(6), 1116-1126.

Thurkauf, Andrew, et al., "1-Phenyl-3-(aminomethyl) Pyrroles as Potencial Antipsychotic Agents. Synthesis and Dopamine Receptor Binding", J. Med. Chem, (1995) 38(25), 4950-4952.

Wang, Shaomeng, et al., "Pharmacophore-Based Discovery, Synthesis and Biological Evaluation of 4-Phenyl-1-Arylalkyl Piperidines as Dopamine Transporter Inhibitors", Bioorganic and Medicinal Chemistry Letters, (2001) 11, 495.

Wustrow, et al., "Coupling of Aryl Boronic Acids with Partially Reduced Pyridine Derivative", Synthesis, (1991) 11, 993.

* cited by examiner

MUSCARINIC MODULATORS

CLAIM OF PRIORITY

This application claims priority to U.S. provisional patent application Ser. No. 60/665,691 filed on Mar. 28, 2005, which is hereby incorporated by reference.

FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors-Characterization, Coupling, and Function," *Pharmacol. Ther.*, 58, pp. 319-379 (1993); Caulfield, M. P. et al., International Union of Pharmacology. XVII. "Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by, the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating activity of a muscarinic receptor comprising the step of contacting said receptor with a compound of formula I:

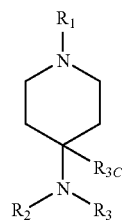

or a pharmaceutically acceptable salt thereof, wherein $R_1$, $R_2$, $R_3$, and $R_{3C}$ are defined below.

The present invention also provided compounds useful for modulating the activity of a muscarinic receptor.

In another aspect, the present invention features a pharmaceutical composition including such modulators.

In still another aspect, the invention features a method for treating muscarinic receptor mediated diseases with compounds of formula I.

In another aspect of the present invention, the compounds of formula Ia (described below) selectively modulate the $M_1$ muscarinic subtype.

DETAILED DESCRIPTION OF THE INVENTION

I. Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma, treatment of dry eyes and dry mouth, Sjögren's Syndrome, bradhycardia, gastric acid secretion, asthma, GI disturbances, and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, alkyl cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; ((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono-or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1 ]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, oxime, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono-or bicylic (fused or bridged) (e.g., 5-to 10-membered mono-or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl isoxazolidyl, morpholinyl, thiomorpholyl, octahydrobenzofuryl, octahydrochromenyl, octahydrothiochromenyl, octahydroindolyl, octahydropyrindinyl decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline. A "heterocycloalkenyl"

group, as used herein, refers to a mono-or bicylic (e.g., 5-to 10-membered mono-or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic) carbonyl, or (heteroaraliphatic)carbonyl], cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, oxime, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, benzthiazolyl, puryl, cinnolyl, quinolyl, quinazolyl cinnolyl, phthalazyl quinazolyl, quinoxalyl, isoquinolyl, 4H-quinolizyl, benzo-1,2,5-thiadiazolyl, or 1,8-naphthyridyl.

Without limitation monocyclic heteroaryls include furyl, thiophenyl, 2H-pyrrolyl, pyrrolyl, oxazolyl, thazolyl, imidazolyl, pyrazolyl, isoxazolyl, isothiazolyl 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono-and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R_x$—C(O)— (such as -alkyl-C(O)—, also referred to as "alkylcarbonyl") where $R_x$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—

O—$R^Z$ wherein $R^X$ and $R^Y$ have been defined above and $R^Z$ can be aliphatic, aryl, araliphatic, heterocycloaliphatic, heteroaryl, or heteroaralipathic.

As used herein, a "carboxy" group refers to —COOH, —COO$R^X$, —OC(O)H, —OC(O)$R^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, an "oxime" group refers to =N—O$R^X$, wherein $R_x$ is defined above.

As used herein, a "sulfo" group refers to —$SO_3$H or —$SO_3R_X$ when used terminally or —S(O)$_3$— when used internally.

As used herein, a "sulfamide" group refers to the structure —$NR^X$—S(O)$_2$—$NR^YR^Z$ when used terminally and —$NR^X$—S(O)$_2$—$NR^Y$— when used internally, wherein $R^X$, $R^Y$, and $R^Z$ have been defined above.

As used herein, a "sulfamoyl" group refers to the structure —S(O)$_2$—$NR^XR^Y$ or —$NR^X$—S(O)$_2$—$R^Z$ when used terminally; or —S(O)$_2$—$NR^X$— or —$NR^X$—S(O)$_2$— when used internally, wherein $R^X$, $R^Y$, and $R^Z$ are defined above.

As used herein a "sulfanyl" group refers to —S—$R^X$ when used terminally and —S— when used internally, wherein $R_x$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R_x$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—$R^X$ when used terminally and —S(O)$_2$— when used internally, wherein $R_x$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—$R^X$ or —SO—O—$R^X$, when used terminally and —O—S(O)— or —S(O)—O— when used internally, where $R_x$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure ($R^X$)$_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) wherein $R^X$ and $R^Y$ have been defined above.

As used herein, the term "amidino" group refers to the structure —C=(N$R^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl-or alkyl-O(CO)-aryl-) are examples of carboxy groups used internally.

As used herein, the term "amidino" group refers to the structure —C=(N$R^X$)N($R^XR^Y$) wherein $R^X$ and $R^Y$ have been defined above.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[$CH_2$]$_v$—, where v is 1-6. A branched aliphatic chain is a straight aliphatic chain that is substituted with one or more aliphatic groups. A branched aliphatic chain has the structure —[CHQ]$_v$-where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

As used herein, a "monocyclic, bicyclic, or tricyclic ring system" refers to cycloaliphatic, heterocycloaliphatic, aryl, or heteroaryl ring systems. Monocyclic ring systems include optionally substituted monocyclic cycloaliphatic, heterocycloaliphatic, aryl, or heteraryl groups such as cyclohexyl, piperidine, phenyl, pyridine, or the like. Bicyclic ring systems include optionally substituted fused bicyclic cycloaliphatic, heterocycloaliphatic, aryl or heteroaryl groups [e.g., indole, naphthalene, indene, or the like]; and optionally substituted bridged bicyclic cycloaliphatic or heterocycloaliphatic groups as defined above. Tricyclic ring systems also include optionally substituted fused tricyclic cycloaliphatic, heterocycloaliphatic, aryl, or heteraryl groups; and optionally substituted bridged tricyclic cycloaliphatic or heterocycloaliphatic groups [e.g., adamantanly, or the like].

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, L and other variables contained herein encompass specific groups, such as alkyl and aryl. Unless otherwise noted, each of the specific groups for the variables $R_1$, $R_2$, $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g. enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C-or $^{14}$C-enriched carbon are within the scope of this invention. Such compounds are useful, for example, as analytical tools or probes in biological assays.

II. Compounds

A. Generic Compounds

The present invention provides methods of modulating activity of a muscarinic receptor comprising the step of contacting said receptor with a compound of formula I:

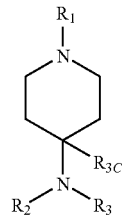

or a pharmaceutically acceptable salt thereof.

$R_1$ is -$Z^A R_4$, wherein each $Z^A$ is independently a bond or an optionally substituted branched or straight $C_{1-2}$ aliphatic chain. Each $R_4$ is independently an optionally substituted partially unsaturated or fully saturated 5-10 membered monocyclic, bicyclic, or tricyclic ring system having 0-3 heteroatoms selected from N, O, and S.

$R_2$ is -$Z^B R_5$, wherein each Z is independently a bond or a branched or straight $C_{1-5}$ aliphatic chain. Each $R_5$ is independently $R^B$, halo, —OH, —NH$_2$, —NO$_2$, —CN, —CF$_3$, or —OCH$_3$. Each $R^B$ is independently hydrogen or an optionally substituted cycloaliphatic, an optionally substituted heterocycloaliphatic, an optionally substituted aryl or an optionally substituted heteroaryl.

$R_3$ is -$Z^C R_6$, wherein each $Z^C$ is independently a bond or an optionally substituted branched or straight $C_{1-8}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—. Each $R_6$ is independently $R^C$, halo, —OH, —NH$_2$, —NO$_2$, —CN, —CF$_3$, or —OCH$_3$;

each $R^C$ is independently hydrogen, an optionally substituted $C_{1-8}$ aliphatic group, an optionally substituted aryl, or an optionally substituted cycloaliphatic.

$R_{3C}$ is hydrogen, or $R_{3C}$ and $R_3$ together with the atoms to they are attached form an optionally substituted 5-6 membered heterocycloaliphatic.

However, in several embodiments, when $Z^B$ is a bond and $R_5$ is an optionally substituted phenyl, $R_5$ is optionally substituted with 1-3 of halo, hydroxy, cyano, nitro, unsubstituted aliphatic, haloaliphatic, acyl, amino, amido, optionally substituted cycloaliphatic, optionally substituted heterocycloaliphatic, or combinations thereof.

B. Specific Embodiments

1. Substituent $R_1$:

$R_1$ is $Z^A R_4$, wherein each $Z^A$ is independently a bond or an optionally substituted branched or straight $C_{1-2}$ aliphatic chain. Each $R_4$ is independently an optionally substituted partially unsaturated or fully saturated 5-10 membered monocyclic, bicyclic, or tricyclic ring system having 0-3 heteroatoms selected from N, O, and S.

In several embodiments, $Z^A$ is independently a bond or a $C_{1-2}$ aliphatic chain.

In several embodiments, $R_1$ is optionally substituted with 1-3 of $R^{Z1}$. Each $R^{Z1}$ is independently an oxo, an oxime, or $R^{Z1}$ is -$Z^D R_7$, wherein each $Z^D$ is independently a bond or an optionally substituted branched or straight $C_{1-4}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$R$^D$—, —NR$^D$CO—, —S—, —S(O)—, —S(O)$_2$—, —NR$^D$—, —S(O)$_2$NR$^D$—, —NR$^D$S(O)$_2$—, or —NR$^D$S(O)$_2$NR$^D$—. Each $R_7$ is independently $R^D$, halo, —OH, —CN, —CF$_3$, or —OCH$_3$. Each $R^D$ is hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, $R_1$ is an optionally substituted partially unsaturated or fully saturated 5-10 membered monocyclic, bicyclic, or tricyclic ring system having 0-3 heteroatoms selected from N, O, and S. For example, $R_1$ is an optionally substituted 5-10 membered heterocycloaliphatic having 1-3 heteroatoms, an optionally substituted 5-10 membered cycloaliphatic, or an optionally substituted (cycloaliphatic) alkyl, wherein the cycloaliphatic group has 5-10 members.

In other embodiments, $R_1$ is an optionally substituted 5-10 membered heterocycloaliphatic having 1-3 heteroatoms selected from N, O, and S. In several examples, $R_1$ is a monocyclic heterocycloaliphatic optionally substituted with 1-3 of $R^{Z1}$. For example, $R_1$ is an optionally substituted 5-9 membered monocyclic heterocycloaliphatic. In other examples, $R_1$ is a pyrrolidine-yl; piperidine-yl; azepane-yl; azocane-yl; piperazine-yl; pyrazolidine-yl; imidazoline-yl; imidazolidine-yl; pyrroline-yl; tetrahydrofuranyl; 1,3-dioxolane-yl; tetrahydro-4H-pyran-yl; 1,4-dithiane-yl; morpholine-yl; thiomorpholine-yl; or 1,3,5-trithiane-yl, each of which is optionally substituted with 1-3 of 1-3 of $R^{Z1}$. In several examples, each $R^{Z1}$ is independently selected from halo, hydroxy, cyano, nitro, aliphatic, haloaliphatic, amido, amino, alkoxy, carboxy, cycloaliphatic, heterocycloaliphatic, aryl, and heteroaryl. In several examples, $R_1$ is an unsubstituted monocyclic heterocycloaliphatic. In alternative examples, $R_1$ is a 5-10 membered bicyclic heterocycloaliphatic having 1-3 heteroatoms selected from N, O, and S. For example, $R_1$ is a 6-10 membered optionally substituted bridged bicyclic heterocycloaliphatic or a 9-10 membered optionally substituted fused bicyclic heterocycloaliphatic. In other examples, $R_1$ is a 5-azabicyclo[2.1.1]hexane-yl; 7-azabicyclo[2.2.1]heptane-yl; or 8-azabicyclo[3.2.1]octane-yl; each of which is optionally substituted with 1-3 of $R^{Z1}$. In alternative examples, $R^{Z1}$ is alkoxycarbonyl or cycloalkoxycarbonyl; or $R_1$ is an unsubstituted bridged bicyclic heterocycloaliphatic.

In other embodiments, $R_1$ is an optionally substituted 5-10 membered cycloaliphatic. For example, $R_1$ is an optionally substituted 5-10 membered monocyclic, bicyclic, or tricyclic cycloaliphatic. In several examples, $R_1$ is an optionally substituted monocyclic cycloaliphatic. For example, $R_1$ is a cyclopropane-yl, cyclobutane-yl, cyclopentane-yl, cyclohexane-yl, cycloheptane-yl, or cyclooctane-yl; each of which is optionally substituted with 1-3 of $R^{Z1}$. In alternative examples, $R^{Z1}$ is independently selected from halo, oxo, alkyloxime, hydroxy, aliphatic, haloaliphatic, cycloaliphatic, heterocycloaliphatic, aryl, heteroaryl, alkoxy, amido, amino, carboxy, and acyl. In other examples, $R_1$ is an unsubstituted monocyclic cycloaliphatic. In several examples, $R_1$ is an optionally substituted bicyclic cycloaliphatic. For example, $R_1$ is an optionally substituted bridged bicyclic cycloaliphatic. In additional examples, $R_1$ is a bicyclo[3.2.1]octane-yl; bicyclo[3.3.1]nonane-yl; bicyclo[2.2.1]heptane-yl; bicyclo[2.1.1]hexane-yl; bicyclo[2.2.2]octane-yl; or bicyclo[3.1.1]heptane-yl, each of which is optionally substituted with 1-3 of $R^{Z1}$. In alternative examples, $R_1$ is an unsubstituted bicyclic cycloaliphatic. In further examples, $R_1$ is an optionally substituted tricyclic cycloaliphatic. For example, $R_1$ is an optionally substituted adamantanyl.

In several embodiments, $R_1$ is an optionally substituted (cycloaliphatic)alkyl. For example, $R_1$ is a (cyclopropyl)methyl, (cyclopropyl)ethyl, (cyclopropyl)propyl, (cyclopropyl)butyl, (cyclobutyl)methyl, (cyclobutyl)ethyl, (cyclobutyl) propyl, (cyclobutyl)butyl, (cyclopentyl)methyl, (cyclopentyl)ethyl, (cyclopentyl)propyl, (cyclohexyl)methyl, (cyclohexyl)ethyl, or (cyclohexyl)propyl, each of which is optionally substituted with 1-3 of $R^{Z1}$. In other examples, $R_1$ is an unsubstituted (cycloaliphatic)alkyl.

In several embodiments, $R_1$ is one selected from N-(ethoxy (carbonyl))piperidine-4-yl; N-(ethoxy(carbonyl))-8-azabicyclo[3.2.1]octane-3-yl; N-(butoxy(carbonyl))-8-azabicyclo[3.2.1]octane-3-yl; N-(isopropoxy(carbonyl))-8-azabicyclo[3.2.1]octane-3-yl; N-(tert-butoxy(carbonyl))-8-azabicyclo[3.2.1]octane-3-yl; N-(cyclobutoxy(carbonyl))-8-azabicyclo[3.2.1]octane-3-yl; tetrahydro-4H-pyran-4-yl; 4-(ethyl) cyclohexane-yl; bicyclo[2.2.1]heptane-2-yl; bicyclo[3.2.1]octane-3-yl; cyclohexane-yl; (cyclopentyl)methyl; bicyclo[2.2.1]hept-2-ylmethyl; cycloheptane-yl; cyclooctane-yl; bicyclo[3.3.1]nonane-9-yl; (tetrahydro-4H-pyran-2-yl)methyl; N-(butoxy(carbonyl))-8-azabicyclo[3.2.1]octane-3-yl; N-(2,2-difluoroethoxy(carbonyl))-8-azabicyclo[3.2.1]octane-3-yl; N-(2-fluoroethoxy(carbonyl))-8-azabicyclo[3.2.1]octane-3-yl; N-(but-2-ynoxy(carbonyl))-8-azabicyclo[3.2.1]octane-3-yl; N-(trifluoromethyl(carbonyl))-8-azabicyclo[3.2.1]octane-3-yl; N-(methoxy(carbonyl))-8-azabicyclo[3.2.1]octane-3-yl. N-(methoxy(ethoxy(carbonyl)))-8-azabicyclo[3.2.1]octane-3-yl; N-(ethyl(carbonyl))-8-azabicyclo[3.2.1]octane-3-yl; N-(phenyl(carbonyl))-8-azabicyclo[3.2.1]octane-3-yl; N-(N,N-(dimethyl(amino (carbonyl)))-8-azabicyclo[3.2.1]octane-3-yl; N-(phenyl (sulfonyl))-8-azabicyclo[3.2.1]octane-3-yl; 4-(ethoxy (imino))cyclohexane-yl; 4-(propoxy(imino))cyclohexane-yl; bicyclo[3.2.1]octane-3-yl; 4-(but-2-ynyloxyimino) cyclohexane-yl; and 4-(pent-2-ynyl(imino))cyclohexane-yl.

2. Substituent $R_2$:

$R_2$ is -$Z^B R_5$, wherein each $Z^B$ is independently a bond or a branched or straight $C_{1-5}$ aliphatic chain. Each $R_5$ is independently $R^B$, halo, —OH, —NH$_2$, —NO$_2$, —CN, —CF$_3$, or —OCH$_3$. Each $R^B$ is independently hydrogen or an optionally substituted cycloaliphatic, an optionally substituted heterocycloaliphatic, an optionally substituted aryl, or an optionally substituted heteroaryl.

In several embodiments, R$_2$ is optionally substituted with 1-5 of $R^{Z2}$. Each $R^{Z2}$ is -$Z^E$R$_8$, wherein each $Z^E$ is independently a bond or an optionally substituted branched or straight C$_{1-4}$ aliphatic chain wherein up to two carbon units of $Z^E$ are optionally and independently replaced by —CO—, —CS—, —CONR$^E$—, —CONR$^E$NR$^E$—, —CO$_2$—, —OCO—, —NR$^E$CO$_2$—, —O—, —NR$^E$CONR$^E$—, —OCONR$^E$, —NR$^E$NR$^E$—, —NR$^E$CO—, —S(O)—, —(O)$_2$—, —NR$^E$—, —S(O)$_2$NR$^E$—, —NR$^E$S(O)$_2$—, or NR$^E$S(O)$_2$NR$^E$—. Each R$_8$ is independently $R^E$, halo, —OH, —CN, —CF$_3$, or —OCF$_3$. Each $R^E$ is hydrogen, an optionally substituted C$_{1-4}$ aliphatic group, an optionally substituted cycloaliphatic, an optionally substituted heterocycloaliphatic, an optionally substituted aryl, or an optionally substituted heteroaryl.

In several embodiments, R$_2$ is an optionally substituted aryl. For example, R$_2$ is a monocyclic aryl or a bicyclic aryl, each of which is optionally substituted. In additional examples, R$_2$ is a phenyl optionally substituted with 1-5 of $R^{Z2}$, wherein each $R^{Z2}$ is independently selected from halo, hydroxy, cyano, amino, amido, acyl, alkoxy, aliphatic, cycloaliphatic, heterocycloaliphatic, aryl, and heteroaryl. In other examples, R$_2$ is an unsubstituted phenyl.

In several embodiments, R$_2$ is an optionally substituted branched or straight C$_{1-5}$ aliphatic chain. In several embodiments, R$_2$ is a methyl, ethyl, propyl, isopropyl, butyl, tert-butyl, isobutyl, or pentyl, each of which is optionally substituted. In several examples, R$_2$ is a methyl or an ethyl, each of which is optionally substituted with 1-3 of $R^{Z2}$, wherein each $R^{Z2}$ is independently selected from halo, hydroxy, cyano, nitro, amino, alkoxy, cycloaliphatic, heterocycloaliphatic, aryl, heteroaryl, or combinations thereof. In other examples, R$_2$ is a methyl optionally substituted with aryl or cycloaliphatic. In additional examples, R$_2$ is an unsubstituted propyl, isopropyl, butyl, tert-butyl, isobutyl, or pentyl.

In several embodiments, R$_2$ is an optionally substituted cycloaliphatic. For example, R$_2$ is a monocyclic cycloaliphathic or a bicyclic cycloaliphatic, each of which is optionally substituted. In several examples, R$_2$ is a monocyclic cycloaliphatic, such as cyclopropyl, cyclobutyl, cyclopentyl, or cyclohexyl, each of which is optionally substituted with 1-3 of $R^{22}$. In several examples, R$_2$ is an unsubstituted cyclopropyl, cyclobutyl, cyclopentyl, or cyclohexyl.

In several embodiments, R$_2$ is an optionally substituted heterocycloaliphatic. For example, R$_2$ is an optionally substituted monocyclic heterocycloaliphatic or an optionally substituted bicyclic heterocycloaliphatic. In additional examples, R$_2$ is a tetrahydrofuran-yl; thetrahydrothiophene-yl; 2-pyrroline-yl; pyrrolidine-yl; 1,3-dioxolane-yl; 2-imidazoline-yl; imidazolidine-yl; 2-pyrazoline-yl; pyrazolidine-yl; tetrahydropyran-yl; piperidine-yl; piperazine-yl; 1,4-dioxane-yl; morpholine-yl; 1,4-dithiane-yl; or thiomorpholine-yl, each of which is optionally substituted with 1-3 of $R^{Z2}$.

In several embodiments, R$_2$ is an optionally substituted heteroaryl. For example, R$_2$ is a monocyclic heteroaryl or a bicyclic heteroaryl, each of which is optionally substituted. In several examples, R$_2$ is an indole-yl; isoindole-yl; 3H-indole-yl; indoline-yl; benzo[b]furan-yl; benzo[b]thiophene-yl; benzimidazole-yl; benzthiazole-yl; purine-yl; quinoline-yl; isoquinoline-yl; cinnoline-yl; phthalazine-yl; quinazoline-yl; quinoxaline-yl; furanyl; thiophene-yl; thiazole-yl; pyridine-yl; pyrimidine-yl; pyrazine-yl; or 1,3,5-triazine-yl, each of which is optionally substituted with 1-3 of $R^{Z2}$, wherein each $R^{Z2}$ is independently selected from halo, aliphatic, alkoxy, acyl, aryl, heteroaryl, cycloaliphatic, and heterocycloaliphatic.

In several embodiments, R$_2$ is one selected from 4-fluorophenyl; phenyl; 2-fluorophenyl; phenylmethyl; 3-fluorophenyl; 4-methylphenyl; 3-methylphenyl; 3,4-dimethylphenyl; 2-methoxyphenyl; 3-methoxyphenyl; 4-(phenyl)phenyl; 4-methoxyphenyl; 4-(tert-butyl)phenyl; 3-chlorophenyl; 3-methoxycarbonyl; 4-chlorophenyl; cyclohexane-yl; 2,4-difluorophenyl; isopropyl; cyclopentane-yl; cyclobutane-yl; propyl; 2-chloro-4-methyl-pyrimidine-6-yl; and isobutyl.

In several embodiments, R$_2$ is hydrogen.

3. Substituent R$_3$:

R$_3$ is -$Z^C$R$_6$, wherein each $Z^C$ is independently a bond or an optionally substituted branched or straight C$_{1-8}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—. Each R$_6$ is independently $R^C$, halo, —OH, —NH$_2$, —NO$_2$, —CN, —CF$_3$, or —OCH$_3$. Each $R^C$ is independently hydrogen, an optionally substituted C$_{1-8}$ aliphatic group, an optionally substituted aryl, or an optionally substituted cycloaliphatic.

In several embodiments, each $Z^C$ is independently a bond or an optionally substituted branched or straight C$_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —S—, —S(O)—, —S(O)$_2$—, —NR$^C$—, —S(O)$_2$NR$^C$—, —NR$^C$S (O)$_2$—, or —NR$^C$S(O)$_2$NR$^C$—. R$_6$ is $R^C$, halo, —OH, —NH$_2$, —NO$_2$, —CN, —CF$_3$, or —OCF$_3$. $R^C$ is hydrogen, an optionally substituted C$_{1-8}$ aliphatic group, an optionally substituted aryl, or an optionally substituted cycloaliphatic.

In several embodiments, each $Z^C$ is independently a bond or an optionally substituted branched or straight C$_{1-4}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —S—, —S(O)—, —S(O)$_2$—, —NR$^C$—, —S(O)$_2$NR$^C$—, —NR$^C$S (O)$_2$—, or —NR$^C$S(O)$_2$NR$^C$—. R$_6$ is $R^C$, halo, —OH, —NH$_2$, —NO$_2$, —CN, —CF$_3$, or —OCF$_3$. $R^C$ is hydrogen, an optionally substituted C$_{1-8}$ aliphatic group, an optionally substituted aryl, or an optionally substituted cycloaliphatic.

In several embodiments, R$_3$ is optionally substituted with 1-3 of $R^{Z3}$. Each $R^{Z3}$ is -$Z^F$R$_9$, wherein each $Z^F$ is independently a bond or an optionally substituted branched or straight C$_{1-4}$ aliphatic chain wherein up to two carbon units of $Z^F$ are optionally and independently replaced by —CO—, —CS—, —CONR$^F$—, —CONR$^F$NR$^F$—, —CO$_2$—, —OCO—, —NR$^F$CO$_2$—, —O—, —NR$^F$CONR$^F$—, —OCONR$^F$—, —NR$^F$NR$^F$—, —NR$^F$CO—, —S—, —(O)—, —S(O)$_2$—, —NR$^F$—, —S(O)$_2$NR$^F$—, —NR$^F$S(O)$_2$—, or —NR$^F$S(O)$_2$NR$^F$—. Each R$_8$ is independently $R^F$, halo, —OH, —CN, —CF$_3$, or —OCF$_3$. Each $R^F$ is hydrogen, an optionally substituted C$_{1-4}$ aliphatic group, an optionally substituted cycloaliphatic, an optionally substituted heterocycloaliphatic, an optionally substituted aryl, or an optionally substituted heteroaryl.

In several embodiments, R$_3$ is a an optionally substituted branched or straight C$_{1-8}$ aliphatic chain wherein up to two carbon units are optionally and independently replaced by —CO—, —CS—, —CONR$^C$—, —CONR$^C$NR$^C$—, —CO$_2$—, —OCO—, —NR$^C$CO$_2$—, —O—, —NR$^C$CO-NR$^C$—, —OCONR$^C$—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—, and R$^C$ is hydrogen, an optionally substituted C$_{1-8}$ aliphatic group, an optionally substituted aryl, or an optionally substituted cycloaliphatic. For example, R$_3$ is an optionally substituted amido group. In additional examples, R$_3$ is an aminocarbonyl such as optionally substituted alkylaminocarbonyl. In more specific examples, R$_3$ is a methylaminocarbonyl, a N,N-dimethylaminocarbonyl, an ethylaminocarbonyl, a propylaminocarbonyl, or a butylaminocarbonyl; each of which is optionally substituted.

In several embodiments, R$_3$ is an acyl group such as optionally substituted (aliphatic)carbonyl. For example, R$_3$ is an alkylcarbonyl, an alkenylcarbonyl, or an alkynylcarbonyl; each of which is optionally substituted. In several examples, R$_3$ is a methylcarbonyl, an ethylcarbonyl, a propylcarbonyl, or a butylcarbonyl; each of which is optionally substituted with 1-3 of R$^{Z3}$. In several examples, R$_3$ is an unsubstituted methylcarbonyl, an unsubstituted ethylcarbonyl, an unsubstituted propylcarbonyl, or an unsubstituted butylcarbonyl. In other embodiments, R$_3$ is an optionally substituted (cycloaliphatic)carbonyl. For example, R$_3$ is a monocyclic (cycloaliphatic)carbonyl or a bicyclic (cycloaliphatic)carbonyl, each of which is optionally substituted. In other examples. R$_3$ is a cyclopropylcarbonyl, a cyclobutylcarbonyl, a cyclopentlycarbonyl, or a cyclohexylcarbonyl, each of which is optionally substituted with 1-3 of R$^{Z3}$. For example, R$_3$ is an unsubstituted cyclopropylcarbonyl, an unsubstituted cyclobutylcarbonyl, an unsubstituted cyclopentlycarbonyl, or an unsubstituted cyclohexylcarbonyl.

In several embodiments, R$_3$ is an optionally substituted aliphatic. For example, R$_3$ is a methyl, ethyl, propyl, isopropyl, butyl, tert-butyl, isobutyl, or pentyl, each of which is optionally substituted with 1-3 of R$^{Z3}$, wherein each R$^{Z3}$ is independently selected from halo, hydroxy, cyano, acyl, amino, amido, aryl, and cycloaliphatic. In additional examples, R$_3$ is an unsubstituted methyl, ethyl, propyl, isopropyl, butyl, tert-butyl, isobutyl, or pentyl.

In several embodiments, R$_3$ is an (aliphatic)sulfonyl, a (cycloaliphatic)sulfonyl, or an (aryl)sulfonyl, each of which is optionally substituted. For example, R$_3$ is an (alkyl)sulfonyl, an (alkenyl)sulfonyl, or an (alkynyl)sulfonyl, each of which is optionally substituted. In several additional examples, R$_3$ is a (methyl)sulfonyl, an (ethyl)sulfonyl, a (propyl)sulfonyl, a (butyl)sulfonyl, or a (pentyl)sulfonyl, each of which is optionally substituted with 1-3 of R$^{Z3}$. In additional examples, R$_3$ is an unsubstituted (methyl)sulfonyl, an unsubstituted (ethyl)sulfonyl, or an unsubstituted (propyl)sulfonyl. In other examples, R$_3$ is an optionally substituted (aryl)sulfonyl. For example, R$_3$ is an optionally substituted monocyclic arylsulfonyl or an optionally substituted bicyclic arylsulfonyl. In several examples, R$_3$ is a (phenyl)sulfonyl optionally substituted with 1-3 of R$^{Z3}$, wherein each R$^{Z3}$ is independently selected from halo, hydroxy, cyano, amino, amido, acyl, alkoxy, aliphatic, cycloaliphatic, heterocycloaliphatic, aryl, and heteroaryl.

In several embodiments, R$_3$ is hydrogen.

In several embodiments, R$_3$ is one selected from (propyl(amino))carbonyl; methylcarbonyl; (methoxy)carbonyl; N,N-(dimethyl(amino))carbonyl; (cyclohexyl)carbonyl; (isopropyl)carbonyl; (ethyl)carbonyl; hydrogen; methyl; ethyl; (methyl)sulfonyl; propyl; and 4-(trifluoro(methyl(phenyl)))sulfonyl.

4. Substituent R$_{3C}$:

R$_{3C}$ is hydrogen, or R$_{3C}$ and R$_3$ together with the atoms to which they are attached form an optionally substituted 5-6 membered heterocycloaliphatic.

In several embodiments, R$_{3C}$ and R$_3$ together with the atoms to which they are attached form a 5-6 membered heterocycloaliphatic that is optionally substituted with 1-2 of 1-2 of halo, oxo, oxime, acyl, amino, amido, or aliphatic, cycloaliphatic, aryl, heteroaryl, or combinations thereof.

C. Sub-generic Compounds

Another aspect of the present invention provides methods of selectively modulating an M$_1$ muscarinic receptor comprising contacting said receptor with a compound of formula II:

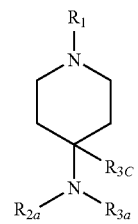

or a pharmaceutically acceptable salt thereof, wherein R$_1$ is defined above in formula I.

R$_{2a}$ is -Z$^G$R$_{10}$, wherein Z$^G$ is independently a bond or an optionally substituted straight or branched C$_{1-5}$ aliphatic chain. Each R$_{10}$ is independently R$^G$, halo, —OH, —CN, —CF$_3$, or —OCH$_3$. Each R$^G$ is independently an aryl, a cycloaliphatic, a heteroaryl, or an aliphatic, each of which is optionally substituted with 1-3 of R$^{Z4}$; and each R$^{Z4}$ is independently selected from oxo, oxime, halo, haloaliphatic, unsubstituted aliphatic, unsubstituted (aliphatic)carbonyl, unsubstituted (aliphatic)amino, and unsubstituted alkoxy.

R$_{3a}$ is -Z$^H$R$_{11}$, wherein Z$^H$ is a bond, —(CH$_2$)$_n$—, —C(O)—, —S(O)$_2$—, —C(O)NH—, or —C(O)O— and R$_{11}$ is an optionally substituted aliphatic, or an optionally substituted aryl; and n is 1-8.

R$_{3C}$ is hydrogen, or R$_{3C}$ and R$_{3a}$ together with the atoms to which they are attached form an optionally substituted 5-6 membered heterocycloaliphatic.

Generally, a compound of formula II has an EC$_{50}$ or a percent efficacy on the M$_1$ receptor lower than its EC$_{50}$ or percent efficacy on the M$_2$, M$_3$, M$_4$, and M$_5$ receptors. The "percent efficacy" of a given compound as an agonist for one of the M$_1$-M$_5$ receptors is defined as the maximum agonist response obtained when treating a given muscarinic cell line with increasing amounts of a compound compared to the maximum agonist response obtained by treating the same cell line with nonselective, full agonist carbachol (used as a reference and always considered 100%).

In several preferable embodiments, a compound of formula II has an EC$_{50}$ on the M$_1$ receptor that is at least about 3 times lower (more potent) than the EC$_{50}$ on any of the M$_2$, M$_3$, M$_4$, and M$_5$ muscarinic receptors, or it has at least about 15% lower level of efficacy on the M$_2$, M$_3$, M$_4$, and M$_5$ muscarinic receptors. In several embodiments, a compound of formula II has an EC$_{50}$ on the M$_1$ receptor that is at least about 10 times lower than the EC$_{50}$ on the M$_2$, M$_3$, M$_4$ and M$_5$ receptors, or it has a level of percent efficacy that is at least 40% less than the percent efficacy on the M$_2$, M$_3$, M$_4$, and M$_5$ muscarinic receptors. In several embodiments, a compound of formula II has an EC$_{50}$ on the M$_1$ receptor from about 3 times to about 745 times less than its $EC_{50}$ on the $M_2$ receptor. In several embodiments, a compound of formula II has an $EC_{50}$ on the $M_1$ receptor from about 3 times to about 520 times less than its $EC_{50}$ on the $M_3$ receptor. In other examples, a compound of formula II has an $EC_{50}$ on the $M_1$ receptor from about 3 times to about 520 times less than its $EC_{50}$ on the $M_4$ receptor. In other embodiments, a compound of formula II has a percent efficacy on the $M_1$ receptor from about 25% to about 95% less that its percent efficacy on the $M_2$ receptor. In additional embodiments, a compound of formula II has a percent efficacy on the $M_1$ receptor from about 20% to about 95% less that its percent efficacy on the $M_3$ receptor. In still other embodiments, a compound of formula II has a percent efficacy on the $M_1$ receptor from about 20% to about 90% less that its percent efficacy on the $M_4$ receptor.

Another aspect of the present invention provides compounds useful for modulating the activity of a muscarinic receptor, described as formula III:

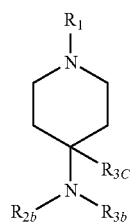

III or a pharmaceutically acceptable salt thereof, wherein $R_1$ is defined above in formula I.

$R_{2b}$ is -$Z^I R_{12}$, wherein $Z^I$ is a bond or an optionally substituted straight or branched $C_{1-5}$ aliphatic chain and $R_{12}$ is an aryl, a cycloaliphatic, a heteroaryl, or an aliphatic, each of which is optionally substituted with 1-3 of $R^{Z6}$. Each $R^{Z6}$ is independently selected from halo, aliphatic, and alkoxy.

$R_{3b}$ is -$Z^J R_{13}$, wherein $Z^J$ is —$(CH_2)_n$—, —$C(O)$—, —$S(O)_2$—, —$C(O)NH$—, or —$C(O)O$—, and $R_{13}$ is hydrogen or an optionally substituted aliphatic, or an optionally substituted aryl; and n is 1-8.

However, in several embodiments, only one of $R_{2b}$ and $R_{3b}$ includes an optionally substituted aryl or an optionally substituted heteroaryl. In other embodiments, when $Z^A$ is a bond, and $R_4$ is a substituted piperidine-4-yl; then $R_4$ is substituted with 1-3 of halo, hydroxy, cyano, or optionally substituted aliphatic, optionally substituted cycloaliphatic, optionally substituted aryl, optionally substituted heteroaryl, or combinations thereof. In still other embodiments, when $Z^I$ is a bond and $R_{12}$ is a phenyl, $R_{12}$ is optionally substituted with 1-3 of halo, unsubstituted aliphatic, haloaliphatic, alkoxy, or combinations thereof.

$R_{3C}$ is hydrogen, or $R_{3C}$ and $R_{3a}$ together with the atoms to which they are attached form an optionally substituted 5-6 membered heterocycloaliphatic.

1. Substituent $R_{2b}$:

$R_{2b}$ is -$Z^I R_{12}$, wherein $Z^I$ is a bond or an optionally substituted straight or branched $C_{1-5}$ aliphatic chain and $R_{12}$ is an aryl, a cycloaliphatic, a heteroaryl, or an aliphatic, each of which is optionally substituted with 1-3 of $R^{Z6}$. Each $R^{Z6}$ is independently selected from halo, aliphatic, and alkoxy.

In several embodiments, $R_{2b}$ is an optionally substituted aryl. For example, $R_{2b}$ is a monocyclic aryl or a bicyclic aryl, each of which is optionally substituted. In additional examples, $R_{2b}$ is a phenyl optionally substituted with 1-5 of $R^{Z6}$, wherein each $R^{Z6}$ is independently selected from halo, aliphatic, and alkoxy. In other examples, $R_{2b}$ is an unsubstituted phenyl.

In several embodiments, $R_{2b}$ is an optionally substituted $C_{1-5}$ aliphatic. In several embodiments. $R_{2b}$ is a methyl, ethyl, propyl, isopropyl, butyl, tert-butyl, isobutyl, or pentyl, each of which is optionally substituted. In several examples, $R_{2b}$ is a methyl or an ethyl, each of which is optionally substituted with 1-3 of $R^{Z6}$, wherein each $R^{Z6}$ is independently selected from halo, aliphatic, 3-alkoxy, and 4-alkoxy. In other examples, $R_{2b}$ is a methyl optionally substituted with aryl or cycloaliphatic. In additional examples, $R_{2b}$ is an unsubstituted propyl, isopropyl, butyl, tert-butyl, isobutyl, or pentyl.

In several embodiments, $R_{2b}$ is an optionally substituted cycloaliphatic. For example, $R_{2b}$ is a monocyclic cycloaliphathic or a bicyclic cycloaliphatic, each of which is optionally substituted. In several examples, $R_{2b}$ is a monocyclic cycloaliphatic, such as cyclopropyl, cyclobutyl, cyclopentyl, or cyclohexyl, each of which is optionally substituted with 1-3 of $R^{Z6}$. In several examples, $R_{2b}$ is an unsubstituted cyclopropyl, cyclobutyl, cyclopentyl, or cyclohexyl.

In several embodiments, $R_{2b}$ is an optionally substituted heteroaryl. For example, $R_{2b}$ is a monocyclic heteroaryl or a bicyclic heteroaryl, each of which is optionally substituted. In several examples, $R_{2b}$ is an indole-yl; isoindole-yl; 3H-indole-yl; indoline-yl; benzo[b]furan-yl; benzo[b]thiophene-yl; benzimidazole-yl; benzthiazole-yl; purine-yl; quinoline-yl; isoquinoline-yl; cinnoline-yl; phthalazine-yl; quinazoline-yl; quinoxaline-yl; furanyl; thiophene-yl; thiazole-yl; pyridine-yl; pyrimidine-yl; pyrazine-yl; or 1,3,5-triazine-yl, each of which is optionally substituted with 1-3 of $R^{Z6}$.

In several embodiments, $R_{2b}$ is one selected from 4-fluorophenyl; phenyl; 2-fluorophenyl; phenylmethyl; 3-fluorophenyl; 4-methylphenyl; 3-methylphenyl; 3,4-dimethylphenyl; 3-methoxyphenyl; 4-methoxyphenyl; 4-(tert-butyl)phenyl; 3-chlorophenyl; 3-methoxycarbonyl; 4-chlorophenyl; cyclohexane-yl; 2,4-difluorophenyl; isopropyl; cyclopentane-yl; cyclobutane-yl; propyl; 2-chloro-4-methyl-pyrimidine-6-yl; and isobutyl.

2. Substituent $R_{3b}$:

$R_{3b}$ is -$Z^J R_{13}$, wherein $Z^J$ is —$(CH_2)_n$—, —$C(O)$—, —$S(O)_2$—, —$C(O)NH$—, or —$C(O)O$—, and $R_{13}$ is hydrogen or an optionally substituted aliphatic, or an optionally substituted aryl; and n is 1-8.

In several embodiments, $R_{3b}$ is an acyl group such as optionally substituted (aliphatic)carbonyl. For example, $R_{3b}$ is an (alkyl)carbonyl, an (alkenyl)carbonyl, or an (alkynyl)carbonyl; each of which is optionally substituted. In several examples, $R_{3b}$ is a methylcarbonyl, an ethylcarbonyl, a propylcarbonyl, or a butylcarbonyl; each of which is optionally substituted. In several examples, $R_{3b}$ is an unsubstituted methylcarbonyl, an unsubstituted ethylcarbonyl, an unsubstituted propylcarbonyl, or an unsubstituted butylcarbonyl.

In several embodiments, $R_{3b}$ is an optionally substituted aliphatic. For example, $R_{3b}$ is a methyl, ethyl, propyl, isopropyl, butyl, tert-butyl, isobutyl, or pentyl, each of which is optionally substituted. In additional examples, $R_{3b}$ is an unsubstituted methyl, ethyl, propyl, isopropyl, butyl, tert-butyl, isobutyl, or pentyl.

In several embodiments, $R_{3b}$ is an (aliphatic)sulfonyl, or an (aryl)sulfonyl, each of which is optionally substituted. For example, $R_{3b}$ is an (alkyl)sulfonyl, an (alkenyl)sulfonyl, or an (alkynyl)sulfonyl, each of which is optionally substituted with 1-3 of $R^{Z5}$(defined above in formula II). In several embodiments, $R_{3b}$ is an (alkyl)sulfonyl, an (alkenyl)sulfonyl, or an (alkynyl)sulfonyl, each of which is optionally substituted wherein each $R^{Z5}$, wherein each $R^{Z5}$ is independently selected from halo, hydroxy, cyano, amino, amido, acyl, alkoxy, aliphatic, cycloaliphatic, heterocycloaliphatic, aryl, and heteroaryl. In several additional examples, $R_{3b}$ is a (methyl)sulfonyl, an (ethyl)sulfonyl, a (propyl)sulfonyl, a (butyl)sulfonyl, or a (pentyl)sulfonyl, each of which is optionally substituted with 1-3 of $R^{Z5}$. In additional examples, $R_{3b}$ is an unsubstituted (methyl)sulfonyl, an unsubstituted (ethyl)sulfonyl, or an unsubstituted (propyl)sulfonyl. In other examples, $R_{3b}$ is an optionally substituted (aryl)sulfonyl. For example, $R_{3b}$ is an optionally substituted monocyclic arylsulfonyl or an optionally substituted bicyclic arylsulfonyl. In several examples, $R_{3b}$ is a (phenyl)sulfonyl optionally substituted with 1-3 of $R^{Z5}$.

In several embodiments, $R_{3b}$ is one selected from (propyl(amino))carbonyl; methylcarbonyl; (methoxy)carbonyl; (isopropyl)carbonyl; (ethyl)carbonyl; methyl; ethyl; (methyl)sulfonyl; propyl; and 4-(trifluoro(methyl(phenyl)))sulfonyl.

C. Exemplary Compounds

Exemplary compounds of the present invention include, but are not limited to, those illustrated in Table 1 below.

TABLE I

Exemplary compounds of formulae I, II, and III.

1

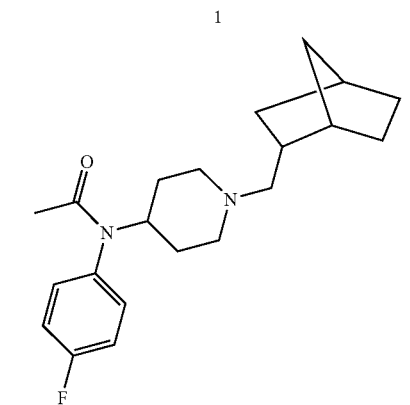

2

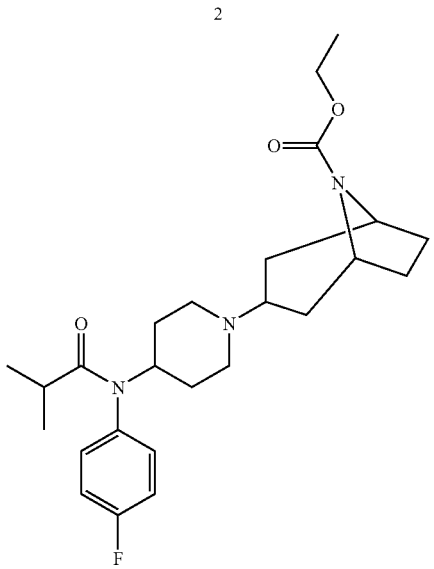

TABLE I-continued

Exemplary compounds of formulae I, II, and III.

3

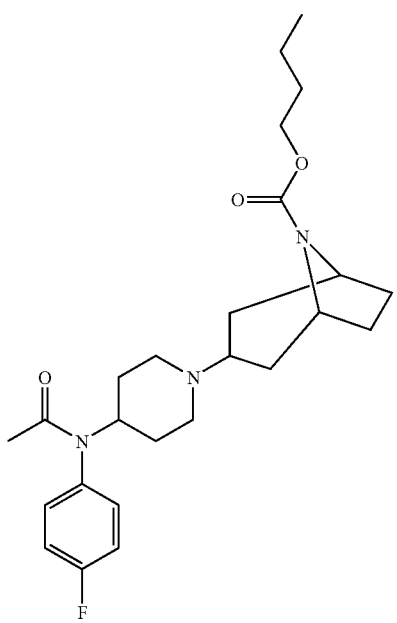

4

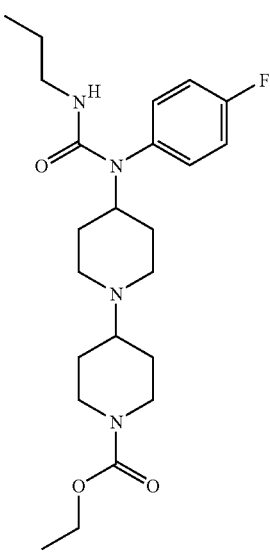

TABLE I-continued
Exemplary compounds of formulae I, II, and III.
5
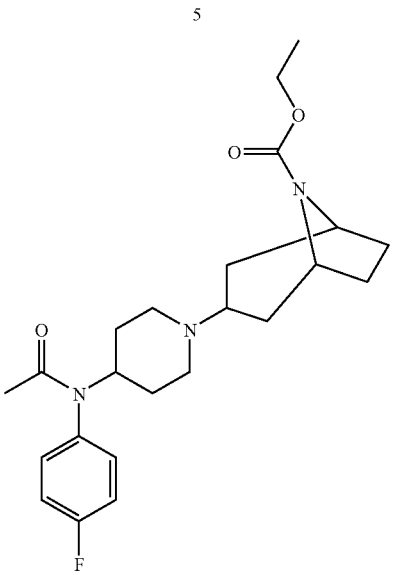
6
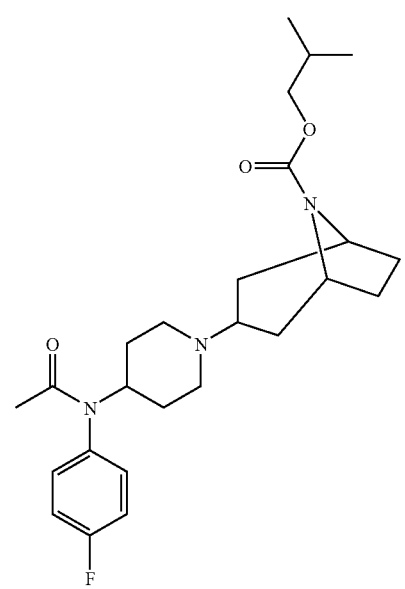
TABLE I-continued
Exemplary compounds of formulae I, II, and III.
7
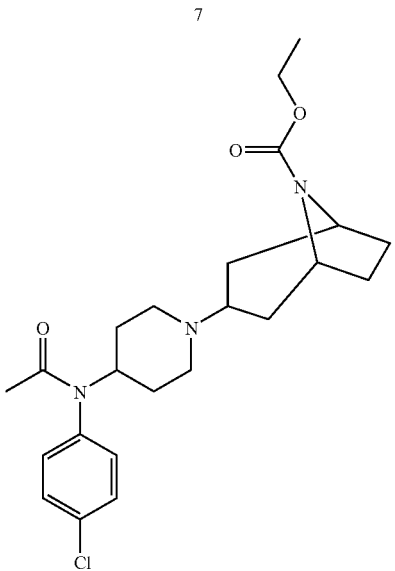
8
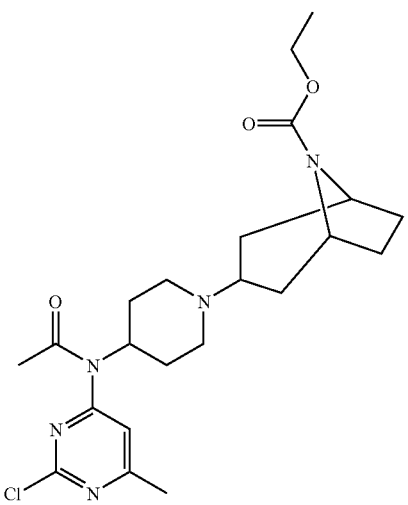

TABLE I-continued
Exemplary compounds of formulae I, II, and III.
9
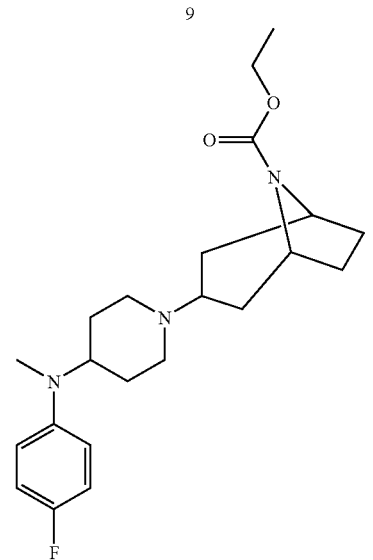
10
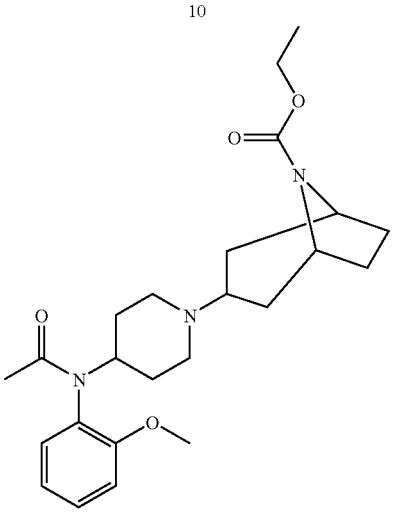
11
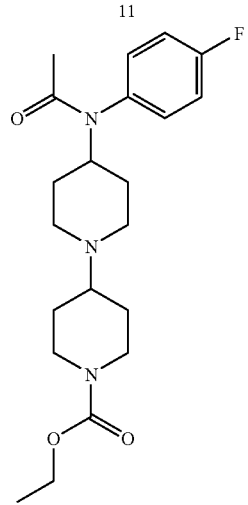
TABLE I-continued
Exemplary compounds of formulae I, II, and III.
12
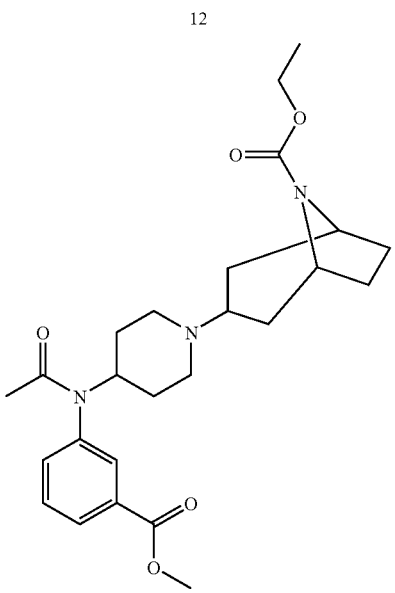
13
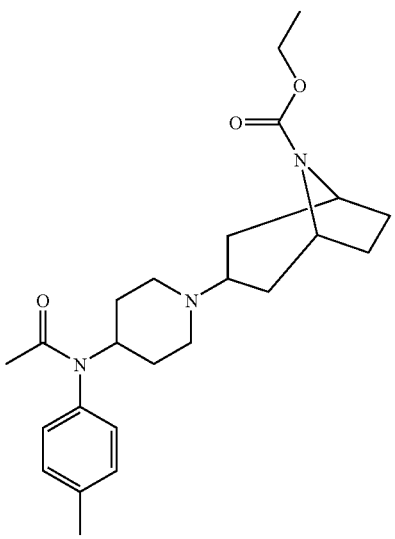

TABLE I-continued
Exemplary compounds of formulae I, II, and III.
14
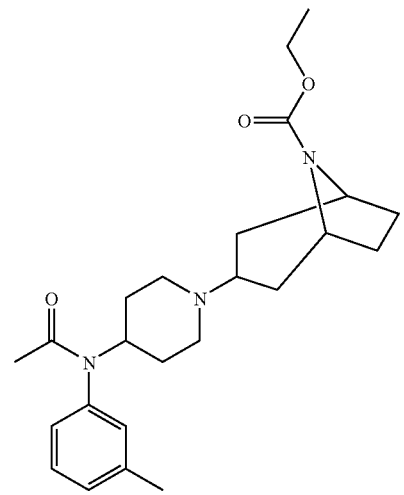
15
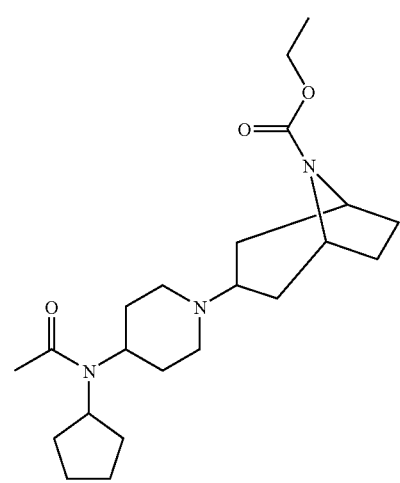
TABLE I-continued
Exemplary compounds of formulae I, II, and III.
16
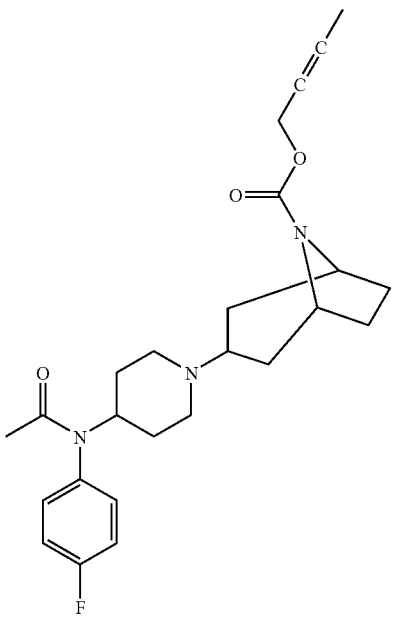
17
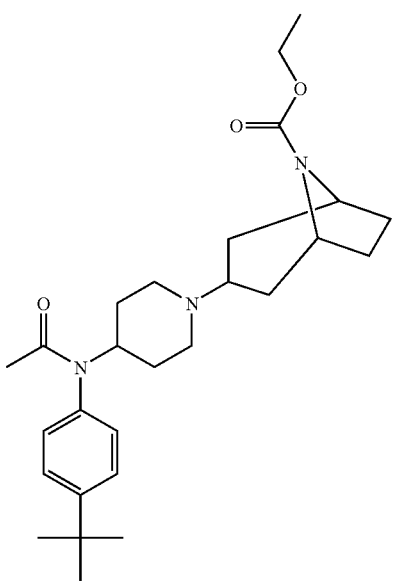

TABLE I-continued
Exemplary compounds of formulae I, II, and III.
18
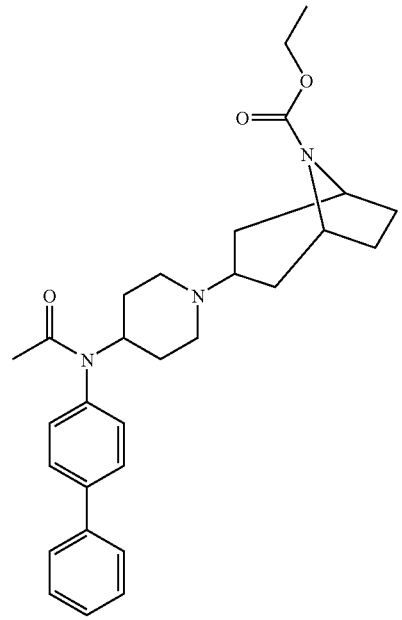
19
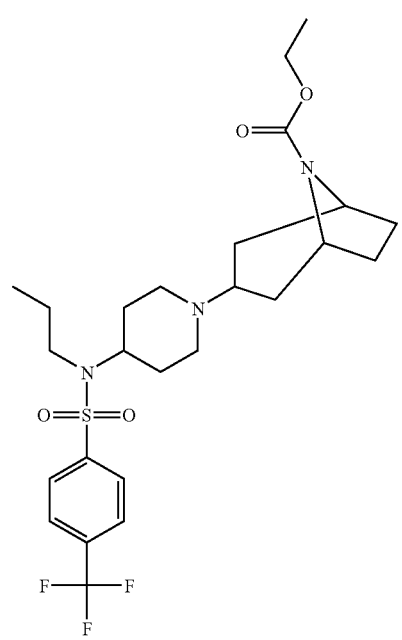
TABLE I-continued
Exemplary compounds of formulae I, II, and III.
20
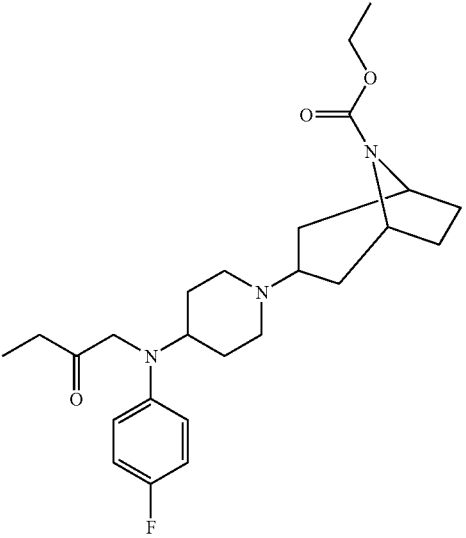
21
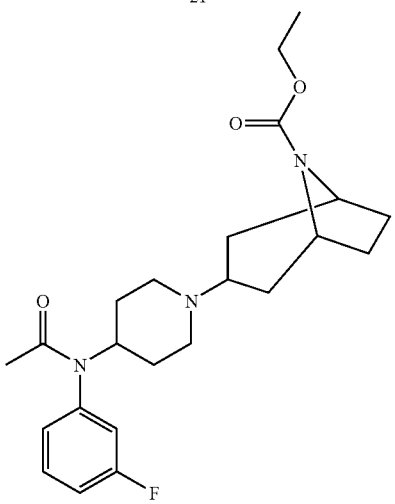
22
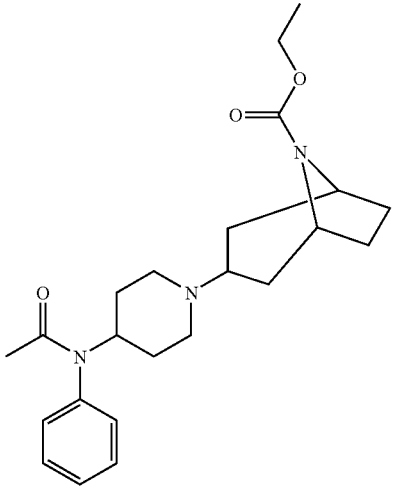

TABLE I-continued
Exemplary compounds of formulae I, II, and III.
23
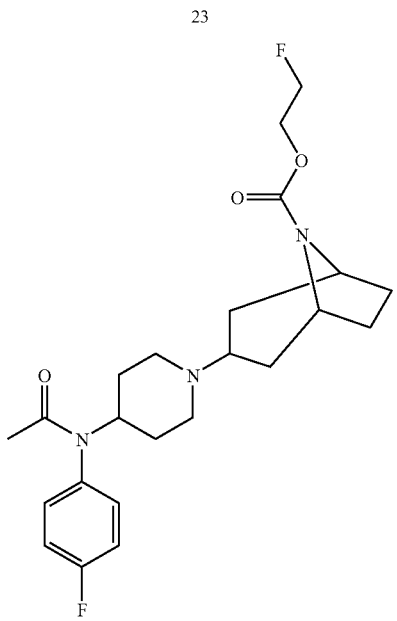
24
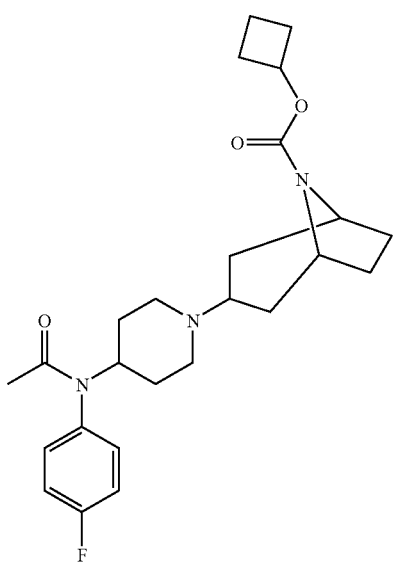
TABLE I-continued
Exemplary compounds of formulae I, II, and III.
25
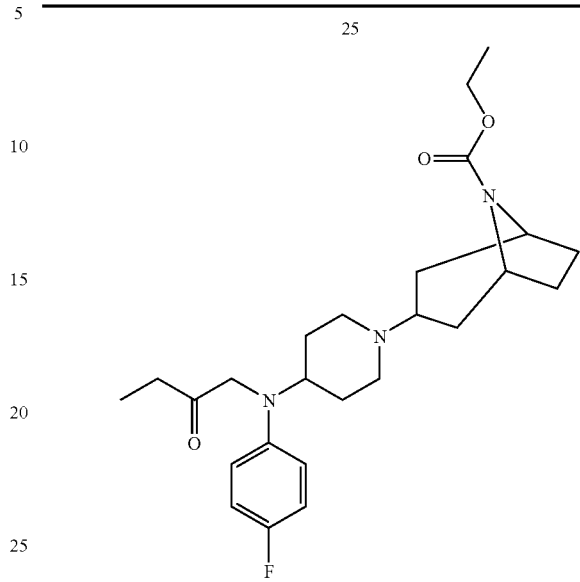
26
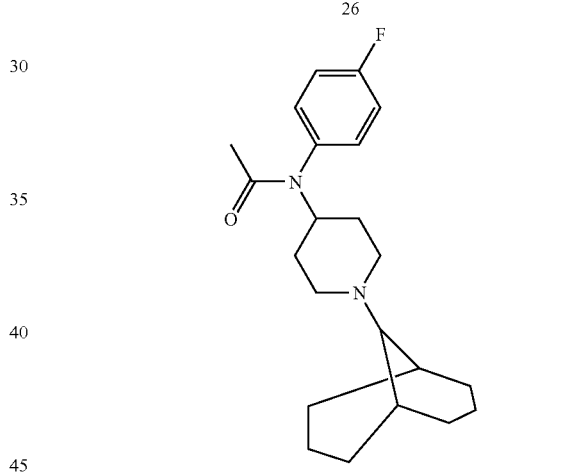
27
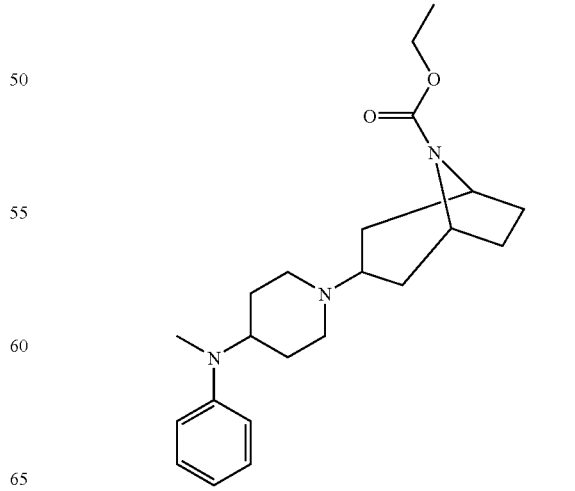

TABLE I-continued
Exemplary compounds of formulae I, II, and III.
28
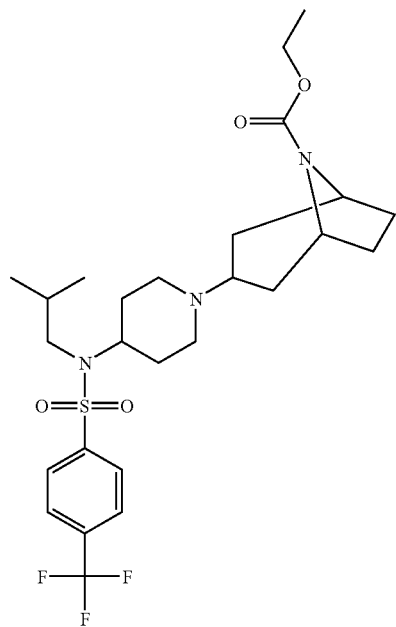
29
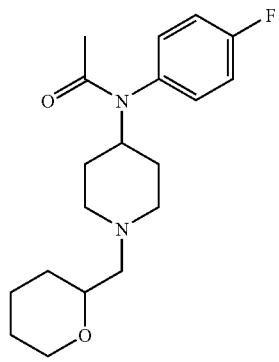
30
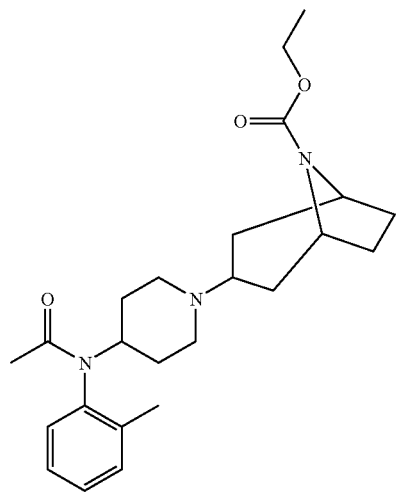
TABLE I-continued
Exemplary compounds of formulae I, II, and III.
31
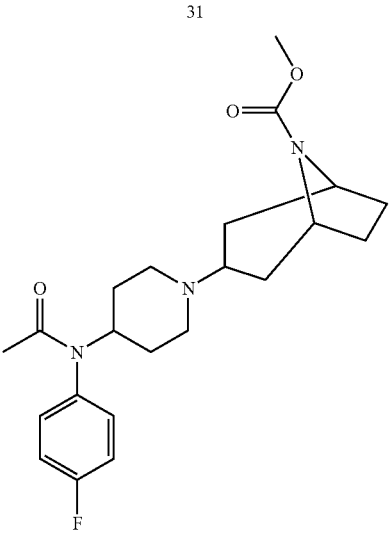
32
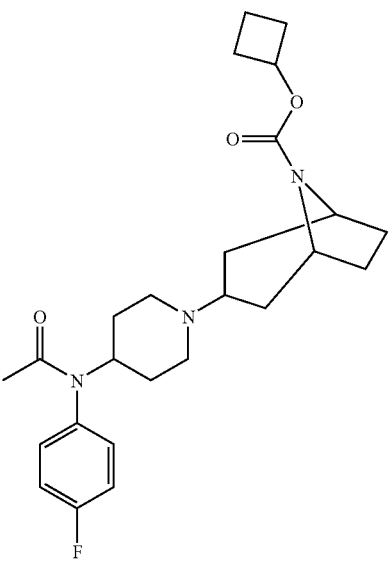
33
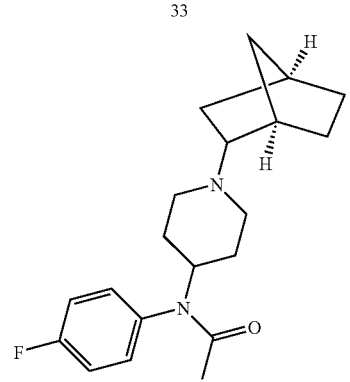

TABLE I-continued
Exemplary compounds of formulae I, II, and III.
34
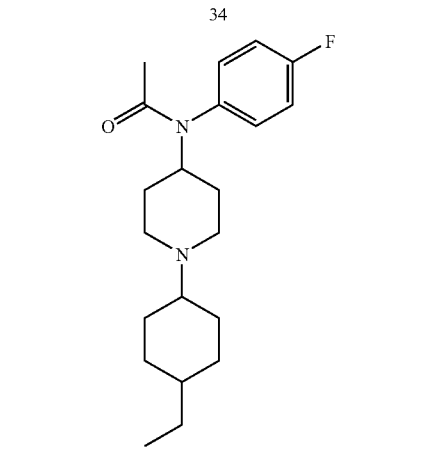
35
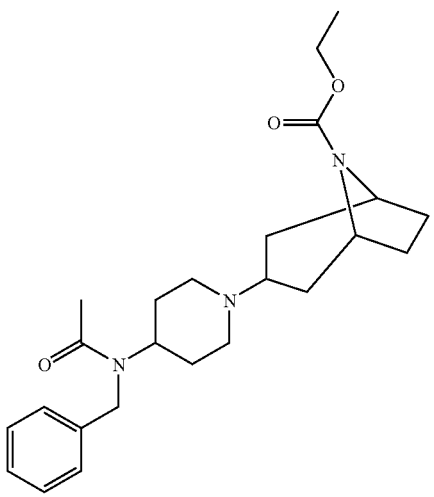
36
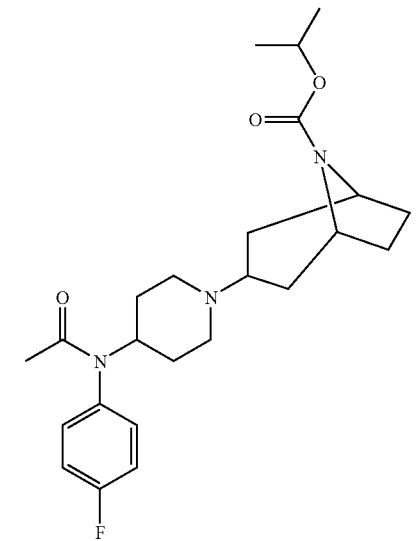
TABLE I-continued
Exemplary compounds of formulae I, II, and III.
37
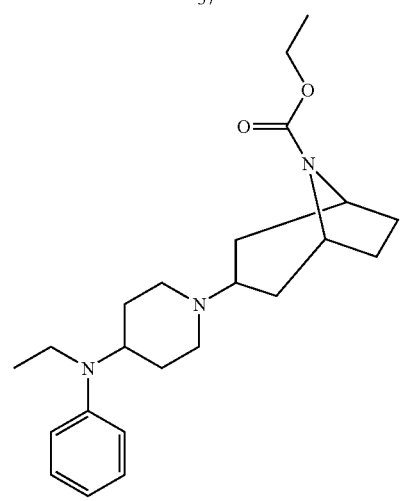
38
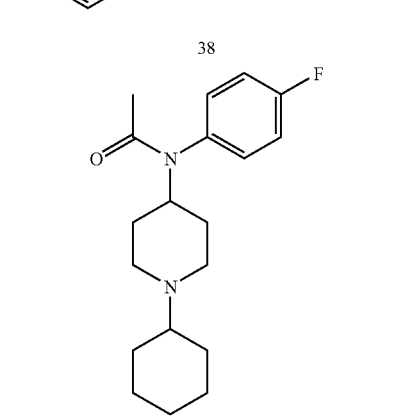
39
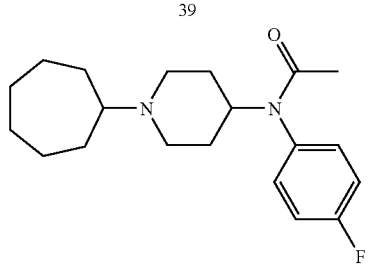
40
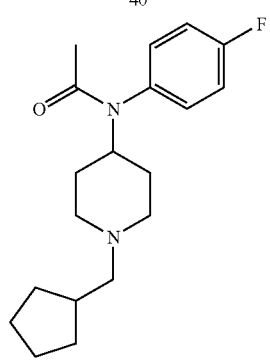

TABLE I-continued
Exemplary compounds of formulae I, II, and III.
41
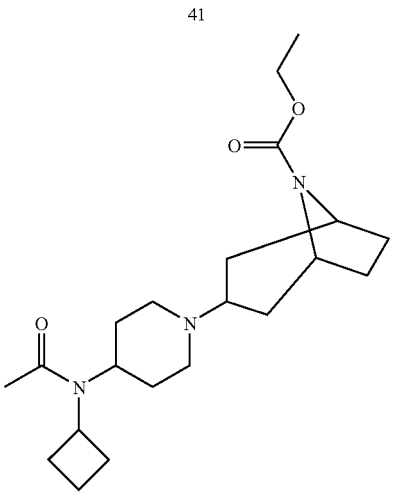
42
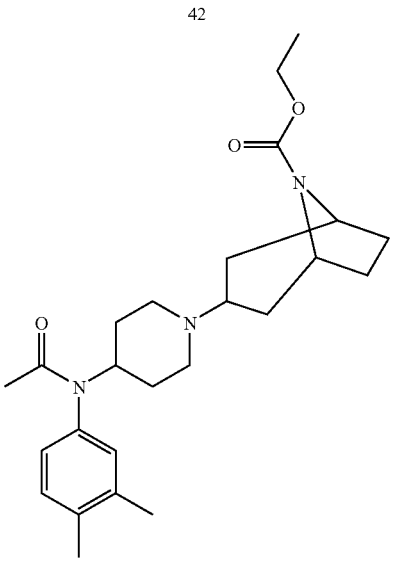
43
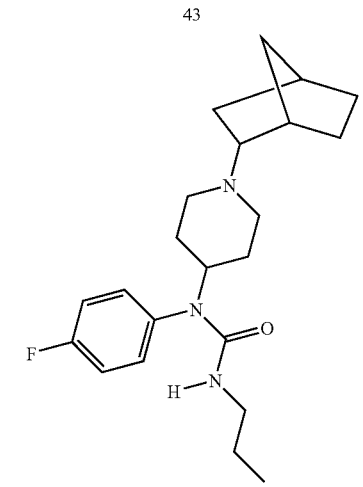
TABLE I-continued
Exemplary compounds of formulae I, II, and III.
44
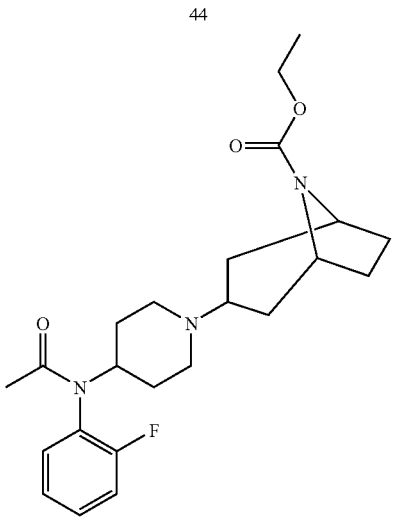
45
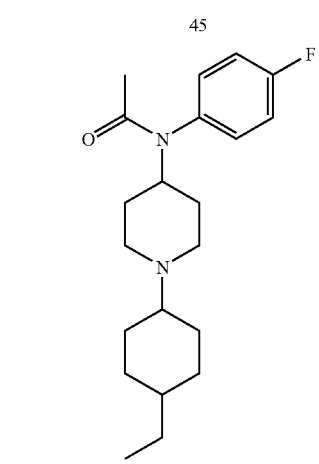
46
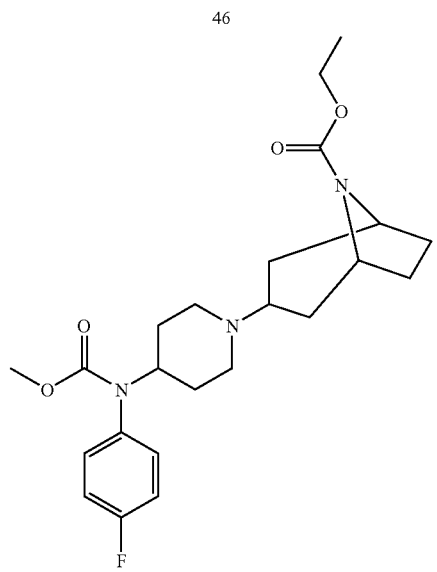

TABLE I-continued
Exemplary compounds of formulae I, II, and III.
47
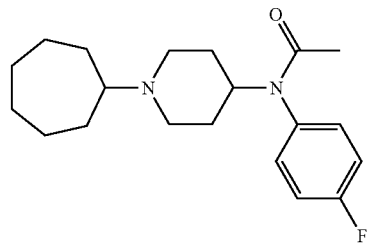
48
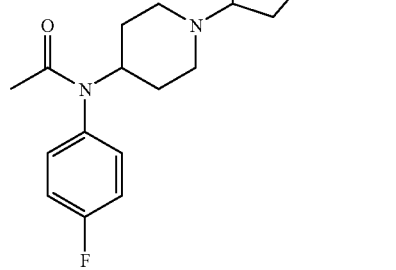
49
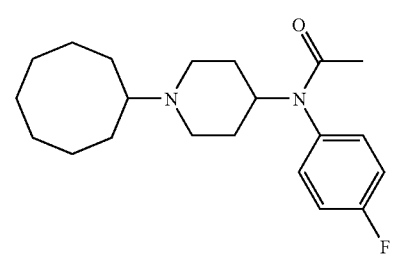
TABLE I-continued
Exemplary compounds of formulae I, II, and III.
50
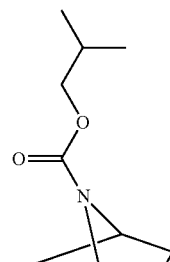
51
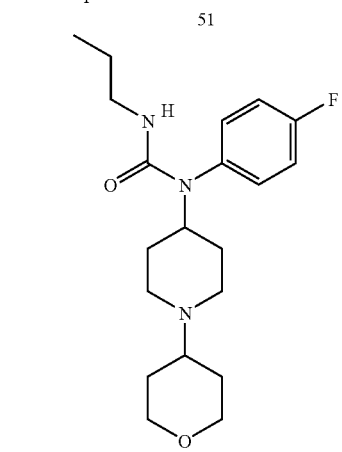
52
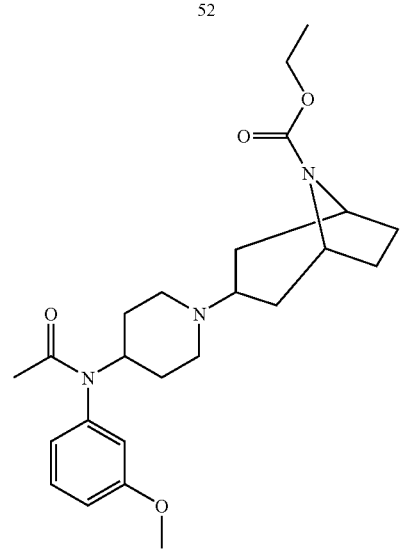

TABLE I-continued
Exemplary compounds of formulae I, II, and III.
53
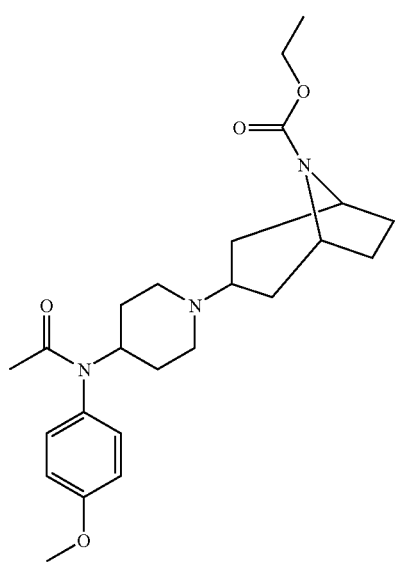
54
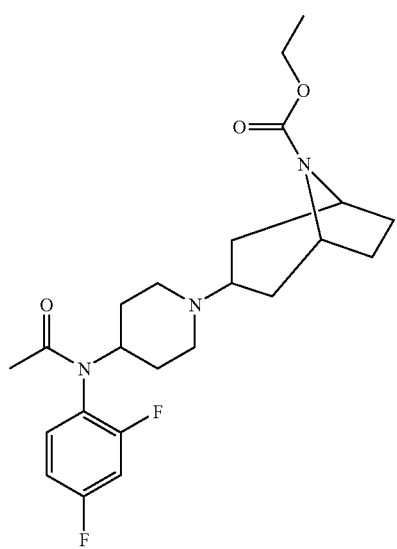
TABLE I-continued
Exemplary compounds of formulae I, II, and III.
55
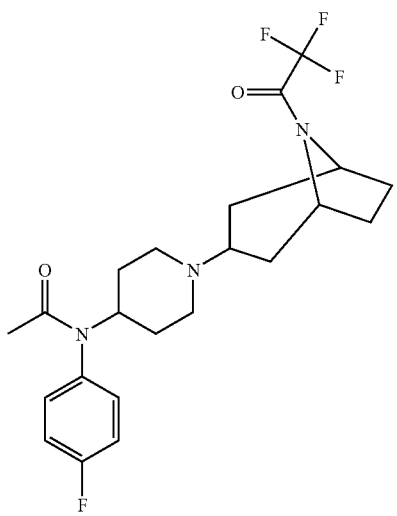
56
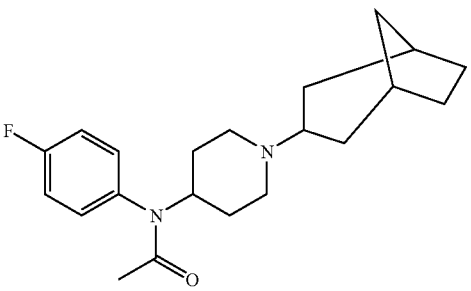
57
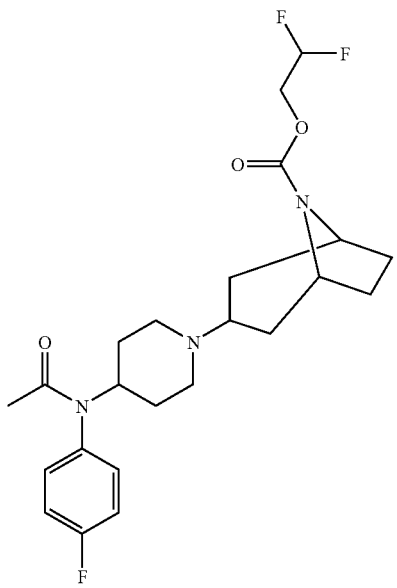

TABLE I-continued
Exemplary compounds of formulae I, II, and III.
58
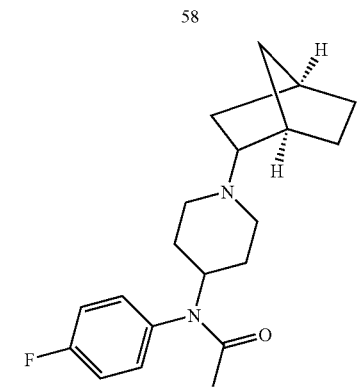
59
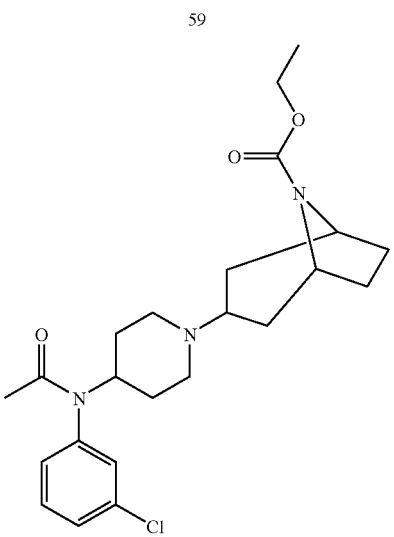
60
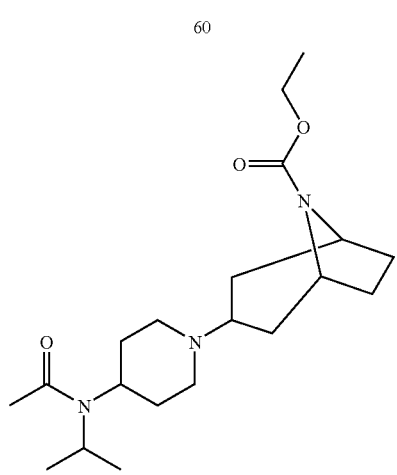
TABLE I-continued
Exemplary compounds of formulae I, II, and III.
61
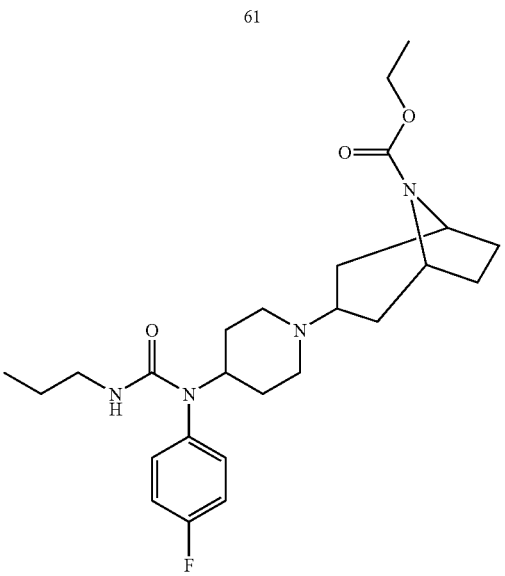
62
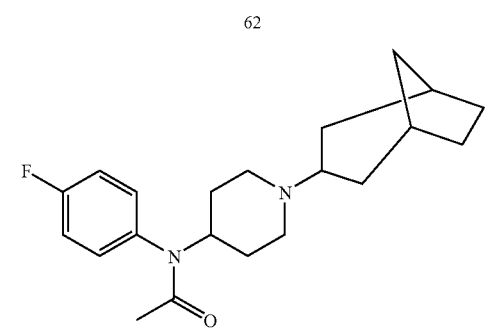
63
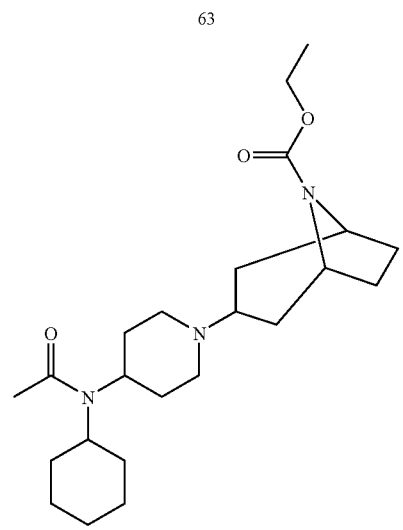

TABLE I-continued
Exemplary compounds of formulae I, II, and III.
64
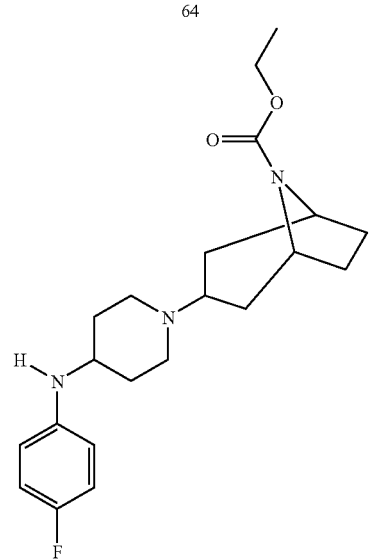
65
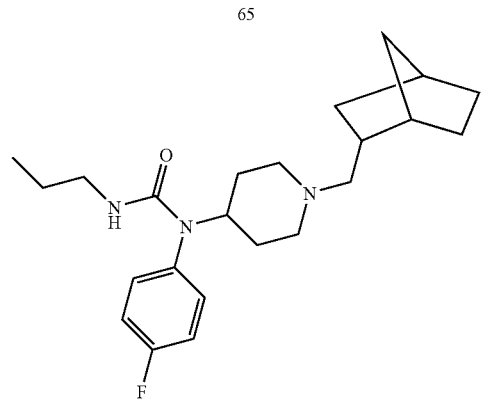
66
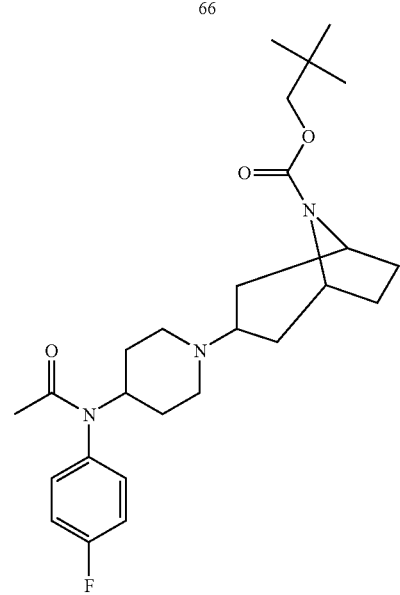
TABLE I-continued
Exemplary compounds of formulae I, II, and III.
67
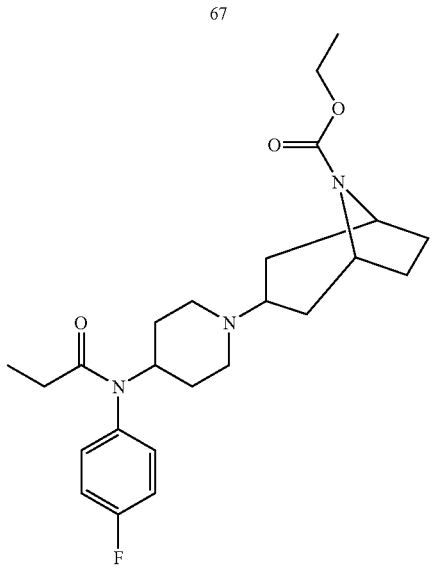
68
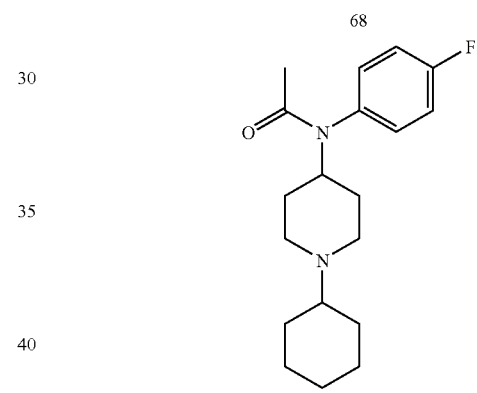
69
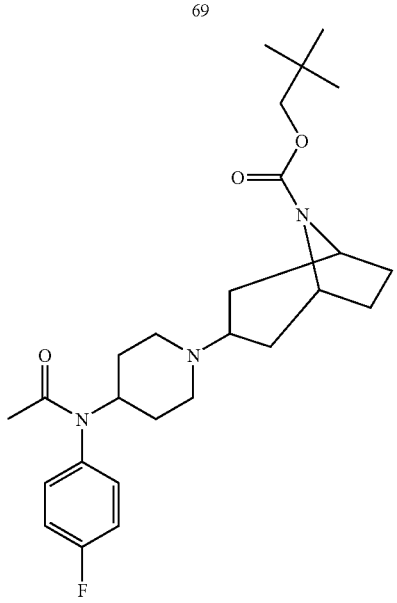

TABLE I-continued
Exemplary compounds of formulae I, II, and III.
70
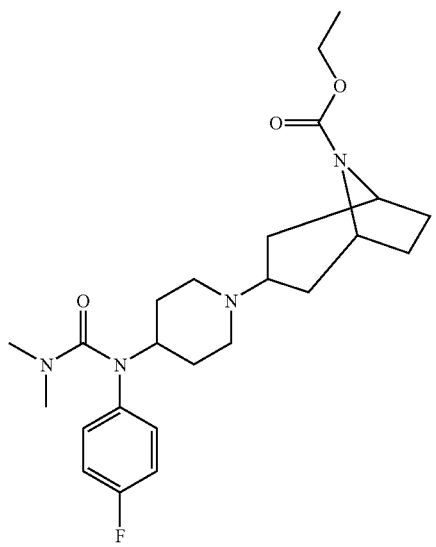
72
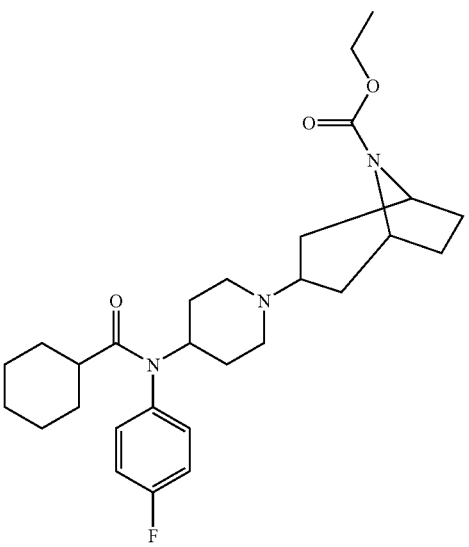
71
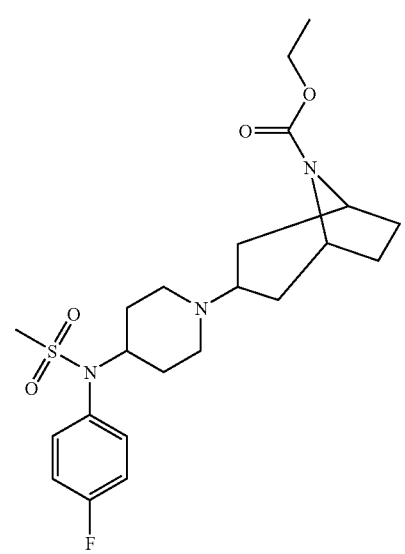
73
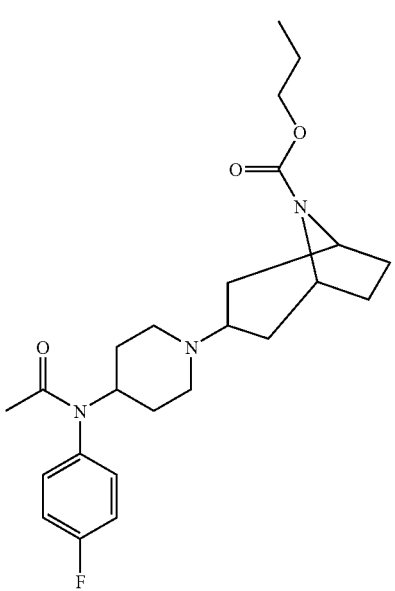

TABLE I-continued
Exemplary compounds of formulae I, II, and III.
74
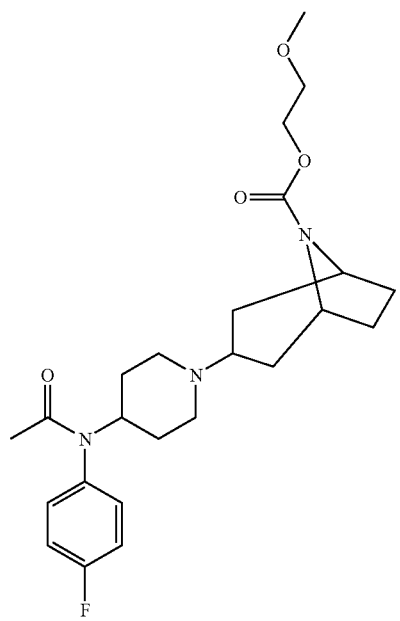
75
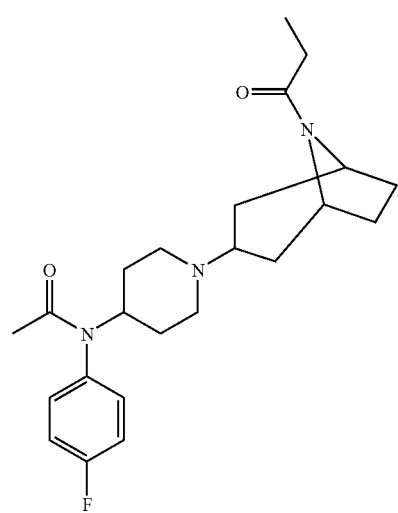
TABLE I-continued
Exemplary compounds of formulae I, II, and III.
76
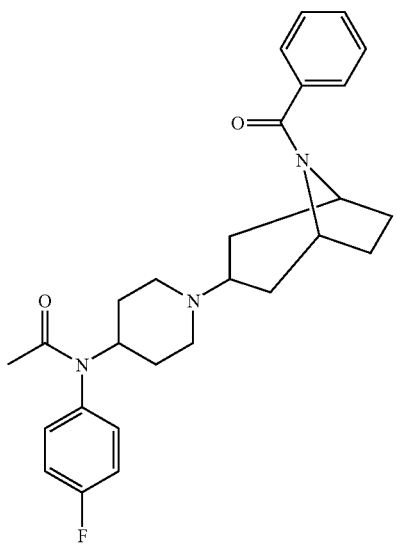
77
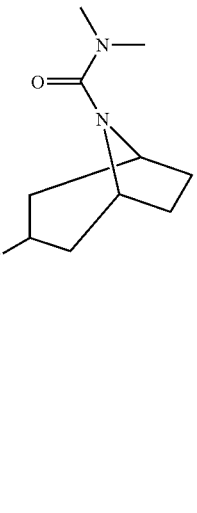

TABLE I-continued
Exemplary compounds of formulae I, II, and III.
78
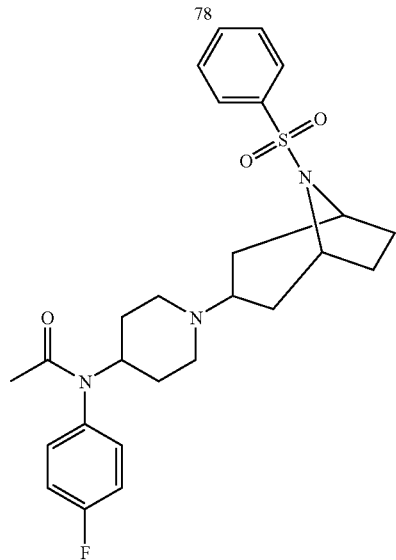
79
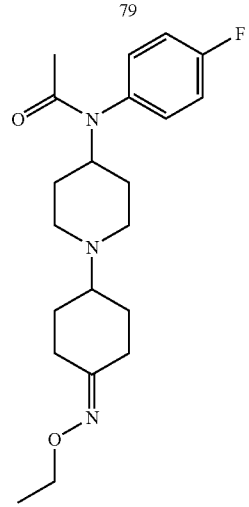
80
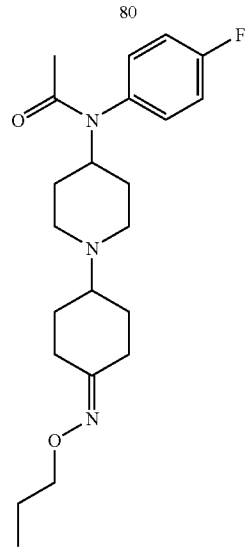
TABLE I-continued
Exemplary compounds of formulae I, II, and III.
81
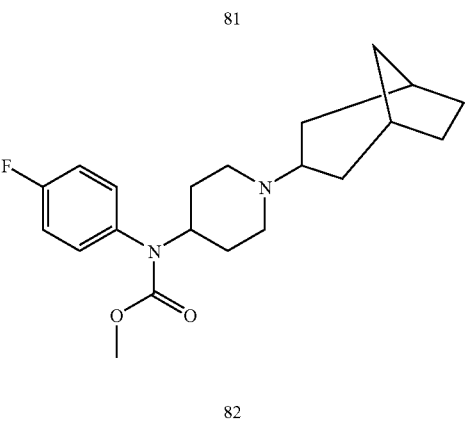
82
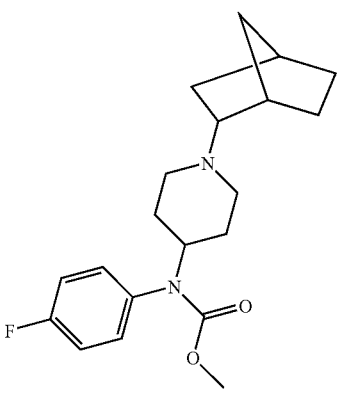
83
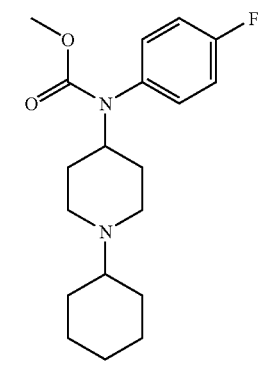

TABLE I-continued

Exemplary compounds of formulae I, II, and III.

84

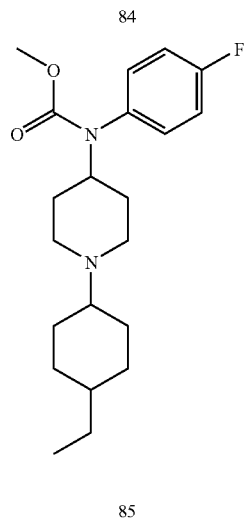

85

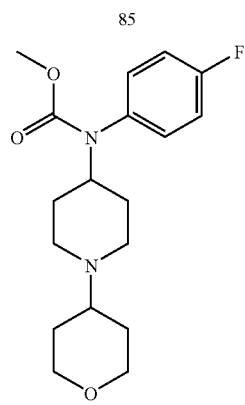

86

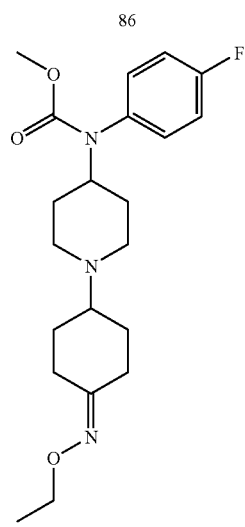

TABLE I-continued

Exemplary compounds of formulae I, II, and III.

87

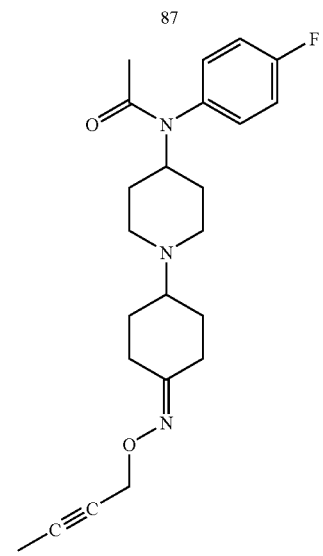

88

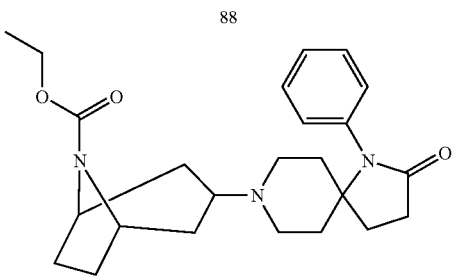

89

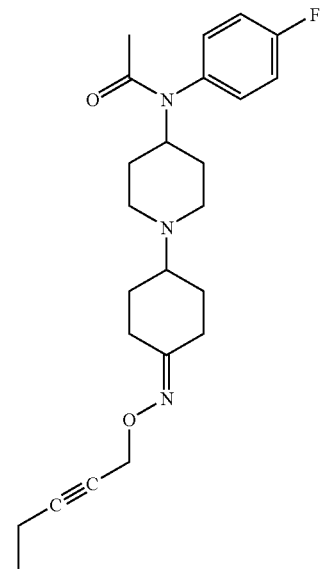

III. Synthetic Schemes

The compounds of formulae (I, II, and III) may be readily synthesized from commercially available or known starting materials by known methods. Exemplary synthetic routes to produce compounds of formulae (I, II, and III) are provided below in Schemes 1-3 below. In schemes 1-3 below, for simplicity, $R_{3C}$ is hydrogen.

Scheme 1 below depicts general conditions useful for synthesizing compounds of formula I.

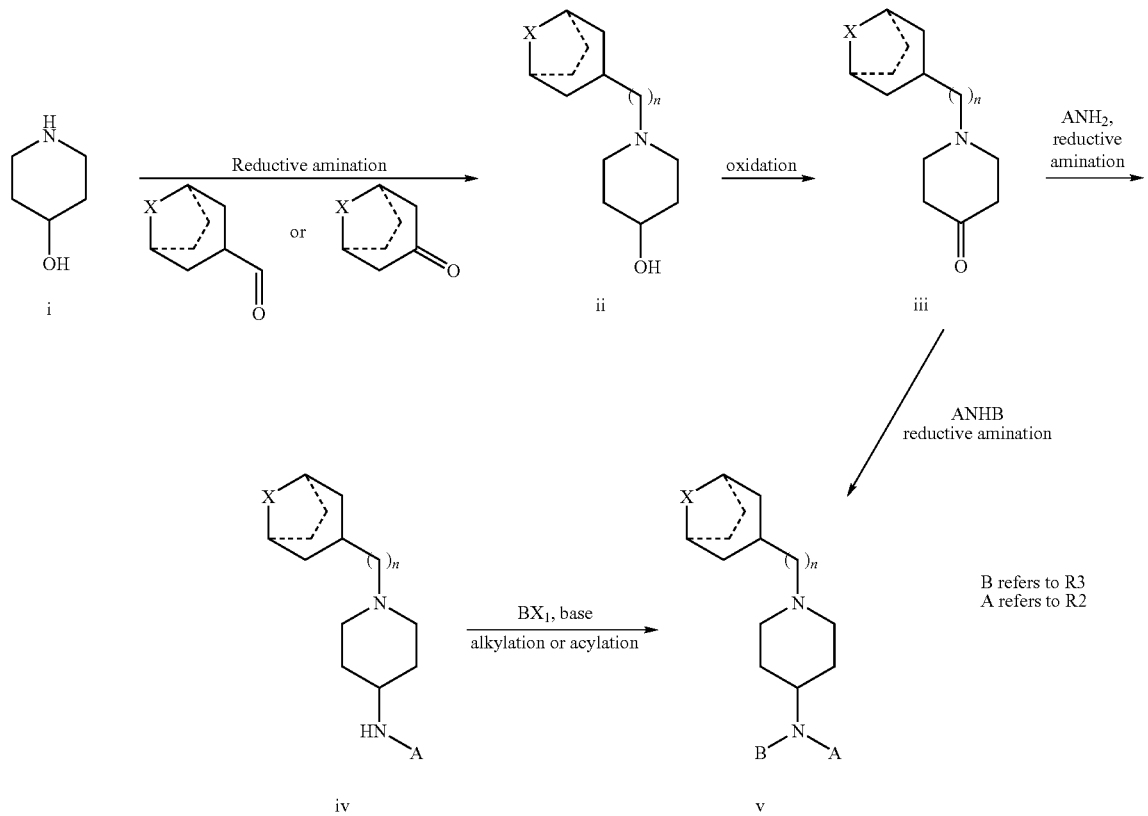

The reaction of piperidine-4-ol (i) with an appropriate aldehyde or ketone under reductive amination conditions (e.g., NaBH(OAc)$_3$ in DCE/AcOH/TEA at room temperature) may be used to provide the desired compounds of formula (ii). In other embodiments, compounds of formula (ii) are produced by reacting the piperidine-4-ol (i) and a ketone in a neat solution of Ti(OiPr)$_4$, followed by treatment with NaBH$_4$ in MeOH. See Abdel-Magid, A. F. et al., "Reductive Amination of Aldehydes and Ketones with Sodium Triacetoxyborohydride. Studies on Direct and Indirect Reductive Amination Procedures," J. Org. Chem., 61, pp. 3849-3862 (1996) and the references cited therein.

Oxidation of the resulting piperidine-4-ol to the corresponding piperidine-4-one (iii) can be accomplished by a variety of known oxidizing reagents such as Swern, PDC, and KMnO$_4$.

Treatment of compounds (iii) with primary aliphatic or aromatic amines, e.g., A$_1$NH$_2$ where A$_1$ is an aliphatic or aryl group, under reductive amination conditions (see above) leads to the formation of compounds (iv). Compound (iv) can be subjected to a variety of standard alkylation and acylation conditions. In some embodiments, the compounds of formula (Iv) are alkylated, such as with alkyl halide/K$_2$CO$_3$ and alkyl halide/Hunig's base, to provide compounds of formula I, where B is alkyl, cycloalkyl or heteroalkyl. In other embodiments, the compounds of formula I can be prepared directly from the compounds of formula (iii), by reductive amination with the appropriate secondary amines ANHB. In still other embodiments, the compounds of formula (Iv) can be acylated, such as with acyl chloride/Et$_3$N, acyl anhydride/ DMAP, or isocyanate/Et$_3$N n-BuLi/chloroformate, to prepare compounds of formula I where B is acetamide, sulfonamide, urea, carbamate.

In another embodiment, compounds of formula I may be prepared according to scheme 2.

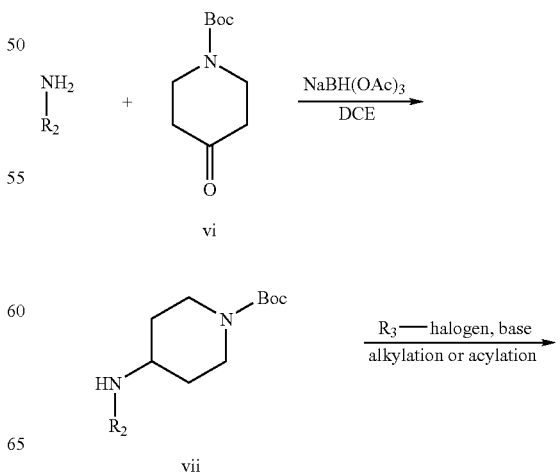

-continued

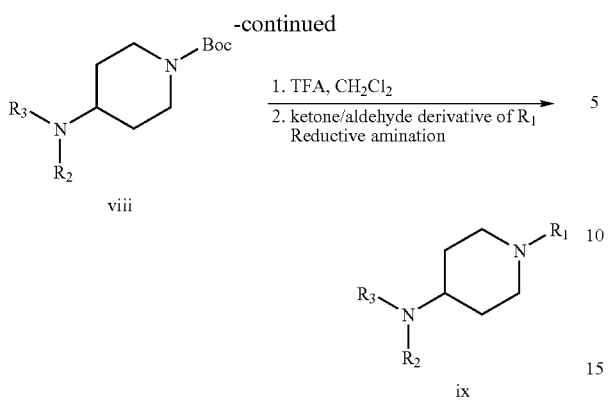

viii ix

The reaction of N-Boc-piperidine-4-one (vi) with an appropriate amine under reductive amination conditions as described above may be used to provide compounds of formula vii. Removal of the Boc protecting group under standard conditions, such as treatment with trifluoroacetic acid in $CH_2Cl_2$, followed by reductive amination between the resulting free amine and a ketone or aldehyde of choice provide the compounds of formula ix.

In still further embodiments, the compound of formula I, such as when $R_2$ is a heteroaryl, may be produced via Scheme 3.

Scheme 3:

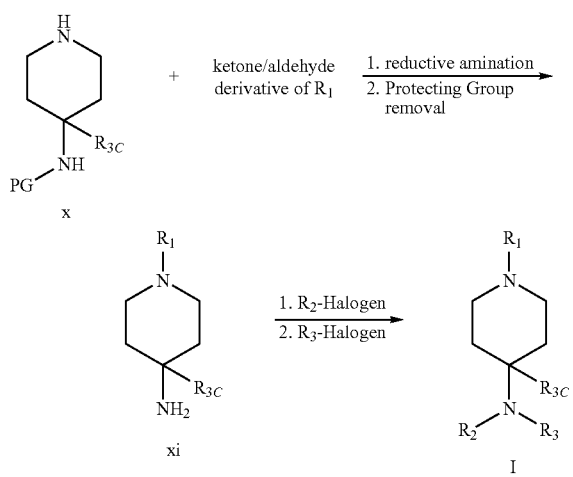

x xi

I

The 4-amino piperidine x can be coupled with the desired ketone or aldehyde under a variety of reductive amination conditions (for examples the reactions described herein). After removal of the protective group, the primary amine reacts with the desired aryl halide, under appropriate conditions such as $K_2CO_3$/DMF, $Cu(OAc)_2$/$K_2CO_3$/DMF, $PdTFA_2$/$P^tBu_3$/$K_3PO_4$, etc. See Hartwig, J. F et al, "Scope and Mechanism of Palladium-Catalyzed Amination of Five-Membered Heterocyclic Halides", *J. Org. Chem.*, 2003, 68, 2861, Bagley, J. R. "New 4-(heteroanilido)piperidines, Structurally Related to the Pure Opioid Agonist Fentanyl, with Agonist and/or Antagonist Properties", *J. Med. Chem.* 1989, 32, 663 and references cited therein.

The resulting secondary amine is then optionally alkylated or acylated with a suitable agent under known conditions to provide compounds of formula I.

In embodiments wherein $R_{3C}$ and $R_3$ together with the atoms to they are attached form an optionally substituted 5-6 membered heterocycloaliphatic the compounds may be prepared by known methods such as, for example, those described in U.S. Pat. No. 6,956,042.

IV. Formulations Administrations, and Uses

A. Pharmaceutically Acceptable Compositions

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono-or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, II, and III) are selective modulators of $M_1$, $M_2$ and $M_4$. More preferably, the compounds of formulae (I, II, and III) are selective modulators of $M_1$ and/or $M_4$. Yet more preferably, certain compounds of formulae (I, II, and III) are selective modulators of $M_1$. Or, preferably, certain compounds of formulae (I, II, and III) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e. an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_1$ agonist" means a compound that has a measurably greater ability to act as an $M_1$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, II, and III), or an embodiment thereof as set forth herein.

According to another embodiment, the present invention provides a method of treating a disease mediated by a muscarinic receptor including the step of administering to said mammal a composition comprising a compound of formulae (I, II, and III), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease. All references cited within this document are incorporated herein by reference.

IV. Preparations and Examples

In order that the invention described therein may be more fully understood, the following examples are set forth. It should be understood that these examples are for illustrative purposes only and are not to be construed as limiting this invention in any manner.

Mass spectroscopy samples were analyzed on a MicroMass ZQ or Quattro II mass spectrometer operated in single MS mode with electrospray ionization. Samples were introduced into the mass spectrometer using chromatography, using Zorbax SB C18 column, 3.0×150 mm. Flow rate: 1.0 mL/minute. Detection: 254 & 214 nm. Mobile phase for all mass spectroscopy analysis consisted of acetonitrile-water mixtures with 0.2% formic acid as a modifier using 10-90% acetonitrile and water gradient. As used herein, the term "$R_t$" refers to the HPLC retention time, in minutes, associated with the compound. HPLC purification refers to C-18 reverse phase using Gilson instrument, YMC combiprep ProC18 column, 20×100 mm. Flow rate is 20 ml/minute. Mobile phase consisted of water with 0.1% TFA and acetonitrile with 0.1% TFA. Running time is 10 minutes.

Example 1 ethyl 3-(4-((4-fluorophenyl)(methoxycarbonyl)amino)piperidin-1-yl)-8-azabicyclo[3.2.1]octane-8-carboxylate (Compound No. 46)

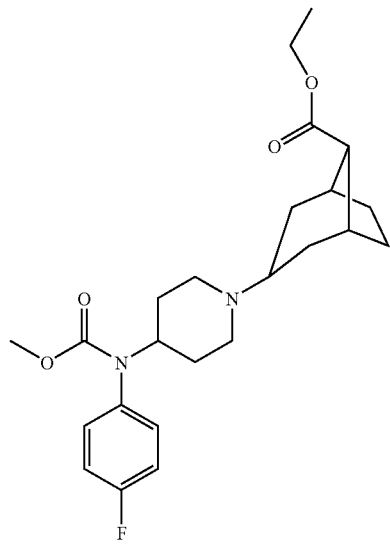

Compound No. 46

Step 1: Preparation of 3-(4-Hydroxy-piperidin-1-yl)-8-azabicyclo[3.2.1]octane-8-carboxylic acid ethyl ester (1a)

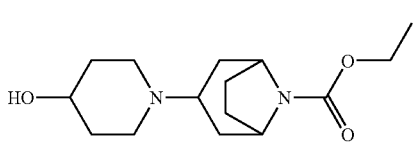

N-Carboethoxytropinone (8.0 g; 40.56 mmol; 1.2 eq.) and 4-hydroxypiperidine (3.4 g; 33.80 mmol; 1 eq.) were dissolved in DCM (50 mL) and DCE (50 mL). Ti(OiPr)$_4$ (29.9 mL; 101.4 mmol; 3 eq.) was then added and the reaction was stirred at room temperature for 72 hours. The solution was cooled to −78° C. and treated with MeOH (100 mL). After 15 minutes at −78° C., NaBH$_4$ (6.1 g; 162 mmol; 4 eq.) was slowly added and the reaction stirred for 30 minutes at −78° C. and then slowly warmed to room temperature and stirred at room temperature for an additional 1 hour. 1N NaOH (40 mL) was slowly added and the solution was stirred for 30 minutes at room temperature (white solid precipitates were formed). The solution was filtered through a pad of Celite and the precipitate was washed with MeOH (100 mL). The solvent was removed under high vacuum and the crude product was partitioned between EtOAc (100 mL) and 1N HCl (100 mL). The layers were separated, the organic layer was discarded, and the aqueous layer was washed once more with EtOAc (50 mL). The aqueous layer was then slowly basified with NaOH and the alkaline solution was extracted with EtOAc (2×100 mL). The combined organic layers were dried over Na$_2$SO$_4$, filtered, and concentrated under high vacuum to provide the product as an oil that was analytically pure and used without further purification.

LC/MS M/Z 283.2, Retention time=0.54 minutes; 10-99% CH$_3$CN/H$_2$O gradient with 0.05% TFA over 5 minutes.

H NMR (400 MHz, CDCl3) δ 4.34 (d, J=21.4 Hz, 2H), 4.14 (q, J=7.1 Hz, 2H), 3.73-3.67 (m, 1H), 2.82-2.80 (m, 3H), 2.28-2.25 (m, 2H), 1.97-1.90 (m, 4H), 1.74-1.52 (m, 9H), 1.27 (t, J=7.1 Hz, 3H).

Step 2: Preparation of 3-(4-oxo-piperidin-1-yl)-8-aza-bicyclo[3.2.1]octane-8-carboxylic acid ethyl ester (2a)

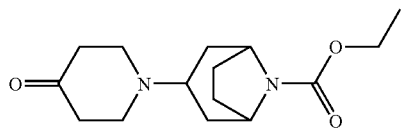

In a 200 mL round bottom flask was added DCM (50 mL) and oxalyl chloride (1.63 mL; 18.72 mmol; 1.2 eq.). The solution was cooled to −78° C. and treated with DMSO (2.65 mL; 37.44 mmol; 2.4 eq.). The solution was stirred at −78° C. for 20 minutes and then treated with the alcohol 1 (4.4 g; 15.6 mmol; 1 eq. dissolved in 20 mL of DCM). The solution was stirred for 30 minutes at −78° C. and then treated with Et3N (6.52 mL; 46.8 mmol; 3 eq.). The solution was stirred at −78° C. for 20 minutes and then slowly warmed to room temperature and stirred at room temperature for an additional 2 hours. The solution was then treated with saturated aqueous NaHCO$_3$ (50 mL) and the layers were separated. The organic layer was washed with brine (50 mL), dried over Na$_2$SO$_4$, filtered, and concentrated under high vacuum to afford the product as an oil which was used without further purification.

LC/MS M/Z 281.1, Retention time=0.87 minutes; 10-99% CH$_3$CN/H$_2$O gradient with 0.05% TFA over 5 minutes.

H NMR (400 MHz, CDCl$_3$) δ 4.36 (d, J=15.1 Hz, 2H), 4.15 (q, J=7.1 Hz, 2H), 3.00 (pentet, J=8.3 Hz, 1H), 2.81 (t, J=6.0 Hz, 4H), 2.43 (t, J=6.0 Hz, 4H), 2.00-1.97 (m, 2H), 1.74-1.64 (m, 6H), 1.27 (t, J=7.1 Hz, 3H).

Step 3: Preparation of 3-[4-(4-Fluoro-phenylamino)-piperidin-1-yl]-8-aza-bicyclo[3.2.1]octane-8-carboxylic acid ethyl ester (Compound No. 64)

Compound No. 64

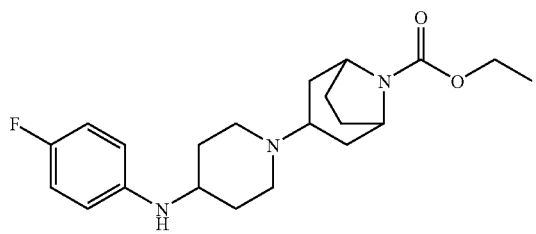

4-Fluoroaniline (0.50 mL; 5.24 mmol; 1 eq.) and the ketone 2 (1.62 g; 5.76 mmol; 1.1 eq.) were dissolved in DCE (10 mL). Acetic acid (0.30 mL; 5.24 mmol; 1.0 eq.) was added followed by the portion-wise addition of NaBH(OAc)$_3$ (1.55 g; 7.33 mmol; 1.4 eq.). The reaction was stirred at room temperature for 24 hours and then quenched with 1N HCl (20 mL). The layers were separated and the organic layer was discarded. The aqueous layer was basified with NaOH and then extracted with EtOAc (2×20 mL). The organic extracts were combined, dried over Na$_2$SO$_4$, filtered, and concentration under reduced pressure to afford 1.60 g of the product. The product was purified using reversed-phase HPLC (2-99% CH3CN/H2O gradient with 0.05% TFA).

LC/MS M/Z 376.2, Retention time=1.94; 10-99% CH$_3$CN/H$_2$O gradient with 0.05% TFA over 5 minutes.

H NMR (400 MHz, DMSO-d6, TFA salt) δ 6.99-6.89 (m, 2H), 6.65-6.58 (m, 2H), 4.25 (s, 2H), 4.07 (q, J=7.0 Hz, 2H), 3.71-3.53 (m, 3H), 3.42-3.33 (m, 1H), 2.97 (q, J=11.0 Hz, 2H), 2.15-1.84 (m, 6H), 1.74-1.60 (m, 4H), 1.55-1.44 (m, 2H), 1.21 (t, J=7.1 Hz, 3H).

Step 4: Preparation of ethyl 3-(4-((4-fluorophenyl)(methoxycarbonyl)amino)piperidin-1-yl)-8-azabicyclo[3.2.1]octane-8-carboxylate The amine 3 (64 mg; 0.17 mmol; 1 eq.) was dissolved in THF (2 mL) and cooled to −78° C. n-BuLi (2.5M in hexane; 0.07 mL; 0.17 mmol; 1 eq.) was added to the solution. After 10 minutes of stirring at −78° C., methyl chloroformate (0.015 mL; 0.2 mmol; 1.1 eq.) was added. The solution was slowly warmed to room temperature and stirred at room temperature for 18 hours (overnight). 1N NaOH (10 mL) was added and the solution was extracted with EtOAc (2×20 mL). The combined organic extracts were dried over Na$_2$SO$_4$, filtered, and concentrated under reduced pressure. The crude product was purified by reversed-phase HPLC (2-99% CH$_3$CN/H$_2$O gradient with 0.05% TFA) to provide the product as a TFA salt.

LC/MS M/Z 434.4, Retention time=1.98; CH$_3$CN/H$_2$O gradient with 0.05% TFA over 5 minutes. H NMR (400 MHz, MeOD, TFA salt) δ 7.23-7.13 (m, 4H), 4.47-4.38 (m, 3H), 4.14 (q, J=7.1 Hz, 2H), 3.72-3.62 (m, 6H), 3.08 (t, J=11.9 Hz, 2H), 2.22-2.00 (m, 6H), 1.79-1.65 (m, 6H), 1.27 (t, J=7.1 Hz, 3H).

Example 2

3-{4-[1-(4-Fluoro-phenyl)-3,3-dimethyl-ureido]-piperidin-1-yl}-8-aza-bicyclo[3.2.1]octane-8-carboxylic acid ethyl ester (Compound No. 70)

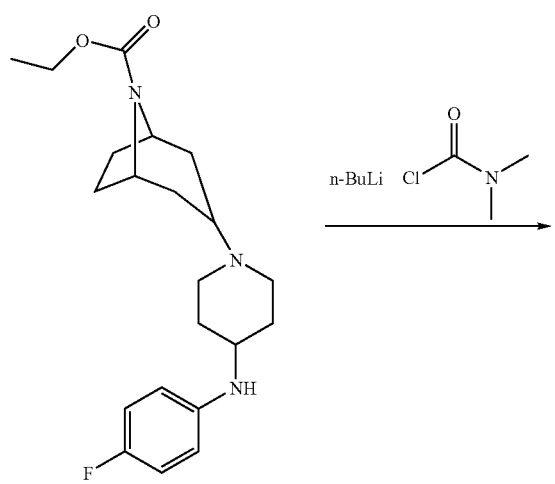

Compound No. 64 n-BuLi

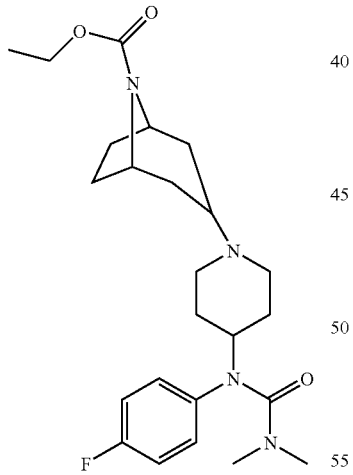

Compound No. 70

The title compound was produced via the methodology described in Example 1, but using dimethylcarbamoyl chloride (0.28 mL; 0.30 mmol; 1.8 eq.) instead of methyl chloroformate.

LC/MS M/Z 447.4, Retention time=2.11; 10-99% CH$_3$CN/H$_2$O gradient with 0.05% TFA over 5 minutes. H NMR (400 MHz, MeOD, TFA salt) δ 7.23-7.13 (m, 4H), 4.40 (s, 2H), 4.15 (q, J=7.1 Hz, 2H), 4.11 (tt, J=12.2 Hz, 3.7 Hz, 1H), 3.71-3.60 (m, 3H), 3.04 (t, J=12.9 Hz, 2H), 2.64 (s, 6H), 2.20-1.81 (m, 8H), 1.82-1.64 (m, 4H), 1.28 (t, J=7.1 Hz, 3H).

Example 3

3-{4-[Cyclohexanecarbonyl-(4-fluoro-phenyl)-amino]-piperidin-1-yl}-8-aza-bicyclo[3.2.1]octane-8-carboxylic acid ethyl ester (Compound No. 72)

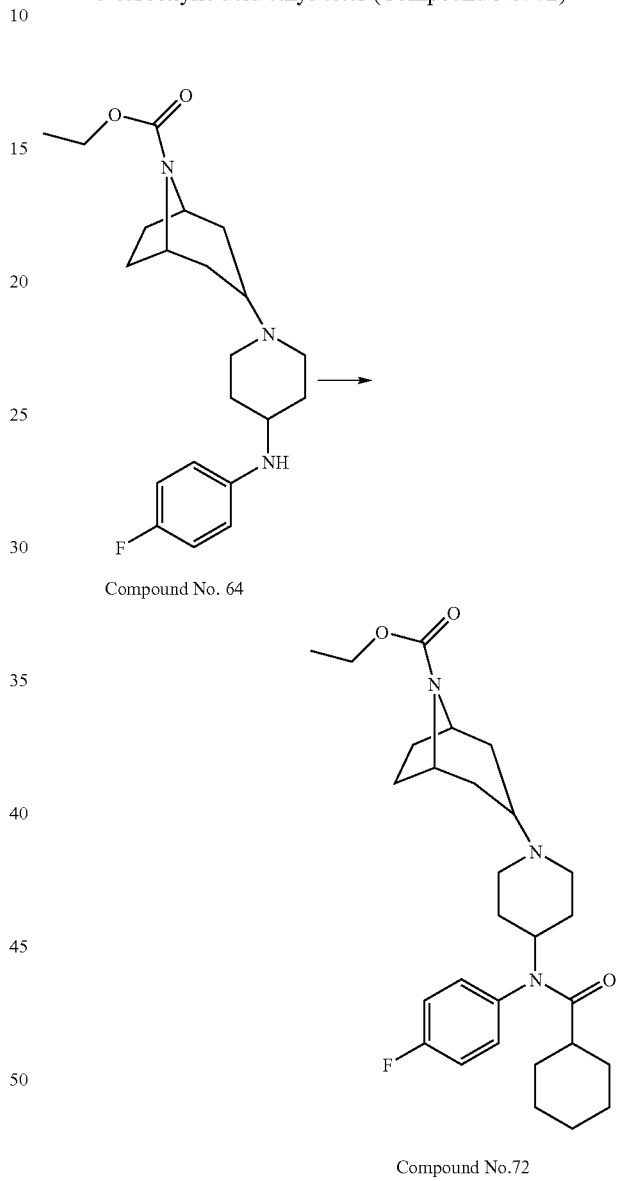

3-[4-(4-Fluoro-phenylamino)-piperidin-1-yl]-8-azabicyclo[3.2.1]octane-8-carboxylic acid ethyl ester (50 mg; 0.13 mmol; 1 eq.) was dissolved in DCM (3 mL) and Et$_3$N (0.056 mL; 0.39 mmol; 3 eq.) was added. Cyclohexylcarbonyl chloride (30 mg; 0.2 mmol; 2 eq.) was then added and the solution was stirred at room temperature for 18 hours (overnight). 1N NaOH (10 mL) was added and the solution was extracted with EtOAc (2×20 mL). The combined organic extracts were dried over Na$_2$SO$_4$, filtered, and concentrated under reduced pressure. The crude product was purified using reversed-phase HPLC (2-99% CH$_3$CN/H$_2$O gradient with 0.05% TFA). LC/MS M/Z=432.4, Retention time=2.12; 10-99% CH$_3$CN/

H$_2$O gradient with 0.05% TFA over 5 minutes. H NMR (400 MHz, MeOD, TFA salt) δ 7.33-7.22 (m, 4H), 4.75 (tt, J=12.3 Hz, 3.8 Hz, 1H), 4.39 (s, 2H), 4.14 (q, J=7.1 Hz, 2H), 3.75-3.58 (m, 3H), 3.09 (t, J=11.9 Hz, 2H), 2.14-1.89 (m, 7H), 1.79-1.40 (m, 14H), 1.27 (t, J=7.1 Hz, 3H), 1.26-1.11 (m, 1H), 1.02-0.90 (m, 2H).

Example 4

3-{4-[(4-Fluoro-phenyl)-methanesulfonyl-amino]-piperidin-1-yl}-8-aza-bicyclo[3.2.1]octane-8-carboxylic acid ethyl ester (Compound No. 71)

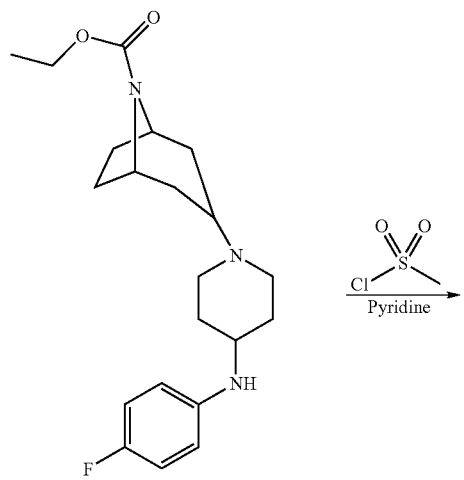

Compound No. 64

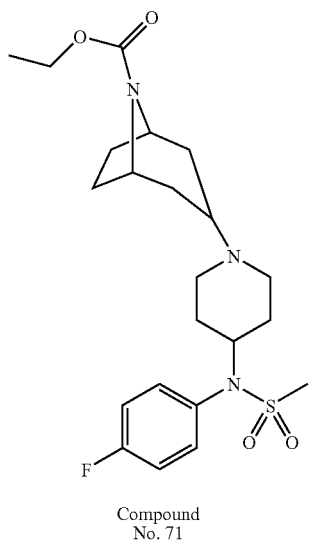

Compound No. 71

3-[4-(4-fluoro-phenylamino)-piperidin-1-yl]-8-aza-bicyclo[3.2.1]octane-8-carboxylic acid ethyl ester (25 mg; 0.07 mmol; 1 eq.) was dissolved in dry prydine (2 mL) and MsCl (19 mg; 2.5 eq.) was added. The reaction mixture was heated to 80° C. and stirred under N$_2$ overnight. The solution was diluted with DCM (10 mL) and washed with saturated NaHCO$_3$ (2×20 mL). The organic layer was dried over Na$_2$SO$_4$, filtered, and concentrated under high vacuum to provide the product as an oil. The crude residue was purified by reversed-phase HPLC (2-99% CH$_3$CN/water gradient with 0.05% TFA). LC/MS M/Z 454.2, Retention time=1.88 minutes; 10-99% CH$_3$CN/H$_2$O gradient with 0.05% TFA.

Example 5

3-[4-(ethyl-phenyl-amino)-piperidin-1-yl]-8-azabicyclo[3.2.1]octane-8-carboxylic acid ethyl ester (Compound No. 37)

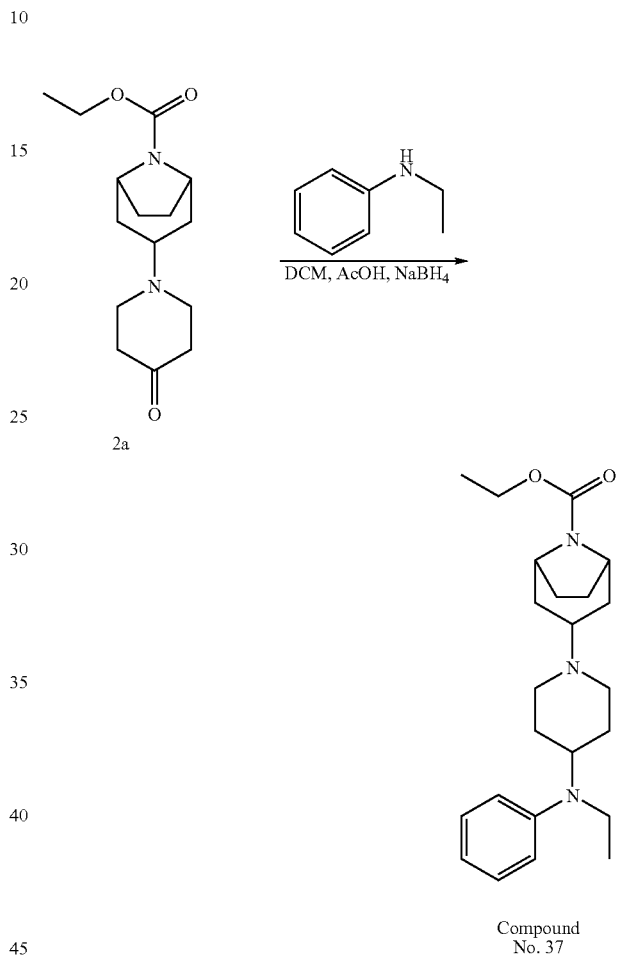

Compound No. 37

3-(4-Oxo-piperidin-1-yl)-8-aza-bicyclo[3.2.1]octane-8-carboxylic acid ethyl ester 2 (200.000 mg; 0.713 mmol; 1.000 eq.) was dissolved in DCE (4 mL) and treated with TEA (87.821 uL; 63.758 mg; 0.631 mmol; 1.000 eq.) and ethylaniline (91.79 mg; 0.856 mmol; 1.200 eq.), followed by NaBH (OAc)$_3$ (453.569 mg; 2.140 mmol; 3.000 eq.) and AcOH (40.870 uL; 42.873 mg; 0.713 mmol; 1.000 eq.). The reaction was allowed to stir at room temperature for 48 hr and was quenched with MeOH (3 mL). The quenched mixture was allowed to stir at room temperature for 2 hrs, and the resulting suspension was filtered through a syringe filter. A 1 mL aliquot of the filtrate was purified by LC/MS (1 mL injection, 10-99 CH$_3$CN gradient with 0.03% TFA, 15 minute run) to provide a pure sample of the desired product. LC/MS M/Z 372.2, retention time=1.82 minutes, 10-99% CH$_3$CN/H$_2$O gradient with 0.05% TFA.

Example 6

4-[Acetyl-(4-fluoro-phenyl)-amino]-[1,4']bipiperidinyl-1'-carboxylic acid ethyl ester (Compound No. 11)

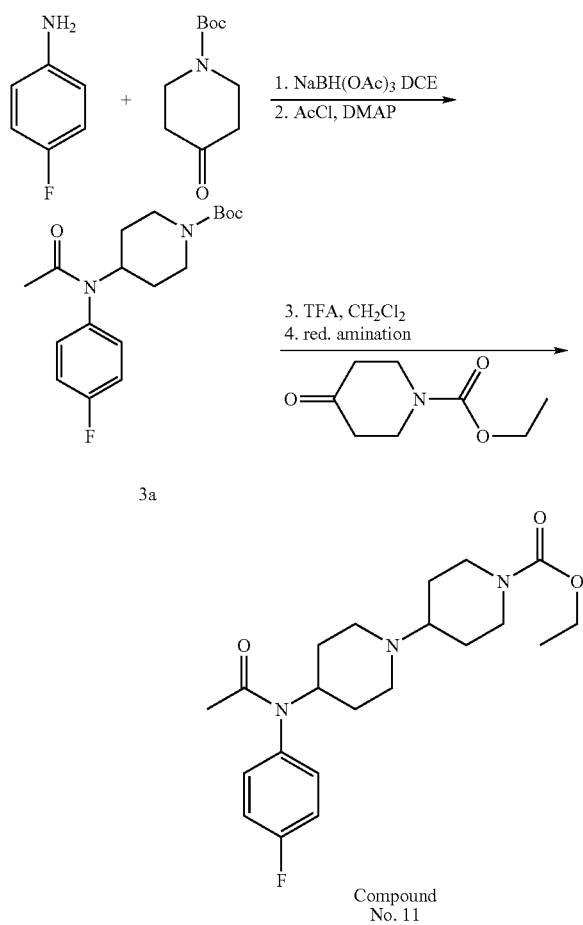

Compound No. 11

Step 1: Preparation of 4-(4-Fluoro-phenylamino)-piperidine-1-carboxylic acid tert-butyl ester (3a)

N-Boc-4-piperidinone (8.61 g; 43.2 mmol; 1.2 eq.) was dissolved in DCE (100 mL) and treated with 4-fluoroaniline (3.46 mL; 36.0 mmol; 1.0 eq.). Acetic acid (2.06 mL; 36.0 mmol; 1.0 eq.) was then added to the reaction flask followed by the portion-wise addition of NaBH(OAc)$_3$ (10.68 g; 50.4 mmol; 1.4 eq.). The mixture was stirred vigorously at room temperature for 4 hours. The reaction was quenched with 1N NaOH (100 mL) and the layers were separated. The aqueous layer was extracted with DCM (2×50 mL) and the combined organic layers were dried with Na$_2$SO$_4$, filtered, and concentrated under high vacuum.

The crude material was dissolved in Et$_2$O (150 mL, brief heating required) and treated with 1M HCl in Et$_2$O (35 mL). The solution was stirred at room temperature for 10 minutes and a precipitate was formed. The precipitate was filtered and washed with Et$_2$O (100 mL) to provide the product as an off-white solid. (LC/MS M/Z 295.3, Retention time=2.57 minutes; 10-99% CH$_3$CN/H$_2$O gradient with 0.05% TFA). H NMR (400 MHz, DMSO-d6, HCl salt) δ 7.62-7.59 (m, 2H), 7.39 (t, J=8.8 Hz, 2H), 3.99 (d, J=11.7 Hz, 2H), 3.59 (tt, J=11.4 Hz, 3.9 Hz, 1H), 2.72 (br s, 2H), 1.91-1.87 (m, 2H), 1.64-1.54 (m, 2H), 1.39 (s, 9H).

Step 2: Preparation of 4-[acetyl-(4-fluoro-phenyl)-amino]-piperidine-1-carboxylic acid tert-butyl ester 4-(4-Fluoro-phenylamino)-piperidine-1-carboxylic acid tert-butyl ester (2.8 g; 9.51 mmol; 1 eq.) was dissolved in DCM (30 mL) and Ac$_2$O (2.2 mL; 23.77 mmol; 2.5 eq.) was added. DMAP (1.51 g; 12.36 mmol; 1.3 eq.) was introduced and the reaction was stirred overnight (approx. 18 hours) at room temperature. The solution was diluted with DCM (150 mL) and washed with 1N HCl (50 mL). The organic layer was dried over Na$_2$SO$_4$, filtered, and concentrated under high vacuum to provide the product as an oil. The crude product was used without further purification. LC/MS M/Z 337.3, Retention time=2.95 minutes; 10-99% CH$_3$CN/H$_2$O gradient with 0.05% TFA). H NMR (400 MHz, CDCl$_3$) δ 7.16-7.05 (m, 4H), 4.77 (tt, J=12.2 Hz, 3.8 Hz, 1H), 4.13 (d, J=7.1 Hz, 2H), 2.81 (t, J=12.4 Hz, 2H), 1.82-1.73 (m, 2H), 1.77 (s, 3H), 1.41 (s, 9H), 1.26-1.16 (m, 2H).

Step 3: Preparation of N-(4-fluoro-phenyl)-N-piperidin-4-yl-acetamide

The crude 4-[acetyl-(4-fluoro-phenyl)-amino]-piperidine-1-carboxylic acid tert-butyl ester was dissolved in DCM (5 mL) and TFA (5 mL) was added. After 10 minutes of stirring at room temperature the excess TFA was removed under high vacuum. The residue was taken up in aqueous 1N HCl (60 mL) and washed with Et$_2$O (2×50 mL). The aqueous layer was then basified with NaOH and extracted with EtOAc (3×60 mL). The combined organic layers were dried over Na$_2$SO$_4$, filtered, and concentrated under high vacuum to provide the product as an oil. LC/MS M/Z 237.0, Retention time=0.74 minutes; 10-99% CH$_3$CN/H$_2$O gradient with 0.05% TFA). H NMR (400 MHz, CDCl$_3$) δ 7.13-7.06 (m, 4H), 4.72 (tt, J=12.2 Hz, 3.9 Hz, 1H), 3.07 (d, J=12.2 Hz, 2H), 2.74 (td, J=12.3, 1.9 Hz, 2H), 1.80-1.71 (m, 3H), 1.76 (s, 3H), 1.30-1.20 (m, 2H).

Step 4: Preparation of 4-[Acetyl-(4-fluoro-phenyl)-amino]-[1,4']bipiperidinyl-1,1'-carboxylic acid ethyl ester N-(4-Fluoro-phenyl)-N-piperidin-4-yl-acetamide (60 mg; 0.25 mmol; 1 eq.) and the N-boc-piperidine-4-one (53 mg; 0.30 mmol; 1.2 eq.) were dissolved in DCE (2 mL). Acetic acid (30 μl; 0.51 mmol; 2 eq.) was added followed by NaBH(OAc)$_3$ (108 mg; 0.51 mmol; 2 eq.). The reaction was stirred at room temperature for 72 hours and then quenched with 1N NaOH (10 mL). DCM (10 mL) was then added and the layers were separated. The aqueous layer was washed with DCM (20 mL) and the combined organic layers were dried over Na$_2$SO$_4$, filtered, and concentrated under reduced pressure. The crude residue was purified using reversed-phase HPLC (2-99% CH$_3$CN/H$_2$O gradient with 0.05% TFA). LC/MS M/Z 392.2, Retention time=1.71 minutes: 10-99% CH$_3$CN/H$_2$O gradient with 0.05% TFA. $^1$H NMR (400 MHz, MeOD, TFA salt) δ 7.34-7.25 (m, 4H), 4.81 (tt, J=12.3 Hz, 3.9 Hz, 1H), 4.28 (d, J=13.6 Hz, 2H), 4.13 (q, J=7.1 Hz, 2H), 3.58 (d, J=12.4 Hz, 2H), 3.38 (tt, J=11.1 Hz, 3.4 Hz, 1H), 3.22 (t, J=11.9 Hz, 2H), 2.85 (br s, 2H), 2.16 (d, J=13.1 Hz, 2H), 2.06 (d, J=11.5 Hz, 2H), 1.80 (s, 3H), 1.76-1.56 (m, 4H), 1.26 (t, J=7.1 Hz, 3H).

Example 7

N-(1-Cyclohexyl-piperidin-4-yl)-N-(4-fluoro-phenyl)-acetamide

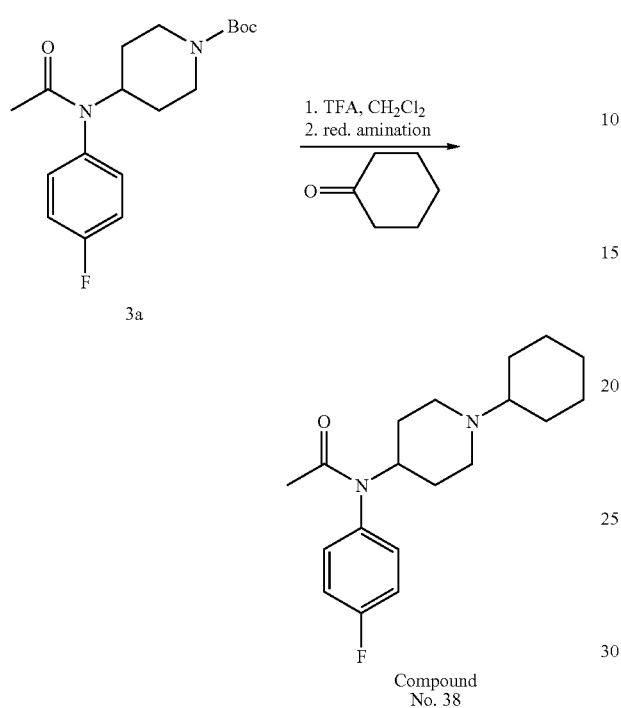

Compound No. 38

N-(4-fluoro-phenyl)-N-piperidin-4-yl-acetamide (60 mg; 0.25 mmol; 1 eq.), see Example 6 for deprotection procedure, and cyclohexanone (29 mg; 0.30 mmol; 1.2 eq.) were dissolved in DCE (2 mL). NaBH(OAc)$_3$ (108 mg; 0.51 mmol; 2 eq.) was added, and the reaction was stirred at room temperature for 72 hours and then quenched with 1N NaOH (5 mL). DCM (5 mL) was then added and the layers were separated. The aqueous layer was washed with DCM (10 mL) and the combined organic layers were dried over Na$_2$SO$_4$, filtered, and concentrated under reduced pressure. The crude residue was purified using reversed-phase HPLC (2-99% CH$_3$CN/H$_2$O gradient with 0.05% TFA). LC/MS M/Z 319.2, Retention time=1.88 minutes; 10-99% CH$_3$CN/H$_2$O gradient with 0.05% TFA.

Example 8

N-(1-Bicyclo[3.2.1]oct-3-yl-piperidin-4-yl)-N-(4-fluoro-phenyl)-acetamide (Compound No. 56)

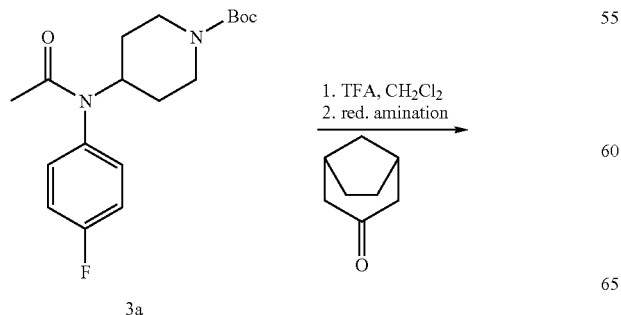

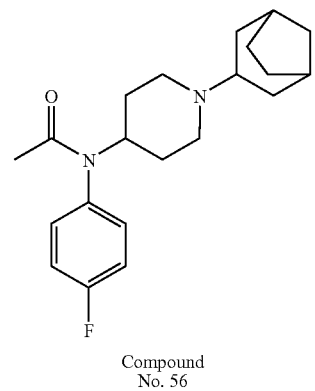

Compound No. 56

N-(4-fluoro-phenyl)-N-piperidin-4-yl-acetamide (60 mg; 0.25 mmol; 1 eq.), see Example 6 for deprotecting procedure, and bicyclo[3.2.1]octan-8-one (37 mg, 0.3 mmol, 1.2 eq.) were dissolved in dichloromethane (1.5 mL) and DCM (1.5 mL) and treated with Ti(O$^i$Pr)$_4$ (213 mg, 0.75 mol, 3 eq.). The reaction was stirred under nitrogen at room temperature for 48 hours, then cooled in a dry ice/isopropanol bath to ~−40° C. and quenched with methanol (4 mL). The reaction was stirred for 15 minutes at that temperature, then treated with 4.0 eq sodium borohydride (37 mg, 1 mmol). The reaction was slowly warmed to room temperature and stirred for 2 hours. The reaction was then treated with 1 N NaOH (2 mL), stirred vigorously for 30 minutes, filtered through Celite and the solids rinsed with CH$_2$Cl$_2$ (4×5 mL). The filtrates were combined and washed with H$_2$O, saturated brine, dried (Na$_2$SO$_4$) and filtered. The filtrate was concentrated under reduced pressure and the crude product was purified by preparative HPLC (2-99 H$_2$O—CH$_3$CN gradient, 15 minute method) to afford the desired product. LC/MS M/Z 345.3, retention time 2.34 minutes 10-99% CH$_3$CN/H$_2$O gradient with 0.05% TFA.

Example 9

3-{4-[Acetyl-(2-chloro-6-methyl-pyrimidin-4-yl)-amino]-piperidin-1-yl}-8-aza-bicyclo[3.2.1]octane-8-carboxylic acid ethyl ester (Compound No. 8)

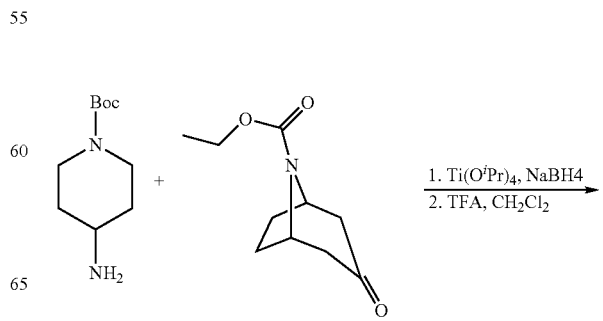

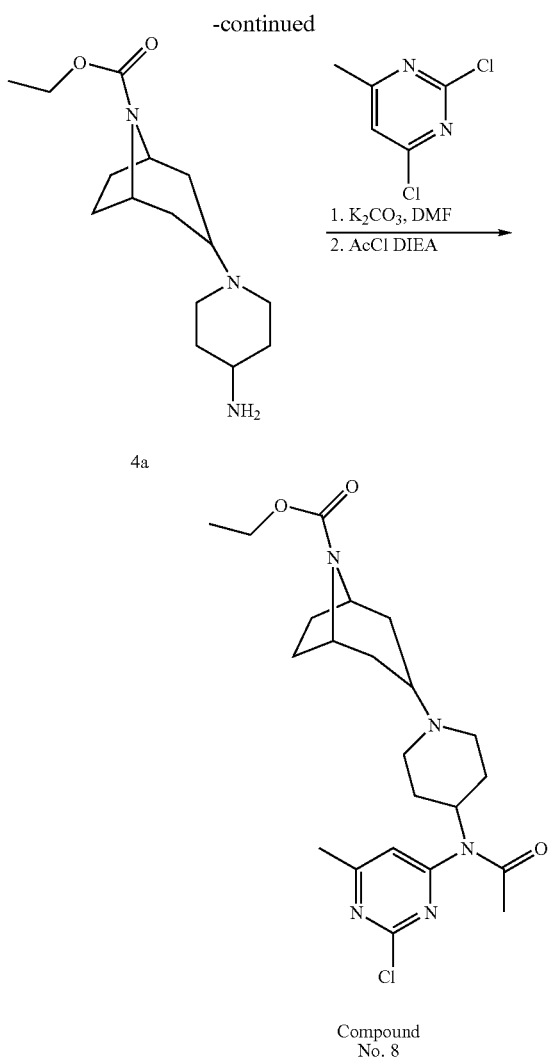

Preparation of 3-(4-Amino-piperidin-1-yl)-8-aza-bicyclo[3.2.1]octane-8-carboxylic acid ethyl ester (4a)

Step 1. 4-(N-Boc amino)-piperidine (8.393 g, 41.9 mmol) and N-(ethoxycarbonyl)-tropinone (9.92 g, 50.3 mmol) were dissolved in dichloromethane (50 mL) and treated with 3.0 eq Ti(O$^i$Pr)$_4$ (35.7 g, 0.126 mol). The reaction was stirred under nitrogen at room temperature for 10 hours, then cooled in a dry ice/isopropanol bath to ~−40° C. and quenched with methanol (200 mL). The reaction was stirred for 15 minutes at that temperature, then treated with sodium borohydride (3.17 g, 83.8 mmol) in several portions at −40° C. The reaction was slowly warmed to room temperature and stirred for 24 hours. The reaction was then treated with 1 N NaOH (80 mL), stirred vigorously for 30 minutes, filtered through Celite and the filter cake rinsed with CH$_2$Cl$_2$ (4×100 mL). The filtrates were combined and washed with water, saturated brine, dried (Na$_2$SO$_4$) and filtered. The filtrate as concentrated under reduced pressure to afford a product as a viscous, pale yellow oil.

Step 2: The crude N-Boc intermediate (16.325 g) was dissolved in dichloromethane (30 mL), cooled in an ice/water bath and slowly treated with ice-cold TFA (30 mL). The reaction was warmed to room temperature and stirred for 90 minutes. The reaction was concentrated under reduced pressure, the oil obtained re-dissolved in acetonitrile and re-concentrated (repeated once more). The crude TFA salt was treated with 2 N NaOH (50 mL) and extracted with dichloromethane (3×75 mL). The combined organic extracts were washed with saturated brine, dried (Na$_2$SO$_4$) and filtered. The filtrate was concentrated under reduced pressure to afford 11.47 g crude product as a viscous, pale yellow oil. The crude free base was dissolved in anhydrous diethyl ether (~50 mL) and treated with ~1.0 eq HCl [17.4 mL 2 N ethereal HCl. The suspension was cooled in an ice/H$_2$O bath, filtered, rinsed with Et$_2$O and briefly air dried. The solids were pulverized to a fine white powder and dried overnight under reduced pressure to afford the product.

Step 1: Preparation of 3-[4-(2,6-Dimethyl-pyrimidin-4-ylamino)piperidin-1-yl]-8-aza bicyclo[3.2.1]octane-8-carboxylic acid ethyl ester The 3-(4-Amino-piperidin-1-yl)-8-aza-bicyclo[3.2.1]octane-8-carboxylic acid ethyl ester (30 mg; 0.11 mmol; 1 eq.) was dissolved in DMF (3 mL) and 2,4-dichloro-6-methyl-pyrimidine (17 mg; 1 eq.) and K$_2$CO$_3$ (22 mg; 1.5 eq.) was added and the reaction was heated to 80° C. and stirred under N$_2$ overnight. The solution was diluted with H$_2$O (10 mL) and extracted with AcOEt (2×25 mL). The organic layer was washed with brine and dried over Na$_2$SO$_4$, filtered, and concentrated under high vacuum to provide the product as an oil. The crude product was used without further purification.

Step 2. Preparation of 3-{4-[Acetyl-(2-chloro-6-methyl-pyrimidin-4-yl)-amino]-piperidin-1-yl}-8-aza-bicyclo[3.2.1]octane-8-carboxylic acid ethyl ester (Compound no. 8)

3-[4-(2,6-Dimethyl-pyrimidin-4-ylamino)piperidin-1-yl]-8-aza-bicyclo[3.2.1]octane-8-carboxylic acid ethyl ester (20 mg; 0.05 mmol; 1 eq.) was dissolved in DCM (3 mL) and acetyl chloride (9.5 mg; 2.5 eq.) and DIEA (9.5 mg; 1.5 eq.) was added and the reaction was stirred overnight (approx. 14 hours) at 80° C. under N$_2$. The solution was diluted with DCM (10 mL) and washed with saturated NaHCO$_3$ (2×20 mL). The organic layer was dried over Na$_2$SO$_4$, filtered, and concentrated under high vacuum to provide the product as an oil (18 mg). The crude residue was purified by reversed-phase HPLC (2-99% CH$_3$CN/water gradient with 0.05% TFA). M+1=450.2, Retention time=1.81 minutes; 10-99% CH$_3$CN/H$_2$O gradient with 0.05% TFA.

Example 10

N-(1-(4-(ethoxyimino)cyclohexyl)piperidin-4-yl)-N-(4-fuorophenyl)acetamide (Compound No. 79)

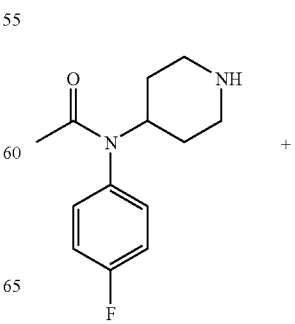

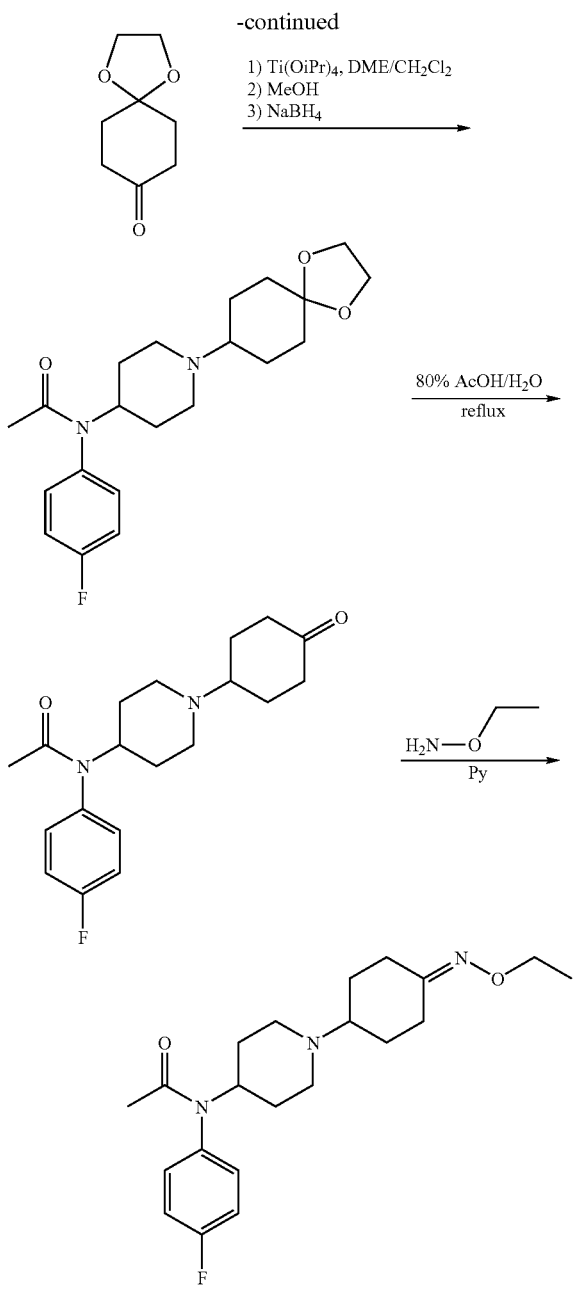

NaOH (1 mL) was added and after 10 minutes the solution was filtered and the precipitate was washed with MeOH (20 mL). The solvent was removed under high vacuum and the residue was taken up in EtOAc (50 mL) and 1N HCl (50 mL). The layers were separated, the organic layer was discarded, and the aqueous layer was basified with NaOH and extracted with EtOAc (2×50 mL). The combined organic extracts were dried over $Na_2SO_4$, filtered, and concentrated. The crude residue was obtained as a yellow solid. LC/MS m/z 377.0, Retention time=1.62 minutes; 10-99% $CH_3CN/H_2O$ gradient with 0.05% TFA).

Step 2 Preparation of N-(4-fluorophenyl)-N-(1-(4-oxocyclohexyl)piperidin-4-yl)acetamide N-(1-(1,4-dioxaspiro[4.5]decan-8-yl)piperidin-4-yl)-N-(4-fluorophenyl)acetamide (150 mg; 0.4 mmol; 1 eq.) was dissolved in 80% of aqueous AcOH (2 mL). The solution was heated to reflux for 18 hours. 1N NaOH (10 mL) was added and the solution was extracted with EtOAc (2×20 mL). The combined organic extracts were dried over $Na_2SO_4$, filtered, and concentrated under reduced pressure. The crude product was obtained as yellow oil (LC/MS m/z 333.2, Retention time=1.76; 10-99% $CH_3CN/H_2O$ gradient with 0.05% TFA).

Step 3 Preparation of N-(1-(4-(ethoxyimino)cyclohexyl)piperidin-4-yl)-N-(4-fluorophenyl)acetamide N-(4-fluorophenyl)-N-(1-(4-oxocyclohexyl)piperidin-4-yl)acetamide (100 mg; 0.3 mmol; 1 eq.) was dissolved in pyridine (2 mL). O-ethylhydroxylamine (22 mg, 0.36 mmol; 1.2 eq.) was added. The solution was heated to 80° C. for 30 min. Saturated $NaHCO_3$ (10 mL) was added and the solution was extracted with EtOAc (2×20 mL). The combined organic extracts were dried over $Na_2SO_4$, filtered, and concentrated under reduced pressure. The crude residue was purified by reversed-phase HPLC (2-99% $CH_3CN/H_2O$ gradient with 0.05% TFA) to provide the desired product. LC/MS m/z 333.2, Retention time=1.79; 10-99% $CH_3CN/H_2O$ gradient with 0.05% TFA).

Example 11

Ethyl 3-(2-oxo-1-phenyl-1,8-diazaspiro[4.5]decan-8-yl)-8-azabicyclo[3.2.1]octane-8-carboxylate (Compound No. 88)

Step 1: Preparation of N-(1-(1,4-dioxaspiro[4.5]decan-8-yl)piperidin-4-yl)-N-(4-fluorophenyl)acetamide N-(4-fluorophenyl)-N-(piperidin-4-yl)acetamide (Prepared as in Example 6, step 3) (200 mg; 0.85 mmol; 1 eq.) was dissolved in DCM (2.5 mL) and DME (2.5 mL). 1,4-dioxaspiro[4.5]decan-8-one (198 mg; 1.27 mmol; 1.5 eq.) was then introduced followed by Ti($O^iPr$)$_4$ (593 μL; 2.0 mmol; 5 eq.). The reaction was stirred at room temperature for approx. 72 hours. The solution was cooled to 40° C. and treated with MeOH (5 mL). After 10 minutes at −40° C., NaBH$_4$ (30 mg; 1.7 mmol; 2 eq.) was added. The solution was stirred at 40° C. for 30 minutes and then slowly warmed to room temperature and stirred at room temperature for an additional 1 hour. 1N

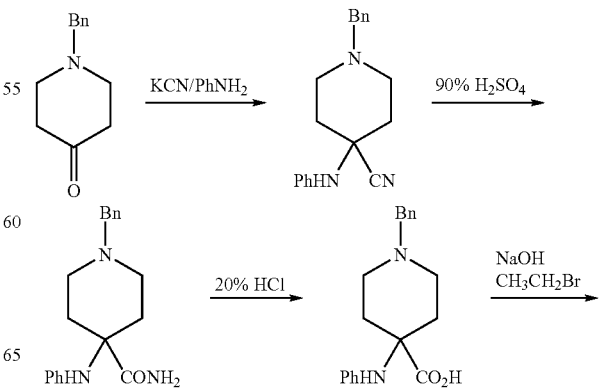

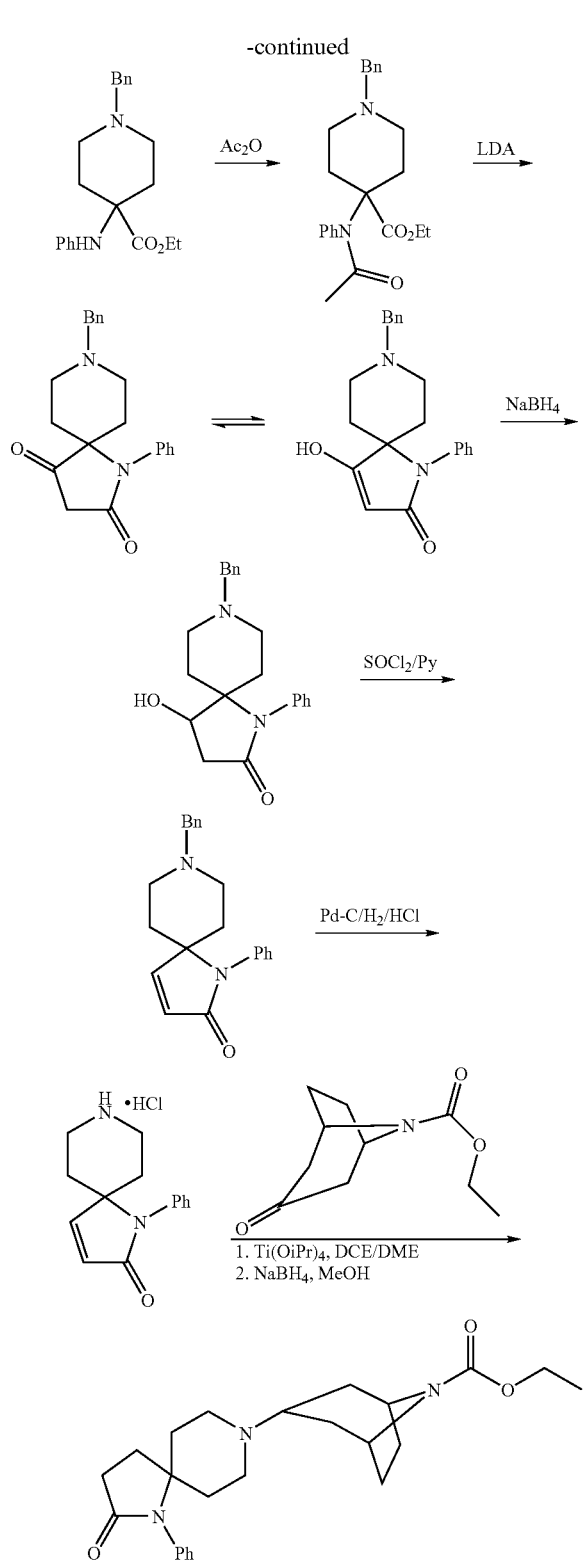

Step 1 Preparation of benzyl-4-phenylamino-piperidine-4-carbonitrile

To a solution of 1-benzyl-4-oxo-piperidine (226.8 g, 1.2 mol) and phenylamine (111.6 g, 1.2 mol) in acetic acid (1000 mL) was added dropwise the solution of potassium cyanide (117 g, 1.8 mol) in water (200 mL). The reaction mixture was stirred at 25° C. for 24 h and then poured into ice-water. The mixture was basified with ammonium hydroxide and extracted with $CH_2Cl_2$. The combined organic layers were washed with brine, dried over $Na_2SO_4$ and concentrated under reduced pressure to give crude benzyl-4-phenylamino-piperidine-4-carbonitrile (255.36 g, 73.1%), which was used directly in the next step. $^1$H NMR (300 MHz, $CDCl_3$) δ 7.22-7.36 (m, 7H), 6.90-6.94 (m, 3H), 3.65 (br s, 1H), 3.58 (s, 2H), 2.74-2.86 (m, 2H), 2.44-2.52 (m, 2H), 2.32-2.37 (m, 2H), 1.92-2.00 (m, 2H).

Step 2 Preparation of 1-benzyl-4-(phenylamino)piperidine-4-carboxamide

To a solution of $H_2SO_4$ (750 g, 98%) in water (83.3 mL) was added benzyl-4-phenylamino-piperidine-4-carbonitrile (125 g, 0.43 mol) in portions at 20° C. The mixture was heated to 55° C. for 2 hours. After cooling, the reaction mixture was poured into ice-water (200 mL). The precipitate was collected by filtration and poured into water (1000 mL). The resulting mixture was basified with 10% aqueous NaOH to pH 8. The precipitate was collected by filtration and washed with methanol (100 mL) to give 2 (74.4 g, 56%), which was used directly in the next step.

Step 3: Preparation of benzyl-4-phenylamino-piperidine-4-carboxylic acid 3

Preparation of 1-benzyl-4-(phenylamino)piperidine-4-carboxamide (74.4 g, 0.24 mol) was dissolved in 20% HCl (1500 mL). The mixture was heated to reflux overnight. After cooling, the reaction mixture was poured into ice-water (200 mL). The precipitated solid was filtered and then poured into water (1000 mL). The resulting mixture was basified with 10% NaOH aqueous solution to pH 8. The precipitated solid was collected by filtration and washed with methanol (100 mL) to give 2), which was used directly in the next step.

Step 4: Preparation of ethyl 1-benzyl-4-(phenylamino)piperidine-4-carboxylate Benzyl-4-phenylamino-piperidine-4-carboxylic acid (40.1 g, 0.13 mol) and NaOH (5.12 g, 0.13 mol) was dissolved in methanol (1000 mL). The mixture was heated to reflux for 0.5 h. Then the solvent was removed under reduced pressure. The residue was dissolved in HMPT (300 mL). Bromoethane (17.44, 0.16 mol) was added at 20° C. The mixture was stirred overnight at 20° C. The reaction mixture was poured into ice-water and extracted with EtOAc (3×400 mL). The combined organics were washed with brine, dried over $Na_2SO_4$ and evaporated under vacuum. The residue was purified by silicagel column chromatography (Petroleum ether./EtOAc 2:1) to give ethyl 1-benzyl-4-(phenylamino)piperidine-4-carboxylate.

$^1$H NMR (300 MHz, $CDCl_3$) δ 7.26-7.32 (m, 5H), 7.10-7.15 (m, 2H), 6.74 (t, J=7.5 Hz, 1H), 6.58 (d, J=7.5 Hz, 2H), 4.13 (q, J=7.2 Hz, 2H), 3.51 (s, 2H), 2.59-2.63 (m, 2H), 2.39-2.46 (m, 2H), 2.20-2.29 (m, 2H), 2.00-2.04 (m, 2H), 1.14 (t, J=7.2 Hz, 3H).

Step 5 Preparation of ethyl 1-benzyl-4-(N-phenylacetamido)piperidine-4-carboxylate A mixture of acetic acid anhydride (150 mL) and ethyl 1-benzyl-4-(phenylamino) piperidine-4-carboxylate (26.8 g, 79.3 mmol) was heated to reflux for 5 h. After cooling, the reaction mixture was poured into ice-water and basified with saturated aqueous NaHCO$_3$ to pH 8. The mixture was extracted with EtOAc (3×200 mL). The combined organics were washed with brine, dried over Na$_2$SO$_4$ and evaporated under vacuum to give ethyl 1-benzyl-4-(N-phenylacetamido)piperidine-4-carboxylate. $^1$H NMR (300 MHz, CDCl$_3$) δ 7.36-7.42(m, 3H), 7.19-7.31 (m, 7H), 4.24 (q, J=7.2 Hz, 2H), 3.46 (s, 2H), 2.59-2.63 (m, 2H), 2.39-2.46 (m, 2H), 2.20-2.28 (m, 2H), 1.59-1.69 (m, 5H), 1.29 (t, J=7.2 Hz, 3H).

Step 6 Preparation of 8-benzyl-1-phenyl-1,8-diaza-spiro[4.5]decane-2,4-dione Diisopropylamine (1.54 g, 15 mmol) was dissolved in THF (50 mL) and then the mixture was cooled to −78° C. n-Butyl lithium (6.1 mL, 2.5 M in hexane) was added dropwise at −78° C. After addition, the reaction mixture was stirred for 30 min at −78° C. Ethyl 1-benzyl-4-(N-phenylacetamido)piperidine-4-carboxylate (2.9 g, 7.6 mmol) was added dropwise at −78° C. The mixture was continued to stir for 1 h at −78° C. The reaction was quenched by dropwise addition of water (10 mL) at −78° C. and then allowed to warm to room temperature. The organic layer was separated. The aqueous phase was acidified to pH 6-7 with acetic acid and extracted with EtOAc (3×20 mL). The combined organics were washed with brine, dried over Na$_2$SO$_4$ and evaporated under vacuum to give crude product as a solid, which was washed with ether to give 8-benzyl-1-phenyl-1,8-diazaspiro[4.5]decane-2,4-dione. $^1$H NMR (300 MHz, MeOD) δ 7.12-7.47 (m, 15H), 4.04 (s, 2H), 3.65-3.66 (m, 2H), 3.51-3.57 (m, 1H), 3.02-3.06 (m, 2H), 2.66-2.73 (m, 2H), 1.93-2.00 (m, 5H), 1.82-1.87 (m, 1H).

Step 7 Preparation of 8-benzyl-4-hydroxy-1-phenyl-1,8-diazaspiro[4.5]decan-2-one To a solution of 8-benzyl-1-phenyl-1,8-diazaspiro[4.5]decane-2,4-dione (2.3 g, 6.85 mmol) in methanol (50 mL) was added NaBH$_4$ (0.78 g, 20.5 mmol) in portions at 15° C. The mixture was stirred for 1 h at 15° C. H$_2$O (5 mL) was added slowly at 0° C. The solvent was removed under reduced pressure to give crude product, which was dissolved in EtOAc. The organic layer was washed with water, dried over Na$_2$SO$_4$ and evaporated to give 8-benzyl-4-hydroxy-1-phenyl-1,8-diazaspiro[4.5]decan-2-one, which was used directly in the next step.

Step 8 Preparation of 8-benzyl-1-phenyl-1,8-diazaspiro[4.5]dec-3-en-2-one

To 8-benzyl-4-hydroxy-1-phenyl-1,8-diazaspiro[4.5]decan-2-one (400 mg, 1.19 mmol) in pyridine (10 mL) was added thionyl chloride (0.26 g, 3.57 mmol) at 0° C. under N$_2$. The mixture was heated to 50° C. for 5 hours. The solvent was removed under reduced pressure. The residue was dissolved in EtOAc (50 mL) and washed with sat aqueous NaHCO$_3$. The organic layer was separated, dried over Na$_2$SO$_4$ and evaporated to give crude 8-benzyl-1-phenyl-1,8-diaza-spiro[4.5]dec-3-en-2-one, which was purified by column (Petroleum ether/EtOAc 4:1) to give 8-benzyl-1-phenyl-1,8-diazaspiro[4.5]dec-3-en-2-one. $^1$H NMR (300 MHz, MeOD) δ 7.89 (d, J=6.0 Hz, 1H), 7.44-7.52 (m, 3H), 7.17-7.27 (m, 5H), 7.14-7.17 (m, 2H), 6.26 (d, J=6.3 Hz, 1H) 3.54 (s, 2H), 2.87-2.91 (m, 2H), 2.35-2.44 (m, 2H), 1.99-2.09 (m, 2H), 1.59-1.64 (m, 2H).

Step 9 Preparation of 1-phenyl-1,8-diazaspiro[4.5]decan-2-one hydrochloride

To a suspension of Pd/C (30 mg, 10%) in isopropanol (5 mL), water (5 mL) and hydrochloric acid (0.04 mL) was added 8-benzyl-1-phenyl-1,8-diaza-spiro[4.5]dec-3-en-2-one (150 mg 0.5 mmol). The mixture was hydrogenated under H$_2$ (50 psi) at 20° C. for 5 hours. After filtration, the filtrate was evaporated under reduced pressure to give 1-phenyl-1,8-diazaspiro[4.5]decan-2-one hydrochloride. $^1$H NMR (300 MHz, MeOD) δ 7.42-7.52 (m, 3H), 7.15-7.41 (m, 2H), 3.29-3.33 (m, 2H), 3.06-3.16 (m, 2H), 2.63 (t, J=7.8 Hz, 2H), 2.31 (t, J=8.1 Hz, 2H) 1.96-2.00 (m, 2H), 1.78-1.89 (m, 2H).

Step 10 Preparation of ethyl 3-(2-oxo-1-phenyl-1,8-diazaspiro[4.5]decan-8-yl)-8-azabicyclo[3.2.1]octane-8-carboxylate 1-Phenyl-1,8-diazaspiro[4.5]decan-2-one hydrochloride (20.00 g, 75.0 mmol) was dissolved in DCE (0.5 ml) and DCE (0.5 ml) and treated with 1-phenyl-1,8-diazaspiro[4.5]decan-2-one hydrochloride (20.00 g, 75.0 mmol), followed by 1-phenyl-1,8-diazaspiro[4.5]decan-2-one hydrochloride (20.00 g, 75.0 mmol) and 1-phenyl-1,8-diazaspiro[4.5]decan-2-one hydrochloride (20.00 g, 75.0 mmol). The reaction was placed under a nitrogen atmosphere and was allowed to stir for 3 days at room temperature. The solution was cooled to −40° C. and treated with MeOH (2 mL). After 10 minutes at −40° C., Sodium borohydride (6.63 ml, 187 mmol) was added. The solution was stirred at −40° C. for 30 minutes and then slowly warmed to room temperature and stirred at room temperature for an additional 1 hour. 1N NaOH (1 mL) was added and after 10 minutes the solution was filtered and the precipitate was washed with MeOH (10 mL). The solvent was removed under high vacuum and the residue was taken up in EtOAc (20 mL) and 1N HCl (20 mL). The layers were separated, the organic layer was discarded, and the aqueous layer was basified with NaOH and extracted with EtOAc (2×20 mL). The combined organic extracts were dried over Na$_2$SO$_4$, filtered, and concentrated.

The crude product was purified by reverse-phase HPLC (10-99% CH$_3$CN/H$_2$O gradient with 0.05% TFA) to provide ethyl 3-(2-oxo-1-phenyl-1,8-diazaspiro[4.5]decan-8-yl)-8-azabicyclo[3.2.1]octane-8-carboxylate as the corresponding TFA salt. LC/MS m/z 412.5, Retention time=2.0 minutes; 10-99% CH$_3$CN/H$_2$O gradient with 0.05% TFA).

A person skilled in the chemical arts can use the examples and schemes along with known synthetic methodologies to synthesize compounds of the present invention, including the compounds in Table 2 below.

TABLE 2

Physical data for exemplary compounds.

| Compound No. | LC/MS M + 1 | LC/RT min |
|---|---|---|
| 1 | 345.2 | 2.06 |
| 2 | 446 | 2.16 |
| 3 | 446.4 | 2.19 |
| 4 | 435.5 | 2.25 |
| 5 | 418.4 | 1.94 |

TABLE 2-continued

Physical data for exemplary compounds.

| Compound No. | LC/MS M + 1 | LC/RT min |
|---|---|---|
| 6 | 446.4 | 2.19 |
| 7 | 434 | 2.03 |
| 9 | 390.2 | 1.93 |
| 10 | 430 | 1.97 |
| 12 | 458 | 1.9 |
| 13 | 414 | 220 |
| 14 | 414 | 2.32 |
| 15 | 392.4 | 1.86 |
| 16 | 442.2 | 2.04 |
| 17 | 456 | 2.36 |
| 18 | 476 | 2.35 |
| 19 | 532.2 | 2.58 |
| 20 | 446.4 | 2.26 |
| 21 | 418 | 2.08 |
| 22 | 400 | 1.78 |
| 23 | 436.2 | 1.86 |
| 24 | 444.2 | 2.08 |
| 25 | 446.4 | 2.26 |
| 26 | 359 | 2.13 |
| 27 | 372.4 | 1.81 |
| 28 | 546.4 | 2.7 |
| 29 | 335.4 | 1.79 |
| 30 | 414 | 2.28 |
| 31 | 404.3 | 1.77 |
| 32 | 444.2 | 2.08 |
| 33 | 331 | 1.86 |
| 34 | 347 | 2.18 |
| 35 | 414 | 1.82 |
| 36 | 432.4 | 2.07 |
| 39 | 332.5 | 1.93 |
| 40 | 319.2 | 1.88 |
| 41 | 387.2 | 1.79 |
| 42 | 428 | 2.35 |
| 43 | 374.3 | 2.3 |
| 44 | 418 | 2.24 |
| 45 | 347 | 2.18 |
| 47 | 332.5 | 1.93 |
| 48 | 446.4 | 2.19 |
| 49 | 347.2 | 2.09 |
| 50 | 446.4 | 2.19 |
| 51 | 364.3 | 2.02 |
| 52 | 430 | 1.97 |
| 53 | 430 | 1.96 |
| 54 | 436 | 2.03 |
| 55 | 442.5 | 2.32 |
| 57 | 454.2 | 1.98 |
| 58 | 331 | 1.86 |
| 59 | 434 | 2 |
| 60 | 366 | 2 |
| 61 | 461.3 | 2.31 |
| 62 | 345.3 | 2.34 |
| 63 | 406 | 2.06 |
| 65 | 388.5 | 2.5 |
| 66 | 460.4 | 2.19233 |
| 67 | 432 | 2.11 |
| 68 | 319.1 | 1.81 |
| 69 | 460.4 | 2.19233 |
| 73 | 432.4 | 2.08 |
| 74 | 448.2 | 2.06 |
| 75 | 402.4 | 1.93 |
| 76 | 450.2 | 2.21 |
| 77 | 417.4 | 1.99 |
| 78 | 486.2 | 2.29 |
| 80 | 390.4 | 2.01 |
| 81 | 361.2 | 2.11 |
| 82 | 347.2 | 1.94 |
| 83 | 335.4 | 1.89 |
| 84 | 363.6 | 2.24 |
| 85 | 337.0 | 1.57 |
| 86 | 392.2 | 1.91 |
| 87 | 400.2 | 1.94 |
| 89 | 414.4 | 2.13 |

V. Assays for Detecting and Measuring Inhibition Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12440-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 µg/ml of Streptomycin (GIBCO Cat# 15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat# 15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM, $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat # R7181) adding 5 µl of a 5× solution dye in Bath 1 containing 1 mM Probenecid (10 ml per dye flask cat# R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I, II, and III) on modulating $M_1$-$M_4$ receptors are shown below in Table 3 and Table 4. The compound activity for the $M_1$, $M_2$, $M_3$ and $M_4$ is illustrated with "+++" if activity was measured to be less than 2.0 μM, "++" if activity was measured to be from 2.0 μM to 5.0 μM, "+" if activity was measured to be greater than 5.0 μM, and "−" if no data was available. The efficacy for $M_1$, and $M_4$ modulation is illustrated with "+++" if efficacy was calculated to be greater than 100%. "++" if efficacy was calculated to be from 100% to 25%, "+" if efficacy was calculated to be less than 25%, and "−" if no data was available. It should be noted that 100% efficacy is the maximum response obtained with the Carbachol control.

TABLE 3

Compound activities for modulating $M_1$-$M_4$ receptors.

| Compound No. | $M_1$ Activity | $M_2$ Activity | $M_3$ Activity | $M_4$ Activity |
| --- | --- | --- | --- | --- |
| 1 | +++ | + | + | + |
| 2 | +++ | + | + | ++ |
| 3 | +++ | + | + | + |
| 4 | + | + | − | + |
| 5 | +++ | + | ++ | +++ |
| 6 | +++ | + | + | + |
| 7 | +++ | + | ++ | +++ |
| 8 | − | − | − | − |
| 9 | + | + | + | + |
| 10 | + | + | + | + |
| 11 | +++ | + | + | ++ |
| 12 | +++ | + | + | + |
| 13 | +++ | + | + | +++ |
| 14 | +++ | + | + | +++ |
| 15 | +++ | +++ | ++ | +++ |
| 16 | +++ | ++ | + | +++ |
| 17 | + | + | + | + |
| 18 | ++ | + | + | ++ |
| 19 | + | + | + | + |
| 20 | +++ | + | + | + |
| 21 | +++ | + | + | +++ |
| 22 | +++ | +++ | + | +++ |
| 23 | +++ | + | + | ++ |
| 24 | +++ | + | + | + |
| 25 | +++ | + | + | + |
| 26 | ++ | + | + | + |
| 27 | +++ | + | + | + |
| 28 | + | + | + | + |
| 29 | + | + | + | + |
| 30 | +++ | + | + | ++ |
| 31 | +++ | + | + | + |
| 32 | +++ | + | + | + |
| 33 | ++ | + | + | + |
| 34 | ++ | + | + | + |
| 35 | +++ | + | + | ++ |
| 36 | +++ | + | + | + |
| 37 | +++ | + | + | +++ |
| 38 | + | + | + | + |
| 39 | ++ | + | + | + |
| 40 | + | + | + | +++ |
| 41 | +++ | + | + | +++ |
| 42 | +++ | + | ++ | +++ |
| 43 | + | + | − | + |
| 44 | +++ | + | + | ++ |
| 45 | ++ | + | + | + |
| 46 | +++ | ++ | + | +++ |
| 47 | ++ | + | + | + |
| 48 | +++ | + | + | + |
| 49 | ++ | + | + | + |
| 50 | +++ | + | + | + |
| 51 | + | + | + | + |
| 52 | +++ | + | + | ++ |
| 53 | +++ | + | + | ++ |
| 54 | +++ | + | + | + |
| 55 | + | + | + | + |
| 56 | ++ | + | + | + |
| 57 | + | + | + | + |
| 58 | ++ | + | + | + |
| 59 | +++ | + | + | +++ |
| 60 | ++ | + | + | + |
| 61 | ++ | + | − | ++ |
| 62 | ++ | + | + | + |
| 63 | +++ | ++ | ++ | +++ |
| 64 | ++ | + | + | + |
| 65 | + | + | − | + |
| 66 | +++ | + | + | + |
| 67 | +++ | + | + | +++ |
| 68 | + | + | + | + |
| 69 | +++ | + | + | + |
| 70 | +++ | + | + | +++ |
| 71 | +++ | + | + | ++ |
| 72 | + | + | + | + |
| 73 | +++ | + | + | + |
| 74 | +++ | + | + | ++ |
| 75 | +++ | + | + | + |
| 76 | +++ | + | + | + |
| 77 | ++ | + | + | + |
| 78 | ++ | + | + | + |
| 79 | +++ | + | + | + |
| 80 | +++ | + | + | + |
| 81 | +++ | + | + | +++ |
| 82 | +++ | + | + | + |
| 83 | +++ | + | + | ++ |
| 84 | +++ | + | + | ++ |
| 85 | ++ | + | + | ++ |
| 86 | +++ | +++ | + | +++ |
| 87 | +++ | + | + | ++ |
| 88 | +++ | +++ | + | +++ |
| 89 | +++ | + | + | ++ |

TABLE 4

Exemplary compound efficacies for modulating $M_1$-$M_4$ receptors.

| Compound No. | $M_1$ Efficacy | $M_2$ Efficacy | $M_3$ Efficacy | $M_4$ Efficacy |
| --- | --- | --- | --- | --- |
| 1 | ++ | + | + | + |
| 2 | ++ | + | + | ++ |
| 3 | ++ | + | + | + |
| 4 | ++ | + | − | ++ |
| 5 | ++ | + | + | ++ |
| 6 | ++ | + | + | + |
| 7 | ++ | + | ++ | ++ |
| 8 | − | − | − | − |
| 9 | ++ | + | + | ++ |
| 10 | ++ | + | + | ++ |
| 11 | ++ | + | ++ | ++ |
| 12 | ++ | + | + | + |
| 13 | ++ | + | ++ | ++ |
| 14 | ++ | + | + | ++ |
| 15 | ++ | ++ | ++ | ++ |
| 16 | ++ | ++ | ++ | ++ |
| 17 | ++ | + | + | + |
| 18 | ++ | + | + | ++ |
| 19 | + | + | + | + |
| 20 | ++ | + | + | + |
| 21 | ++ | + | + | ++ |
| 22 | ++ | + | + | ++ |
| 23 | ++ | + | + | ++ |

TABLE 4-continued

Exemplary compound efficacies for modulating $M_1$-$M_4$ receptors.

| Compound No. | $M_1$ Efficacy | $M_2$ Efficacy | $M_3$ Efficacy | $M_4$ Efficacy |
|---|---|---|---|---|
| 24 | ++ | + | + | + |
| 25 | ++ | + | + | + |
| 26 | ++ | + | + | + |
| 27 | ++ | + | + | + |
| 28 | + | + | + | + |
| 29 | + | + | + | + |
| 30 | ++ | + | + | ++ |
| 31 | ++ | + | + | ++ |
| 32 | ++ | + | + | + |
| 33 | ++ | + | + | + |
| 34 | ++ | + | + | + |
| 35 | ++ | ++ | ++ | ++ |
| 36 | ++ | + | + | + |
| 37 | ++ | + | + | + |
| 38 | ++ | + | + | + |
| 39 | ++ | + | + | + |
| 40 | ++ | + | + | ++ |
| 41 | ++ | + | + | ++ |
| 42 | ++ | + | ++ | ++ |
| 43 | + | + | − | + |
| 44 | ++ | + | + | ++ |
| 45 | ++ | + | + | + |
| 46 | ++ | ++ | ++ | ++ |
| 47 | ++ | + | + | + |
| 48 | ++ | + | + | + |
| 49 | ++ | + | + | + |
| 50 | ++ | + | + | + |
| 51 | + | + | + | + |
| 52 | ++ | + | + | + |
| 53 | ++ | + | + | ++ |
| 54 | ++ | + | ++ | + |
| 55 | ++ | + | + | + |
| 56 | ++ | + | + | + |
| 57 | ++ | + | + | + |
| 58 | ++ | + | + | + |
| 59 | ++ | + | ++ | ++ |
| 60 | ++ | + | + | + |
| 61 | ++ | ++ | − | ++ |
| 62 | ++ | + | + | + |
| 63 | ++ | + | ++ | ++ |
| 64 | ++ | + | + | + |
| 65 | + | + | − | + |
| 66 | ++ | + | + | + |
| 67 | ++ | + | ++ | ++ |
| 68 | ++ | + | + | + |
| 69 | ++ | + | + | + |
| 70 | ++ | + | + | ++ |
| 71 | ++ | + | ++ | ++ |
| 72 | ++ | + | + | ++ |
| 73 | ++ | + | + | + |
| 74 | ++ | + | + | ++ |
| 75 | ++ | + | + | + |
| 76 | ++ | + | + | + |
| 77 | + | + | + | + |
| 78 | ++ | + | + | + |
| 79 | ++ | + | + | ++ |
| 80 | ++ | + | − | ++ |
| 81 | ++ | + | + | ++ |
| 82 | ++ | + | + | + |
| 83 | ++ | + | + | + |
| 84 | ++ | + | + | + |
| 85 | ++ | + | + | ++ |
| 86 | ++ | ++ | + | ++ |
| 87 | ++ | + | + | ++ |
| 88 | ++ | ++ | + | ++ |
| 89 | ++ | + | + | + |

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula III

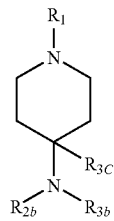

or a pharmaceutically acceptable salt thereof, wherein
$R_1$ is one selected from N-(ethoxy(carbonyl))piperidine-4-yl; N-(ethoxy(carbonyl))-8-azabicyclo[3.2.1]octane-3-yl; N-(butoxy(carbonyl))-8-azabicyclo[3.2.1]octane-3-yl; N-(isopropoxy(carbonyl))-8-azabicyclo[3.2.1]octane-3-yl; N-(tert-butoxy(carbonyl))-8-azabicyclo[3.2.1]octane-3-yl; N-(cyclobutoxy(carbonyl))-8-azabicyclo[3.2.1]octane-3-yl; tetrahydro-4H-pyran-4-yl; 4-(ethyl)cyclohexane-yl; bicyclo[2.2.1]heptane-2-yl; bicyclo[3.2.1]octane-3-yl; cyclohexane-yl; (cyclopentyl)methyl; bicyclo[2.2.1]hept-2-ylmethyl; cycloheptane-yl; cyclooctane-yl; bicyclo[3.3.1]nonane-9-yl; (tetrahydro-4H-pyran-2-yl)methyl; N-(butoxy(carbonyl))-8-azabicyclo[3.2.1]octane-3-yl; N-2,2-difluoroethoxy(carbonyl))-8-azabicyclo[3.2.1]octane-3-yl; N-(2-fluoroethoxy(carbonyl))-8-azabicyclo[3.2.1]octane-3-yl; N-(but-2-ynoxy(carbonyl))-8-azabicyclo[3.2.1]octane-3-yl; N-(trifluoromethyl(carbonyl))-8-azabicyclo[3.2.1]octane-3-yl; N-(methoxy(carbonyl))-8-azabicyclo[3.2.1]octane-3-yl; N-(methoxy(ethoxy(carbonyl))-8-azabicyclo[3.2.1]octane-3-yl; N-(ethyl(carbonyl))-8-azabicyclo[3.2.1]octane-3-yl; N-(phenyl(carbonyl))-8-azabicyclo[3.2.1]octane-3-yl; N-(N,N-(dimethyl(amino(carbonyl))-8-azabicyclo[3.2.1]octane-3-yl; N-(phenyl(sulfonyl))-8-azabicyclo[3.2.1]octane-3-yl; 4-(ethoxy(imino))cyclohexane-yl; 4-(propoxy(imino))cyclohexane-yl; bicyclo[3.2.1]octane-3-yl; N-(isobutoxy(carbonyl))-8-azabicyclo[3.2.1]octane-3-yl; N-(2,2-dimethylpropyloxy(carbonyl))-8-azabicyclo[3.2.1]octane-3-yl; 4-(but-2-ynyloxyimino)cyclohexane-yl; and 4-(pent-2-ynyl(imino))cyclohexane-yl;

$R_{2b}$ is —$Z^I R_{12}$, wherein $Z^I$ is a bond or an optionally substituted straight or branched $C_{1-5}$ aliphatic chain; $R_{12}$ is an aryl, a cycloaliphatic, a heteroaryl, or an aliphatic, each of which is optionally substituted with 1-3 of $R^{Z6}$; Each $R^{Z6}$ is independently selected from halo, optionally substituted aliphatic, and alkoxy;

$R_{3b}$ is —$Z^J R_{13}$, wherein $Z^J$ is —C(O)—, —S(O)$_2$—, —C(O)NH—, or —C(O)O—, and $R_{13}$ is hydrogen or an optionally substituted aliphatic, or an optionally substituted aryl;

$R_{3C}$ is hydrogen, or $R_{3C}$ and $R_{3b}$ together with the atoms to which they are attached form an optionally substituted 5-6 membered heterocycloaliphatic; and n is 1-8;

Provided that:
only one of $R_{2b}$ and $R_{3b}$ is an optionally substituted aryl or an optionally substituted heteroaryl;
when $Z^A$ is a bond, and $R_4$ is a substituted piperidine-4-yl; then $R_4$ is substituted with 1-3 of halo, hydroxy, cyano, or optionally substituted aliphatic, optionally substituted cycloaliphatic, optionally substituted aryl, optionally substituted heteroaryl, or combinations thereof; and when $Z^I$ is a bond and $R_{12}$ is a phenyl, $R_{12}$ is optionally substituted with 1-3 of halo, unsubstituted aliphatic, haloaliphatic, alkoxy, or combinations thereof.

2. The compound of claim 1, wherein $R_{2b}$ is —$Z^I R_{12}$, wherein $Z^I$ is a bond or an optionally substituted straight or branched $C_{1-5}$ aliphatic chain, and $R_{12}$ is an aryl optionally substituted with 1-5 of $R^{Z4}$.

3. The compound of claim 1, wherein $R_{2b}$ is —$Z^I R_{12}$, wherein $Z^I$ is a bond or an optionally substituted straight or branched $C_{1-5}$ aliphatic chain, and $R_{12}$ is a $C_{1-5}$ aliphatic that is optionally substituted with 1-5 of $R^{Z4}$.

4. The compound of claim 3, wherein $R_{2b}$ is —$Z^I R_{12}$, wherein $Z^I$ is a bond, and $R_{12}$ is a methyl optionally substituted with aryl or cycloaliphatic.

5. The compound of claim 1, wherein $R_{2b}$ is —$Z^I R_{12}$, wherein $Z^I$ is a bond or an optionally substituted straight or branched $C_{1-5}$ aliphatic chain, and $R_{12}$ is a cycloaliphatic that is optionally substituted with 1-3 of $R^{Z4}$.

6. The compound of claim 1, wherein $R_{2b}$ is —$Z^I R_{12}$, wherein $Z^I$ is a bond or an optionally substituted straight or branched $C_{1-5}$ aliphatic chain, and $R_{12}$ is a heteroaryl optionally substituted with 1-3 of $R^{Z4}$.

7. The compound of claim 1, wherein $R_{2b}$ is one selected from 4-fluorophenyl; phenyl; 2-fluorophenyl; phenylmethyl; 3-fluorophenyl; 4-methylphenyl; 3-methylphenyl; 3,4 -dimethylphenyl; 3-methoxyphenyl; 4-methoxyphenyl; 4-(tert-butyl)phenyl; 3-chlorophenyl; 3 -methoxycarbonyl; 4-chlorophenyl; cyclohexane-yl; 2,4-difluorophenyl; isopropyl; cyclopentane -yl; cyclobutane-yl; propyl; 2-chloro-4-methyl-pyrimidine-6-yl; and isobutyl.

8. The compound of claim 1, wherein $R_{3b}$ is —$Z^J R_{13}$, $Z^J$ is —C(O)—, and $R_{13}$ is an optionally substituted aliphatic, or an optionally substituted aryl.

9. The compound of claim 1, wherein $R_{3b}$ is —$Z^J R_{13}$, $Z^J$ is —S(O)$_2$—, and $R_{13}$ is an aliphatic or an aryl, each of which is optionally substituted.

10. The compound of claim 9, wherein $R_{3b}$ is one selected from (propyl(amino))carbonyl; methylcarbonyl; (methoxy)carbonyl; (isopropyl)carbonyl; (ethyl)carbonyl; methyl; ethyl; (methyl)sulfonyl; propyl; and 4-(trifluoro(methyl(phenyl)))sulfonyl.

11. A compound selected from:

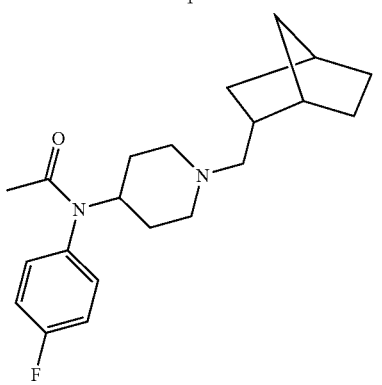

1

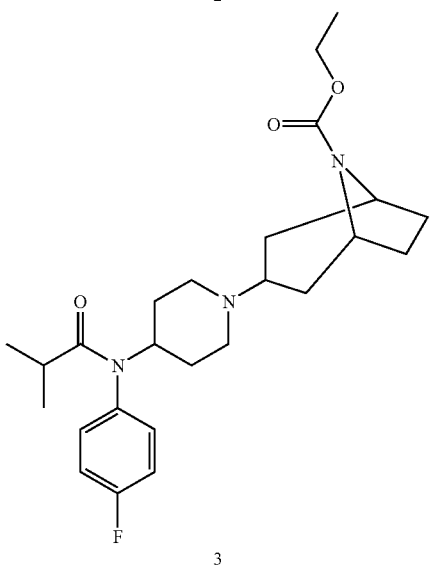

2

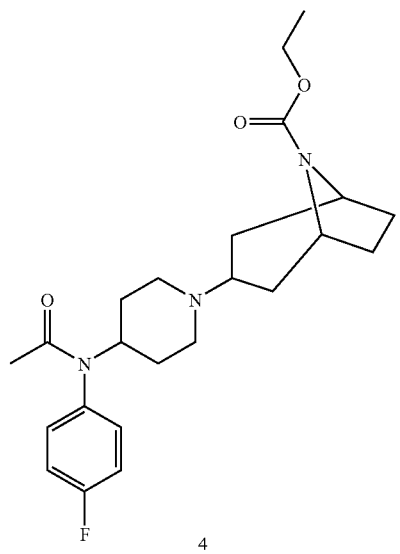

3

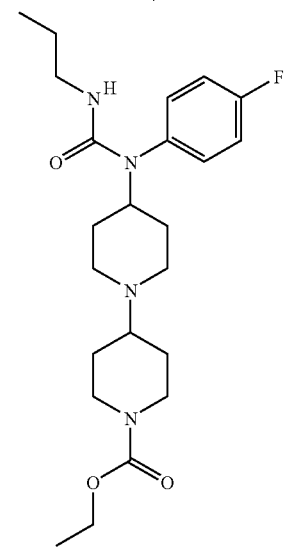

4

-continued
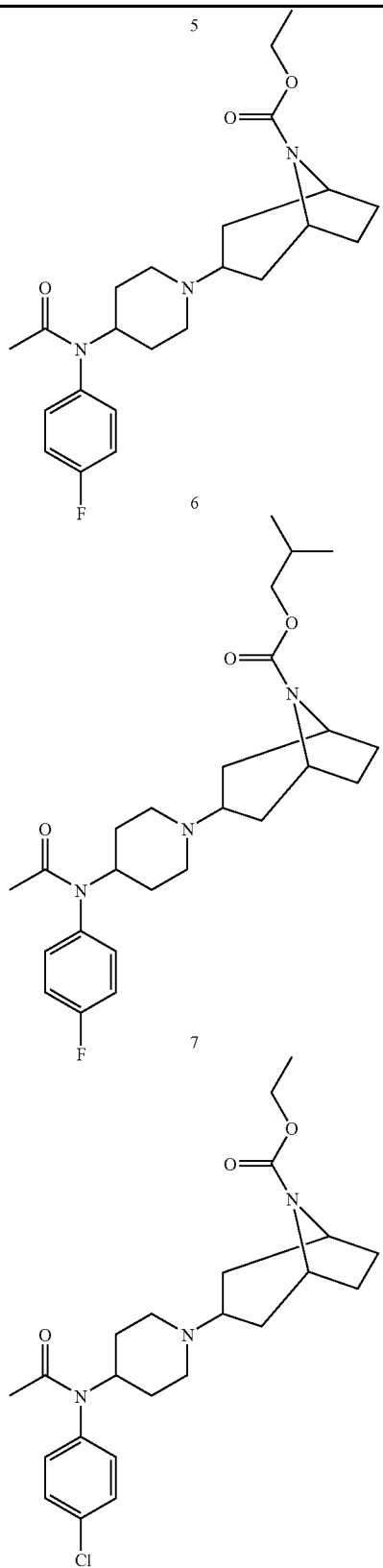
-continued
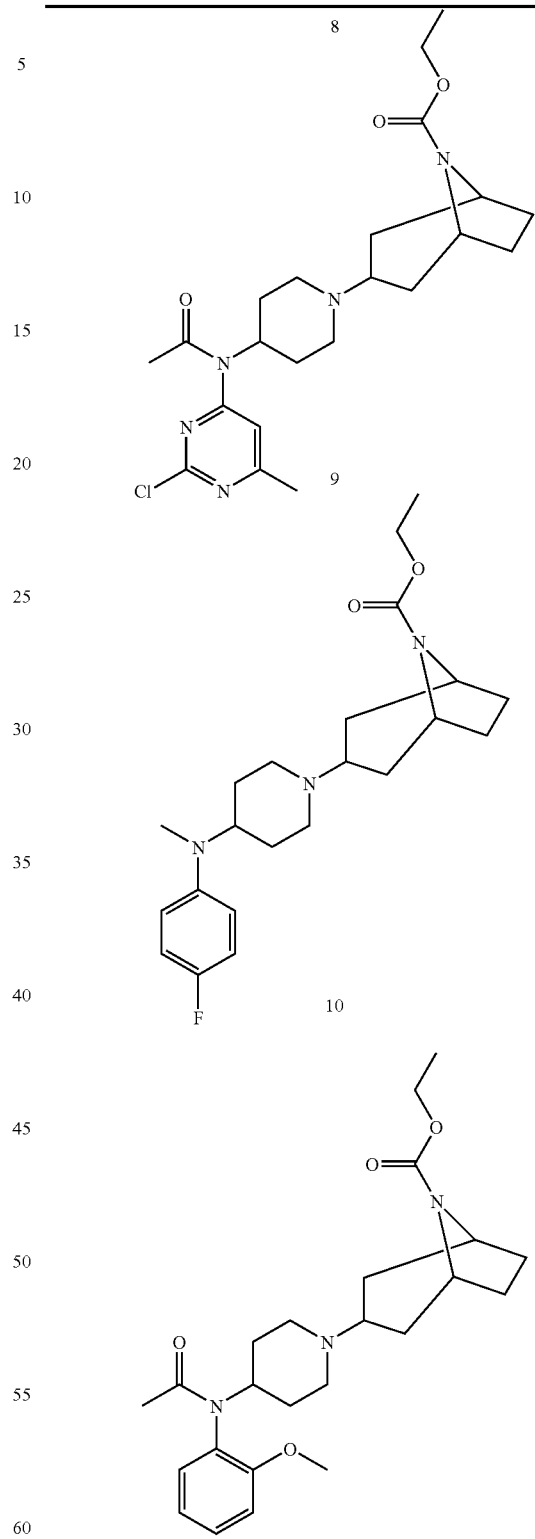

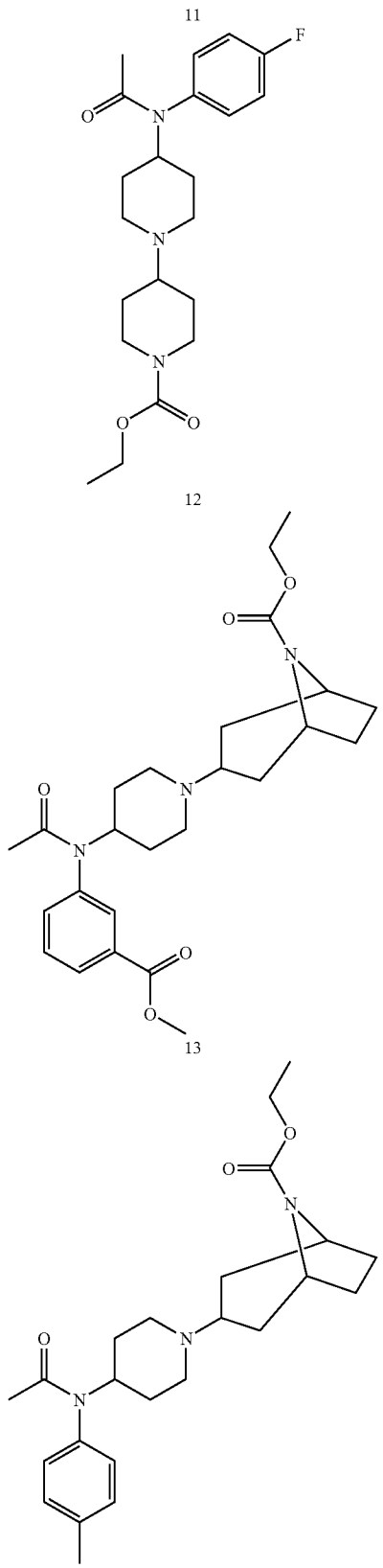

-continued
17
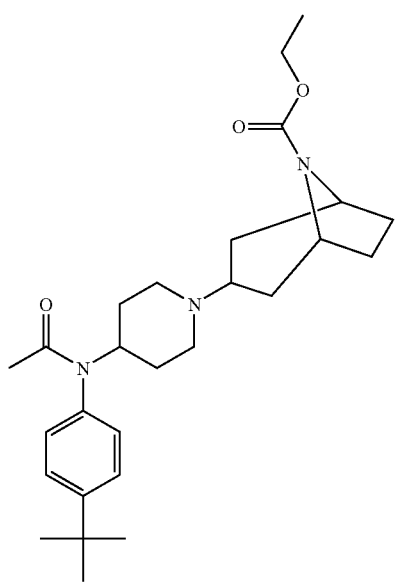
18
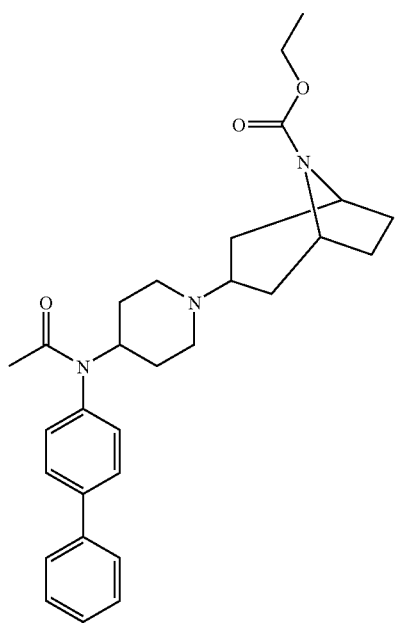
-continued
19
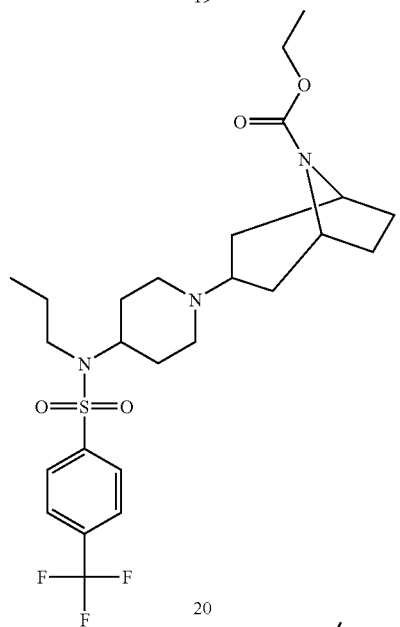
20
21
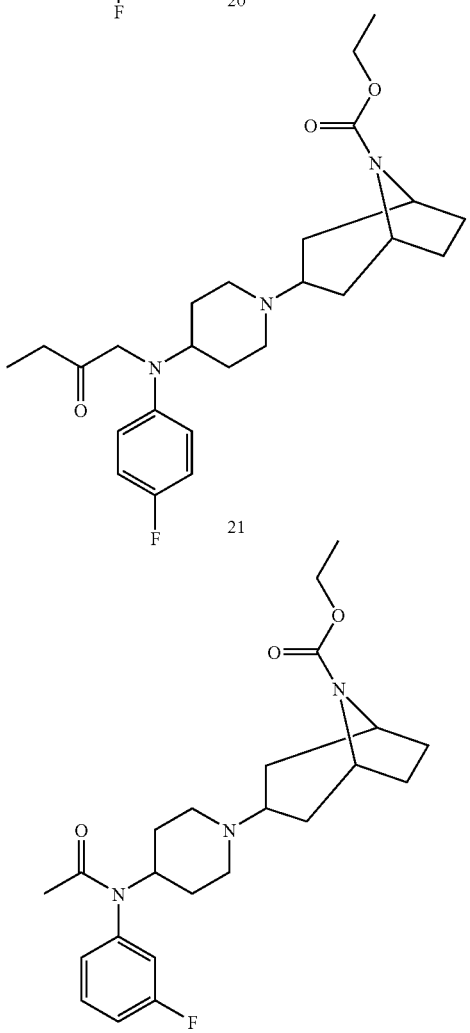

-continued
22
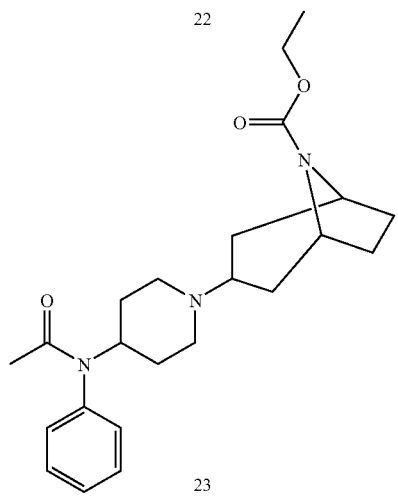
23
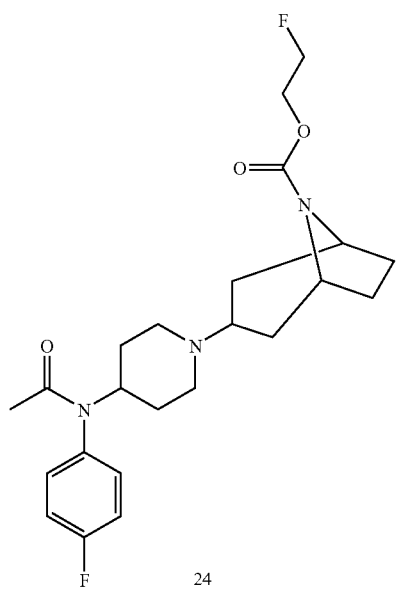
24
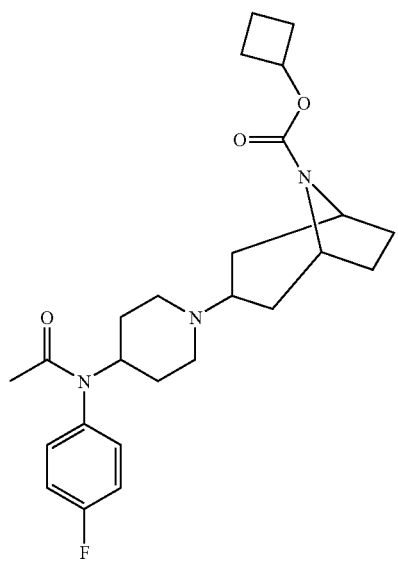
-continued
25
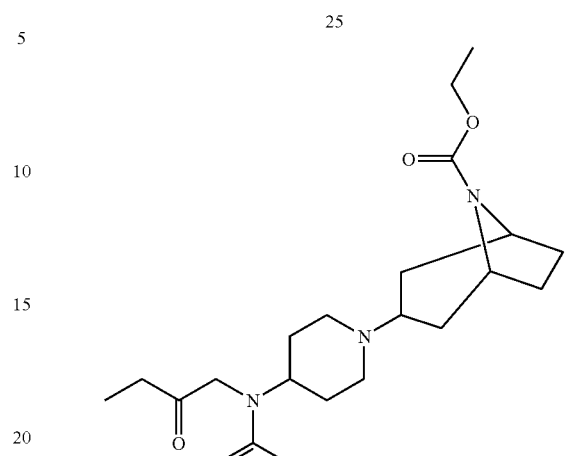
26
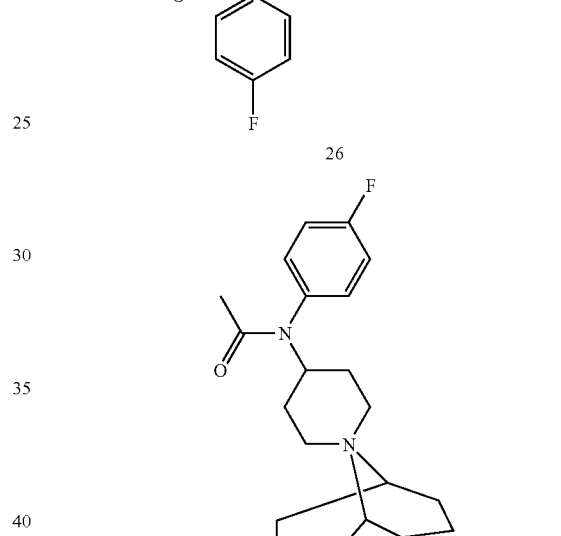
27
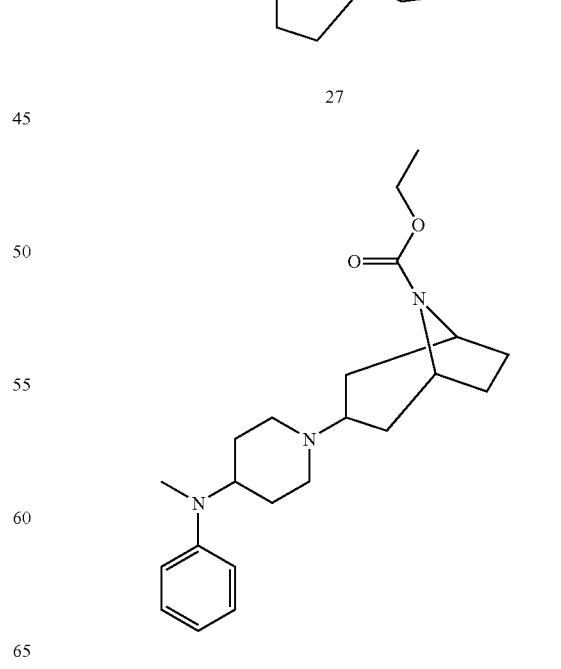

-continued
28
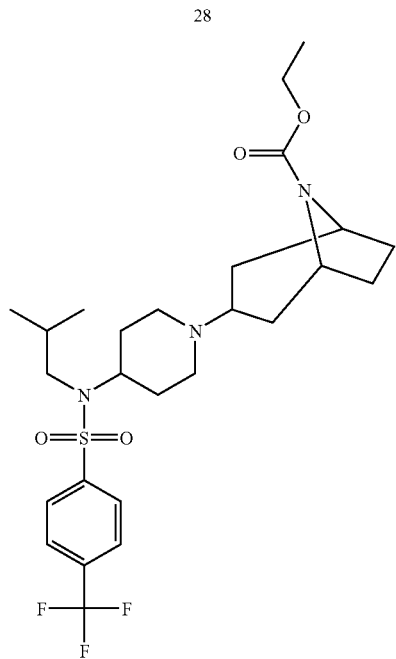
29
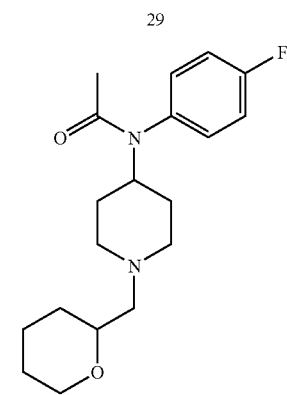
30
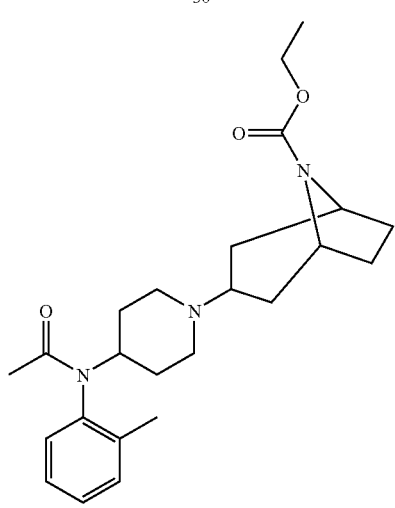
-continued
31
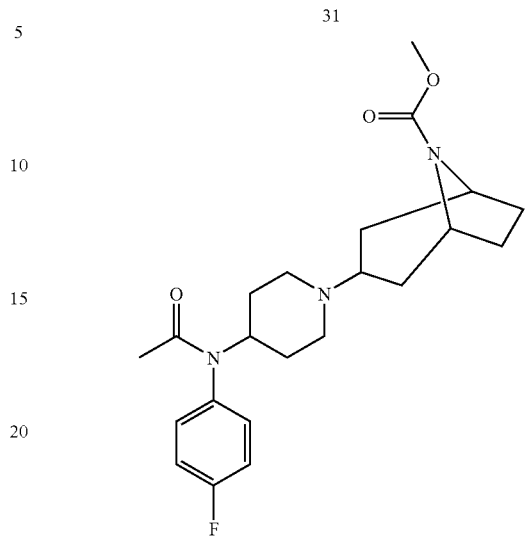
32
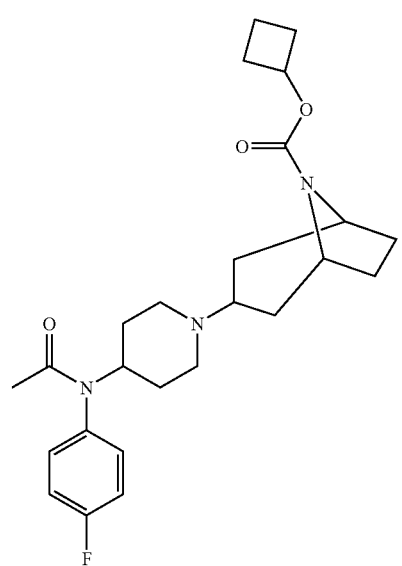
33
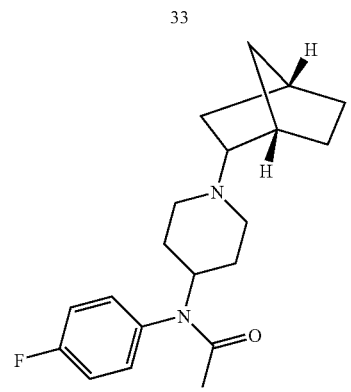

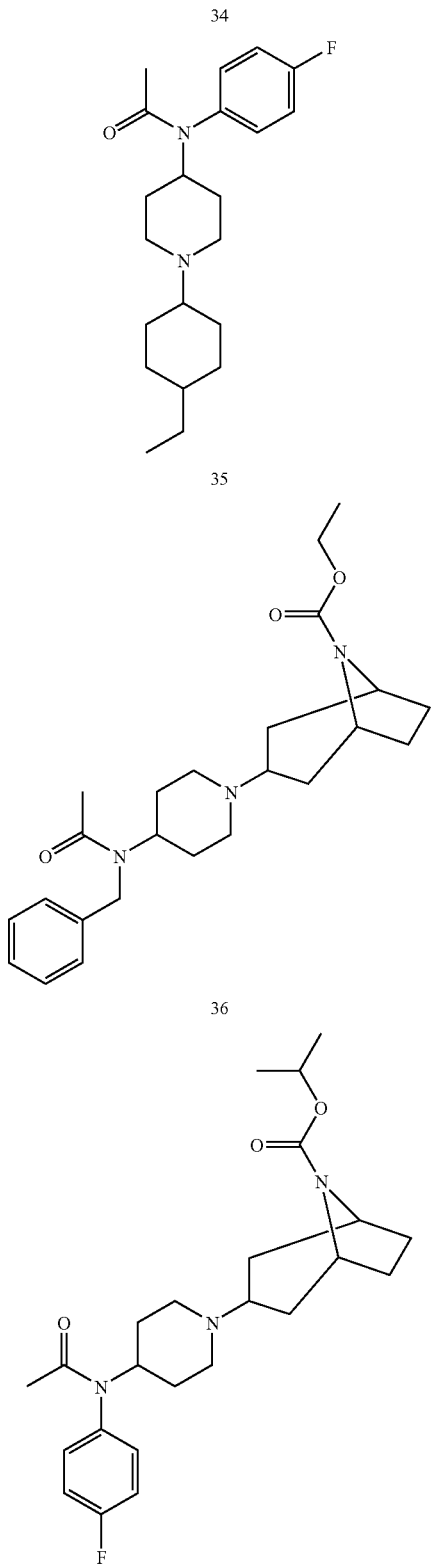
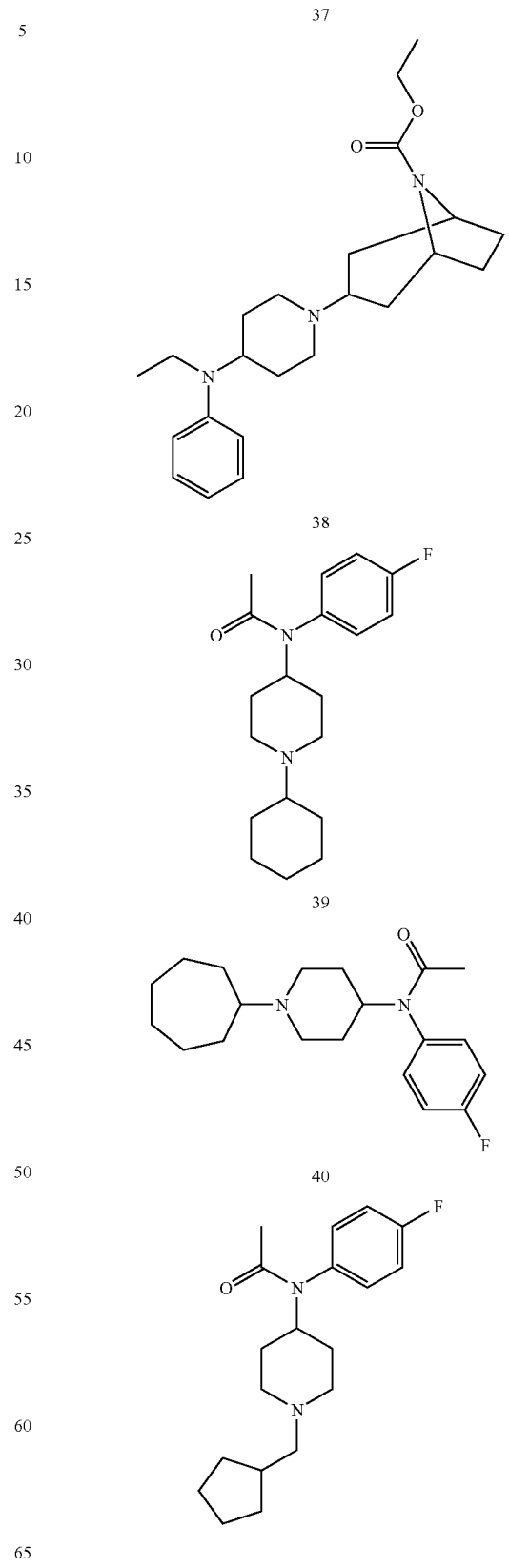

-continued
41
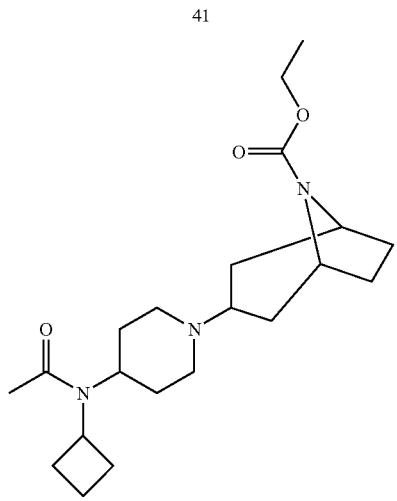
42
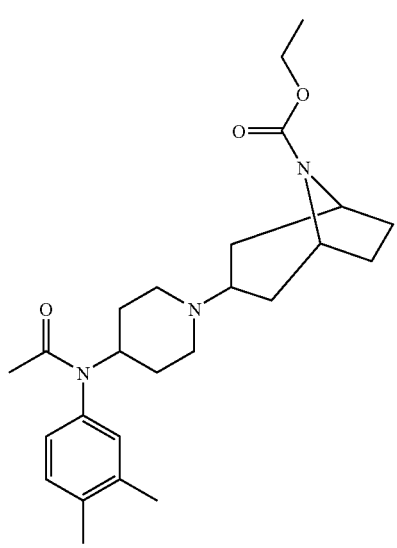
43
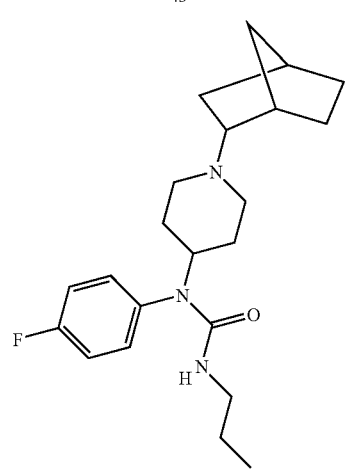
-continued
44
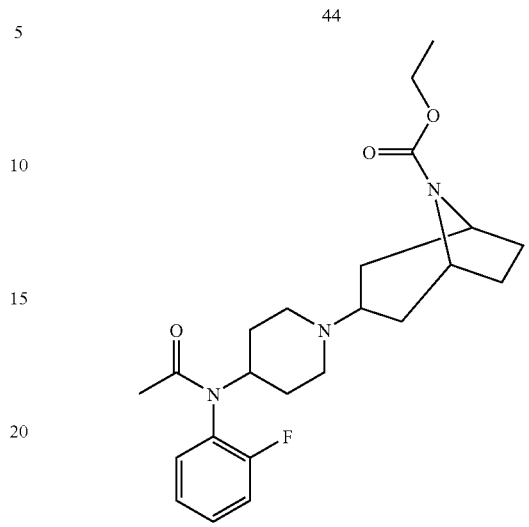
45
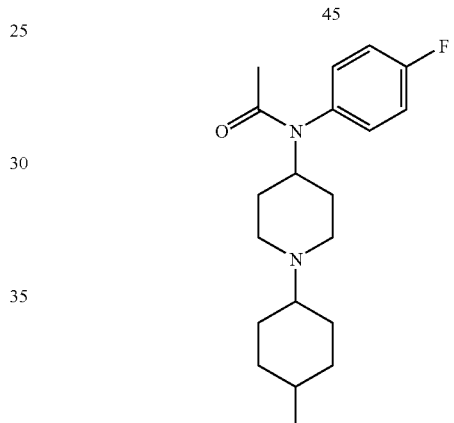
46
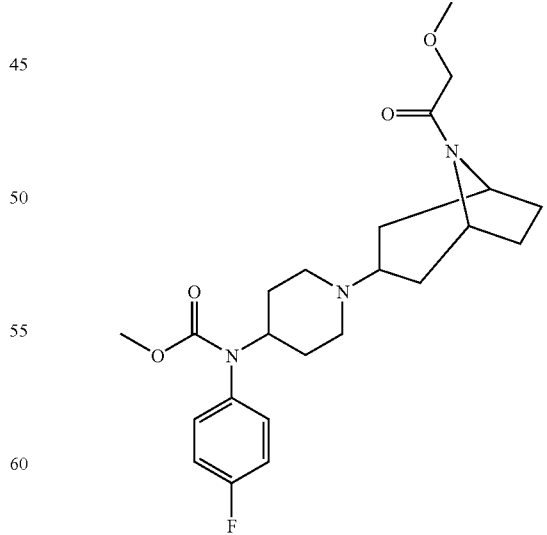

-continued
47
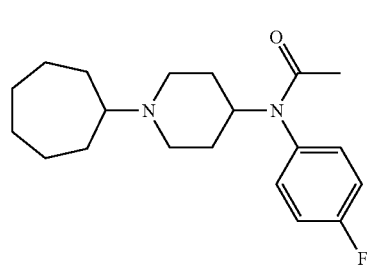
48
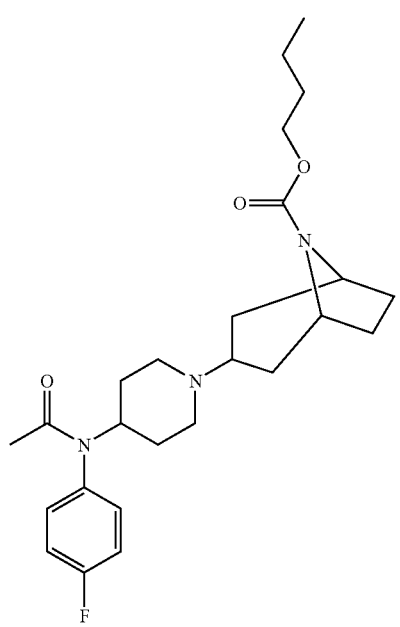
49
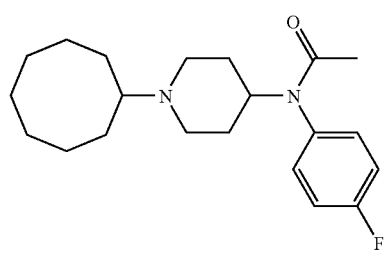
-continued
50
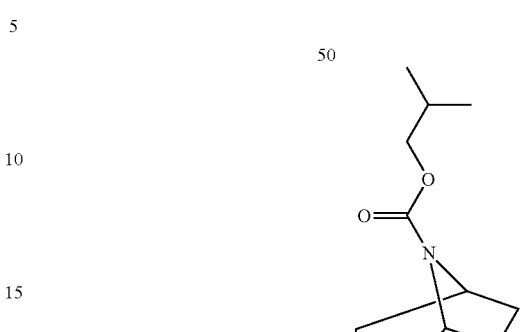
51
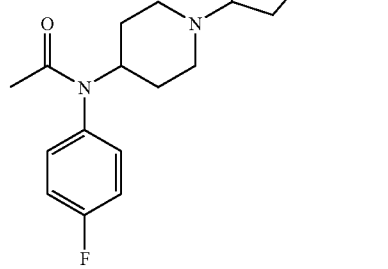
52
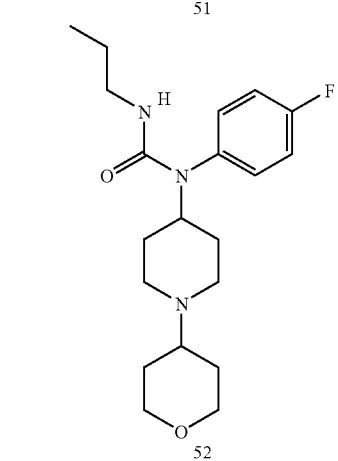

-continued
53
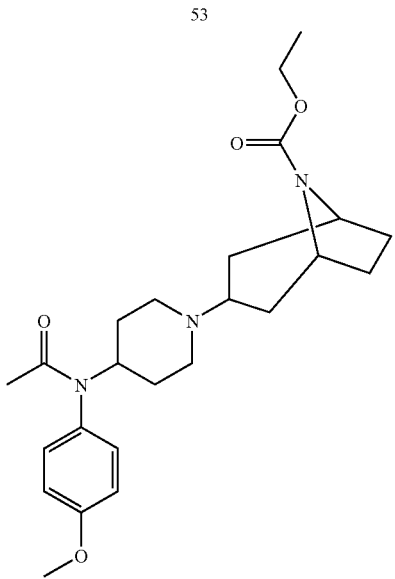
54
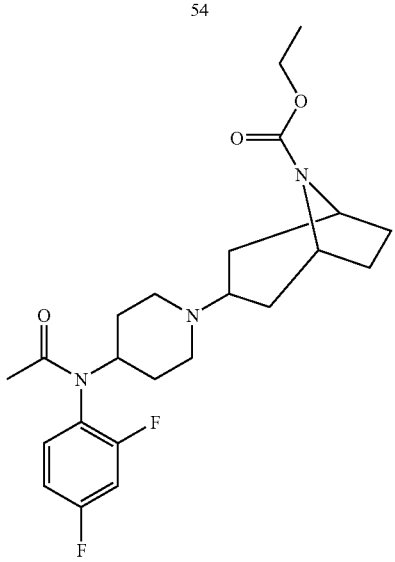
55
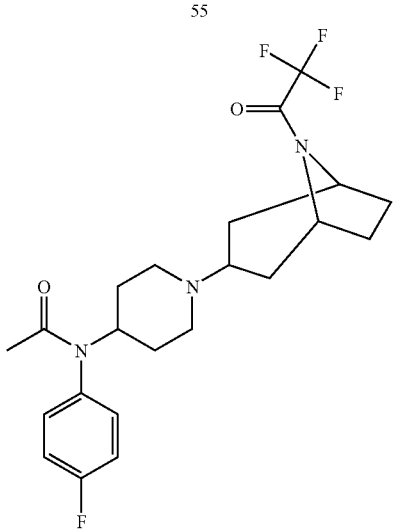
-continued
56
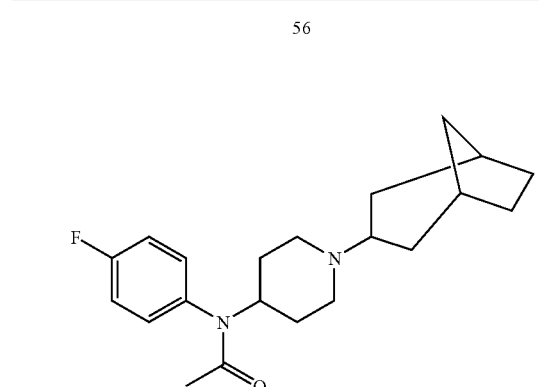
57
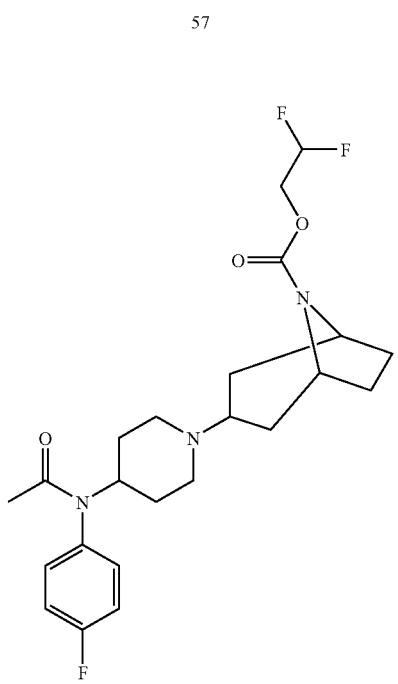
58
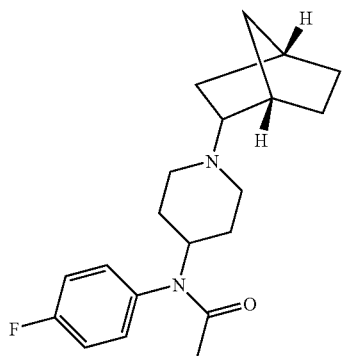

107
-continued
108
-continued
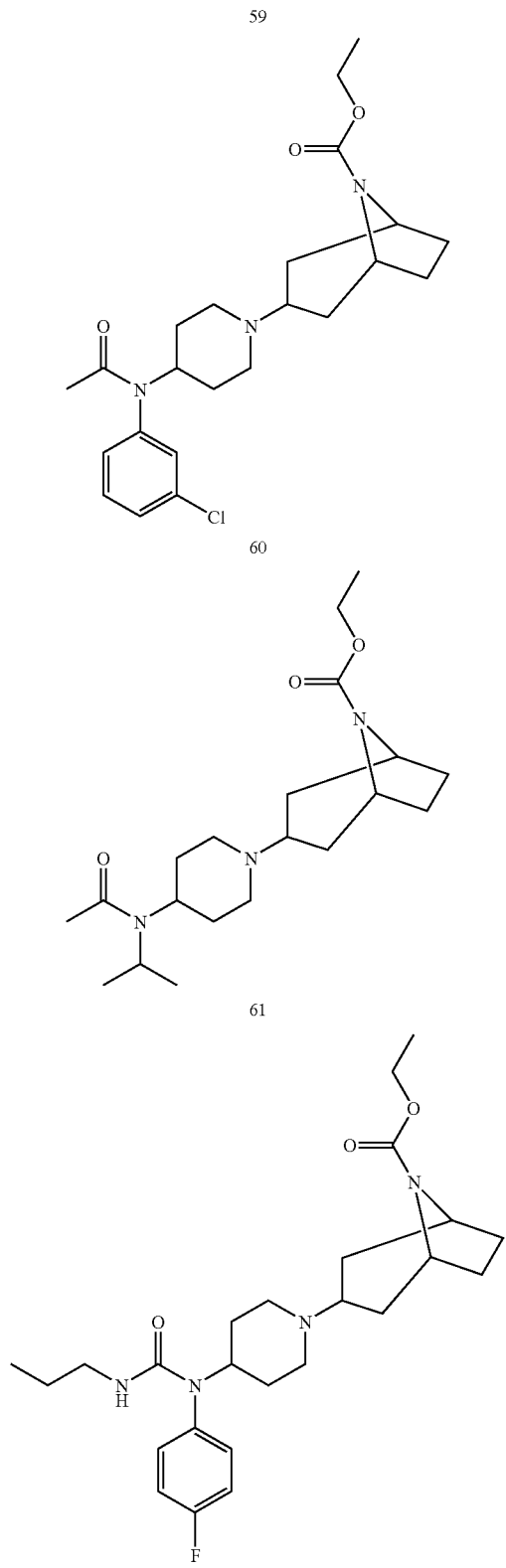
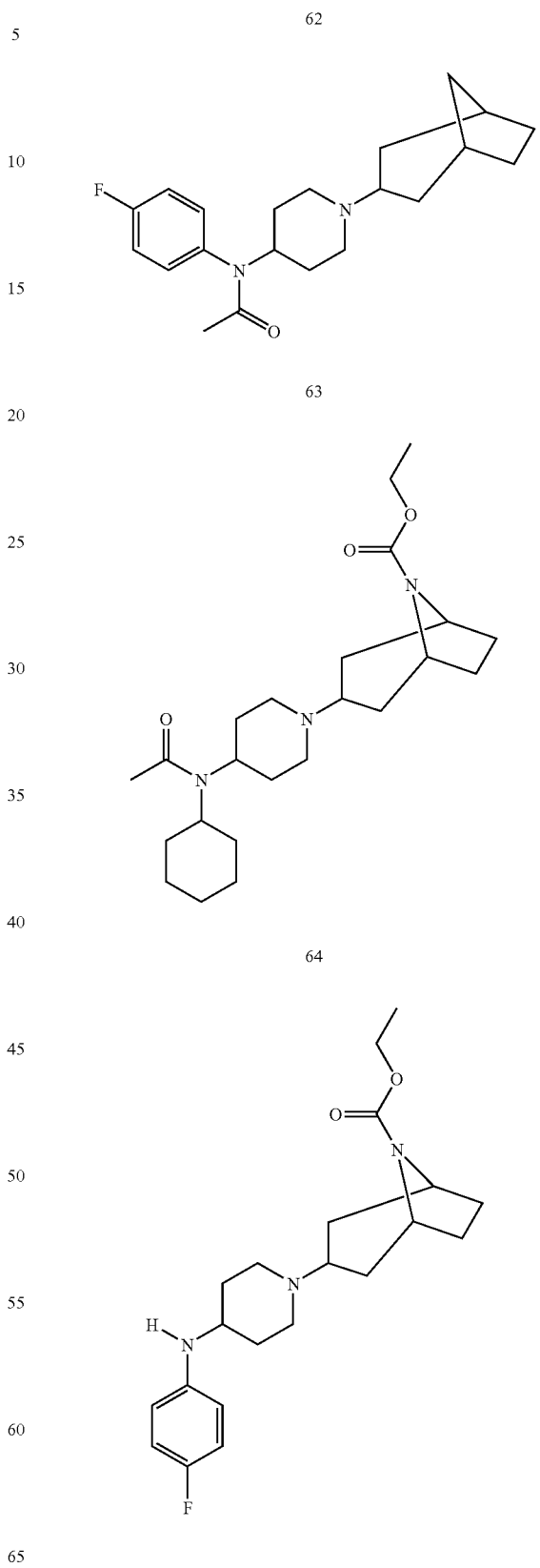

| 109 | 110 |
|---|---|
| -continued | -continued |
| 65<br />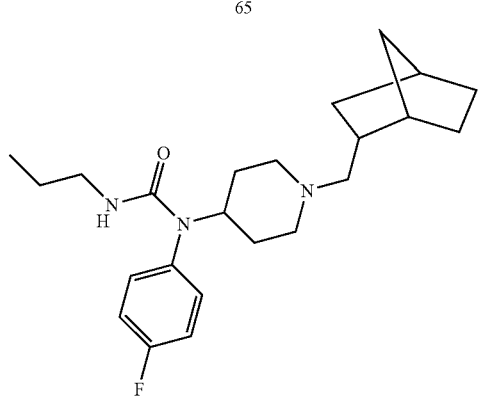 | 68<br />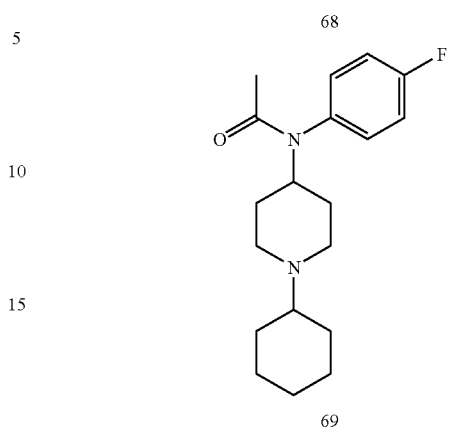 |
| 66<br />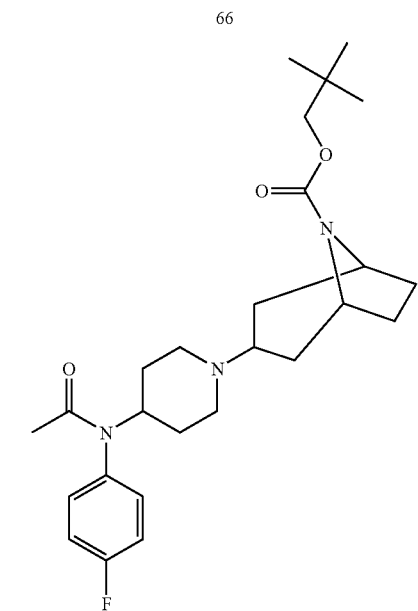 | 69<br />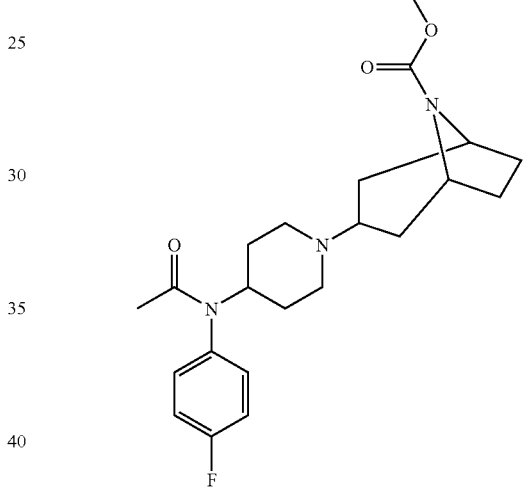 |
| 67<br />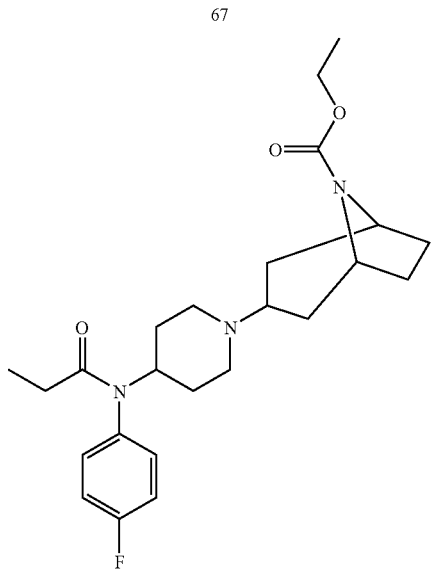 | 70<br />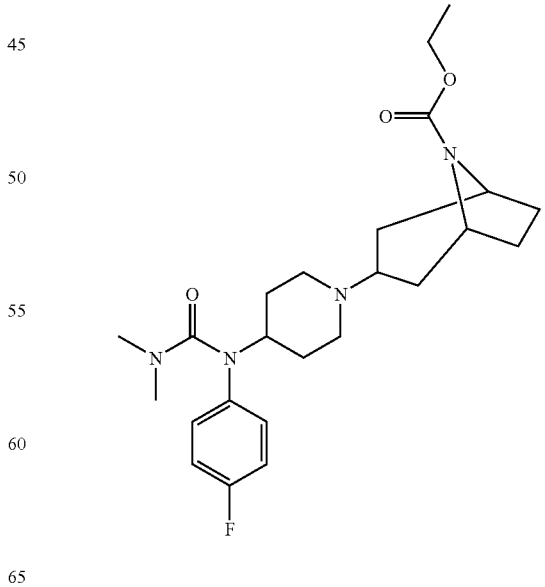 |

-continued
71
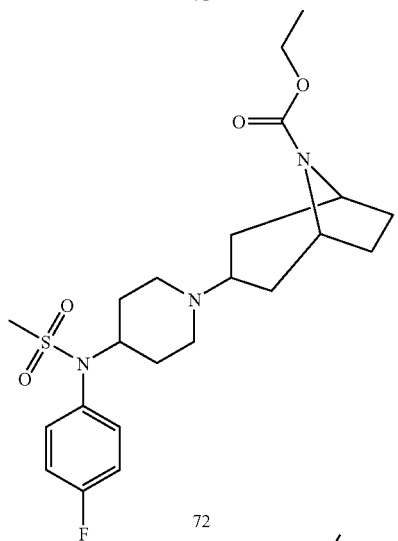
72
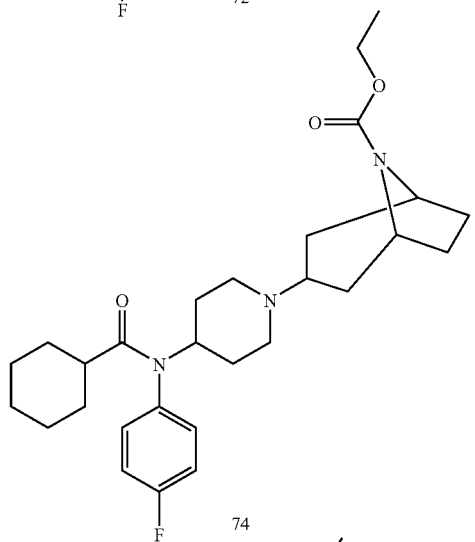
74
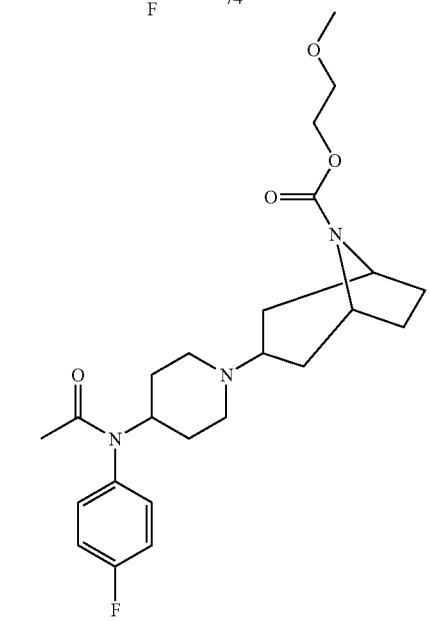
-continued
75
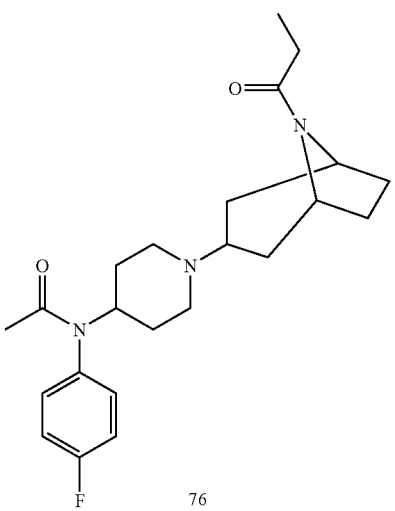
76
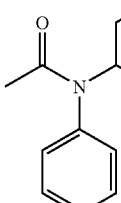
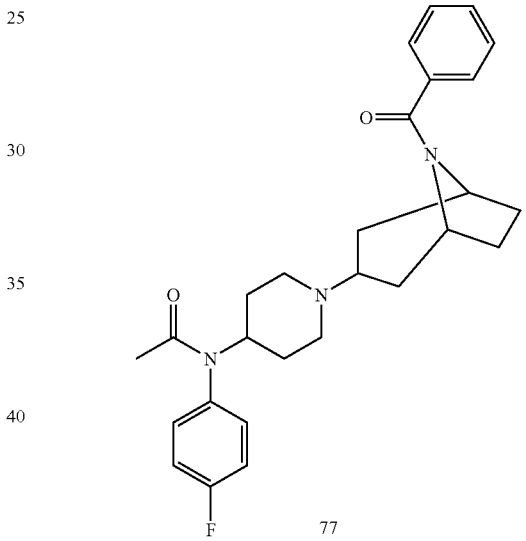
77
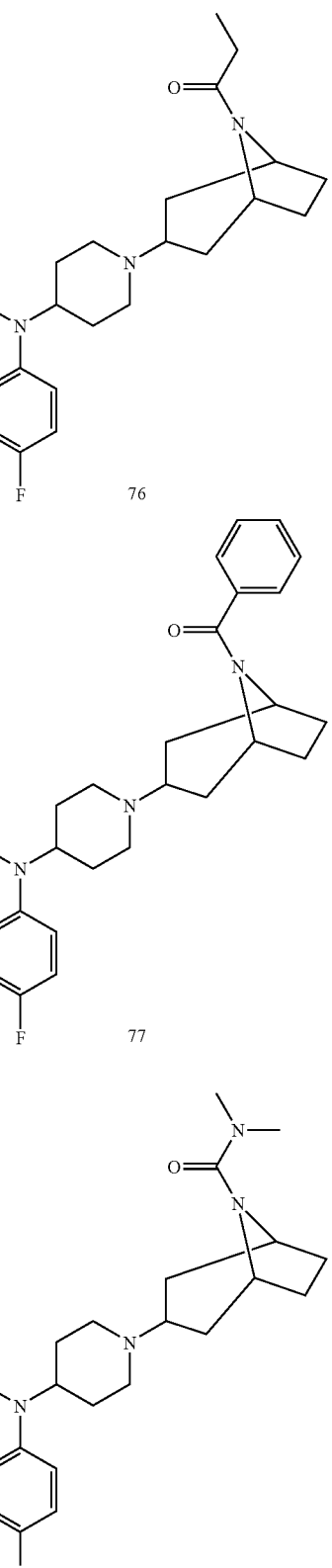

-continued
78
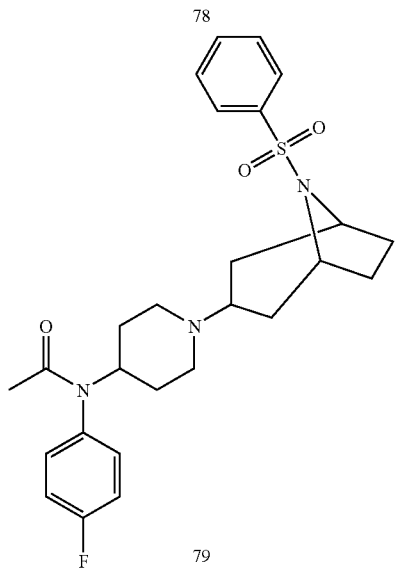
79
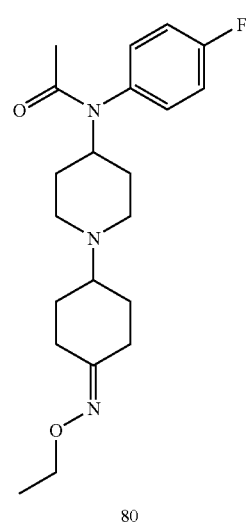
80
-continued
81
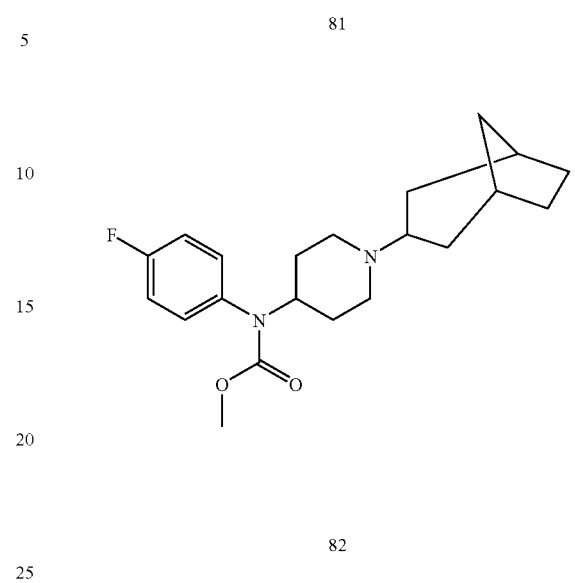
82
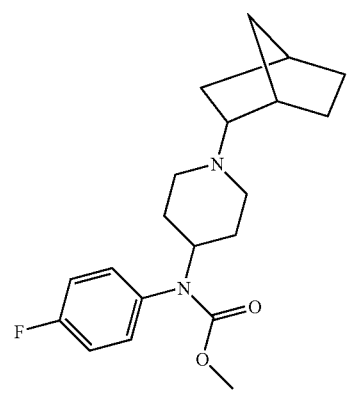
83
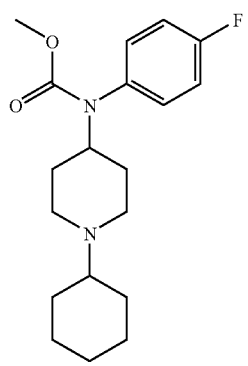

-continued
84
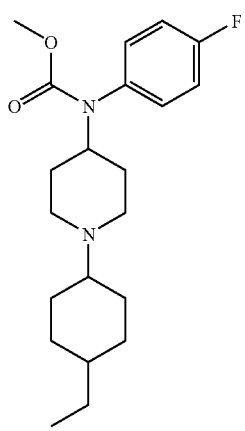
85
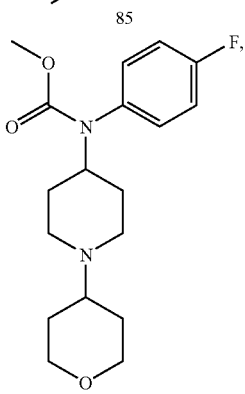
-continued
and
73
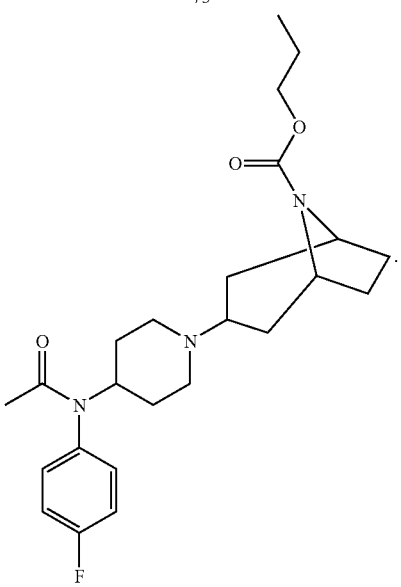
12. A pharmaceutical composition comprising a compound as described in claim 1 and a pharmaceutically acceptable carrier.
13. A pharmaceutical composition comprising a compound as described in claim 11 and a pharmaceutically acceptable carrier.
* * * * *